United States Patent
Agaian et al.

(10) Patent No.: US 10,192,099 B2
(45) Date of Patent: Jan. 29, 2019

(54) SYSTEMS AND METHODS FOR AUTOMATED SCREENING AND PROGNOSIS OF CANCER FROM WHOLE-SLIDE BIOPSY IMAGES

(71) Applicant: The Board of Regents of The University of Texas System, Austin, TX (US)

(72) Inventors: Sos S. Agaian, San Antonio, TX (US); Clara M. Mosquera Lopez, San Antonio, TX (US); Ali Almuntashri, San Antonio, TX (US); Richard Metzler, San Antonio, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 15/215,157

(22) Filed: Jul. 20, 2016

(65) Prior Publication Data

US 2017/0169276 A1    Jun. 15, 2017

Related U.S. Application Data

(63) Continuation of application No. 14/347,912, filed as application No. PCT/US2012/057264 on Sep. 26, 2012.
(Continued)

(51) Int. Cl.
*G06K 9/00* (2006.01)
*G16H 50/30* (2018.01)
(Continued)

(52) U.S. Cl.
CPC .......... *G06K 9/0014* (2013.01); *A61B 5/4381* (2013.01); *A61B 5/7203* (2013.01);
(Continued)

(58) Field of Classification Search
CPC .............. G06K 9/0014; G06K 9/00147; G06T 2207/30096; G06T 7/0012
See application file for complete search history.

(56) References Cited

U.S. PATENT DOCUMENTS 6,269,351 B1    7/2001    Black
6,463,438 B1    8/2002    Veltri et al.
(Continued)

FOREIGN PATENT DOCUMENTS

EP    0 461 902    12/1991
EP    1286280    2/2003
(Continued)

OTHER PUBLICATIONS

International Search Report and Written Opinion for PCT Application No. PCT/US2014/060178 dated Feb. 25, 2015.
(Continued)

*Primary Examiner* — Utpal D Shah
(74) *Attorney, Agent, or Firm* — Meyertons, Hood, Kivlin, Kowert & Goetzel, P.C.; Mark R. DeLuca

(57) ABSTRACT

Systems and methods for detection, grading, scoring and tele-screening of cancerous lesions are described. A complete scheme for automated quantitative analysis and assessment of human and animal tissue images of several types of cancers is presented. Various aspects of the invention are directed to the detection, grading, prediction and staging of prostate cancer on serial sections/slides of prostate core images, or biopsy images. Accordingly, the invention includes a variety of sub-systems, which could be used separately or in conjunction to automatically grade cancerous regions. Each system utilizes a different approach with a different feature set. For instance, in the quantitative
(Continued)

analysis, textural-based and morphology-based features may be extracted at image- and (or) object-levels from regions of interest.

3 Claims, 25 Drawing Sheets

Related U.S. Application Data

(60) Provisional application No. 61/539,827, filed on Sep. 27, 2011.

(51) Int. Cl.

| | | |
|---|---|---|
| G16H 50/70 | (2018.01) | |
| G16H 50/20 | (2018.01) | |
| A61B 5/00 | (2006.01) | |
| G01N 15/14 | (2006.01) | |
| G06T 7/00 | (2017.01) | |
| G06T 7/13 | (2017.01) | |
| G06T 7/181 | (2017.01) | |
| G06T 7/90 | (2017.01) | |
| G06F 19/00 | (2018.01) | |
| G06K 9/46 | (2006.01) | |
| G06K 9/62 | (2006.01) | |
| G06T 5/00 | (2006.01) | |
| G06T 5/20 | (2006.01) | |
| A61B 10/02 | (2006.01) | |

(52) U.S. Cl.
CPC .............. *A61B 5/725* (2013.01); *A61B 5/726* (2013.01); *A61B 5/7257* (2013.01); *A61B 5/7267* (2013.01); *G01N 15/1475* (2013.01); *G06F 19/00* (2013.01); *G06F 19/321* (2013.01); *G06K 9/00127* (2013.01); *G06K 9/00147* (2013.01); *G06K 9/46* (2013.01); *G06K 9/6228* (2013.01); *G06T 5/002* (2013.01); *G06T 5/20* (2013.01); *G06T 7/0012* (2013.01); *G06T 7/13* (2017.01); *G06T 7/181* (2017.01); *G06T 7/90* (2017.01); *G16H 50/20* (2018.01); *G16H 50/30* (2018.01); *G16H 50/70* (2018.01); *A61B 10/0241* (2013.01); *G06T 2207/10024* (2013.01); *G06T 2207/10056* (2013.01); *G06T 2207/20036* (2013.01); *G06T 2207/20081* (2013.01); *G06T 2207/30024* (2013.01); *G06T 2207/30081* (2013.01); *G06T 2207/30096* (2013.01)

(56) References Cited

U.S. PATENT DOCUMENTS

| 7,483,554 | B2 | 1/2009 | Kotsianti et al. | |
|---|---|---|---|---|
| 7,761,240 | B2* | 7/2010 | Saidi .................... | G06K 9/0014 382/128 |
| 7,899,625 | B2* | 3/2011 | Bhanot ............... | G06K 9/00536 702/19 |
| 7,949,181 | B2* | 5/2011 | Padfield ............... | G06K 9/0014 382/128 |
| 8,139,831 | B2 | 3/2012 | Khamene et al. | |
| 2002/0165837 | A1 | 11/2002 | Zhang et al. | |
| 2004/0258310 | A1 | 12/2004 | Giger et al. | |
| 2006/0064248 | A1* | 3/2006 | Saidi .................... | G06K 9/0014 702/19 |
| 2007/0019854 | A1 | 1/2007 | Gholap et al. | |
| 2008/0205518 | A1 | 8/2008 | Wilinski et al. | |
| 2009/0077543 | A1 | 3/2009 | Siskind et al. | |
| 2009/0161928 | A1* | 6/2009 | Khamene ............. | G06T 7/0012 382/128 |
| 2009/0274386 | A1 | 11/2009 | Panetta et al. | |
| 2009/0297007 | A1 | 12/2009 | Cosatto et al. | |
| 2010/0054622 | A1 | 3/2010 | Adams | |
| 2010/0088264 | A1 | 4/2010 | Teverovskiy et al. | |
| 2010/0098306 | A1 | 4/2010 | Madabhushi et al. | |
| 2010/0177950 | A1 | 7/2010 | Donovan et al. | |
| 2010/0312072 | A1* | 12/2010 | Breskin ............... | A61B 6/4057 600/300 |
| 2011/0243417 | A1 | 10/2011 | Madabhushi et al. | |
| 2012/0116716 | A1 | 6/2012 | Lokshin et al. | |
| 2012/0148141 | A1 | 6/2012 | Ozcan et al. | |

FOREIGN PATENT DOCUMENTS

| KR | 100989650 | 10/2010 |
|---|---|---|
| WO | 2009006696 | 1/2009 |
| WO | 2013049153 | 4/2013 |

OTHER PUBLICATIONS

International Preliminary Report on Patentability for PCT Application No. PCT/US2014/060178 dated Apr. 12, 2016.
International Search Report/Written Opinion for PCT Application No. PCT/US2012/057264 dated Apr. 24, 2013.
International Preliminary Report on Patentability for PCT Application No. PCT/US2012/057264 dated Apr. 1, 2014.
Agaian "Visual Morphology", Proc. SPIE, (3646), 139-150 (1999).
Agaian et al. "A new edge detection algorithm in image processing based on LIP-ratio approach", Proc. SPIE, vol. 7532, (2010).
Bezdek "Cluster validity with fuzzy sets," J. of Cybern., vol. 3, pp. 58-71, 1974.
Chang et al. "Texture Analysis and Classification with Tree-Structured Wavelet Transform", IEEE Trans. Image Process, vol. 2, No. 4, pp. 429-441(1993).
Deng et al. "Differentation-based edge detection using the logarithmic image processing model". Journal of Mathematical Imaging and Vision 8, 161-180 (1998) (Abstract).
Deng et al. "The logarithmic image processing model and its applications", IEEE Proc. of the 27th Asilomar Conference on Signals, Systems, and Computers (ACSSC93), 2, 1047-1041(1993).
Dikbas et al. "Chrominance Edge preserving Grayscale Transformation with Approximate First Principal Component for Color Edge Detection", IEEE Proc. ICIP 2007, II,261-264, 2007.
Ding et al. "On the canny edge detector". Pattern Recognition. vol. 34, Issue 3, pp. 721-725 Mar. 2001.
Dony et al. "Edge detection on color images using RGBvector angles", IEEE Proc. of the 1999 IEEE Canadian Conference on Electrical and Computer Engineering Shaw Conference Center, Edmonton, Alberta, Canada , 1999.
Doyle et al "Automated grading of prostate cancer using architectural and textural image features", IEEE International Symposium on Biomedical Imaging: From Nano to Macro ISBI 2007, pp. 1284-1287,2007.
Felsberg "A Novel two-step method for CT reconstruction," BVM, 2008.
Ge et al. A method of Multi-Scale Edge Detection Based on Lifting Scheme and Fusion Rule.Proceedings of 2007 International Conference on wavelet Analysis and Pattern Recognition, Beijing, China Nov. 2-4, 2007.
He et al. "An improved Canny edge detector and its realization of FPGA", IEEE Proc. of the 7th conference on Intelligent Control and Automation, (WCICA2008), 6561-6564, 2008, (Abstract).
Hong-Lei et al. "Road Recognition in High Resolution SAR Image Based on Genetic Algorithm," ICIA ,pp. 649-654, IEEE International Conference on Information Acquisition, 2006. (Abstract).
Huang et al. "Automatic Classification for Pathological Prostate Images Based on Fractal Analysis," IEEE Transactions on Medical Imaging, vol. 28, No. 7, pp. 1037-1050, Jul. 2009.
Huang et al. "Effective Segmentation and Classification for HCC Biopsy Images", Pattern Recognition, vol. 43, No. 4, pp. 1550-1563, 2009. (Abstract).
Jingzhong et al. "A method of edge detection based on improved canny algorithm for the Lidar-depth image", Geoinformatic 2006. SPIE vol. 6419,64190. (Abstract).

(56) References Cited

OTHER PUBLICATIONS

Khouzani et al. "Automatic Grading of Pathological Images of Prostate Using Multiwavelet Transform," Proc. IEEE 23rd Annual International Conference, Engineering in Medicine and Biology Society, vol. 3, pp. 2545-2548, 2001.
Khouzani et al. "Multiwavelet grading of pathological images of prostate" Biomedical Engineering, IEEE Transactions on, 2003, vol. 50 (6), 697-704. (Abstract).
Kogan et al. "Visualization using rational morphology and zonal magnitude-reduction", Proc. SPIE, (3304), non linear image processing IX 153-163(1998).
Koschan "A Comparative Study on Color Edge Detecton", IEEE Proc. ACCV'95, Singapore, III. 547-478, 1995.
Laak et al. "Hue-saturation-density (hsd) model for stain recognition in digital images from transmitted light microscopy," Cytometry, vol. 39, No. 4, pp. 275-284, 2000.
Lai et al. "A Harr wavelet approach to compressed image quality measurement", Journal of Visual Communication and Image representation, No. 11, pp. 17-40 (2000).
Lee et al. "Classification for Pathological Prostate Images Based on Fractal Analysis," Proc. IEEE CISP '08, vol. 3, pp. 113-117, May 27-30, 2008.
Lindeberg "Scale-space theory: A basic tool for analyzing structures at different scales," J. of Appl. Statistics, vol. 21, No. 1-2, pp. 225-270, 1994.
Macenko et al. "A method for normalizing histology slides for quantitative analysis," in IEEE International Symposium on Biomedical Imaging: From Nano to Macro (ISBI), vol. 9. Boston, MA: IEEE, 2009, pp. 1107-1110.
Magee et al. "Colour normalisation in digital histopathology images," in Proc. Optical Tissue Image analysis in Microscopy, Histopathology and Endoscopy (MICCAI Workshop), 2009.
Nercessian et al. "A Generalized Set of Kernels for Edge and Line Detection," Proceedings of SPIE Electronic Imaging 2009, San Jose, CA, USA, vol. 7245, 2009. (Abstract).
Nercessian et al. "Multi-scale image fusion using the Parameterized Logarithmic Image Processing model," in Proc. IEEE Systems, Man, and Cybernetics, 2010.
Nercessian et al."An image similarity measure using enhanced human visual system characteristics," in Proc. SPIE Defense, Security, and Sensing, 2011.
Niethammer et al. "Appearance normalization of histology slides" ser. Lectures notes in Computer Science. Springer, 2010, pp. 58-66.
Oppenheimer "The Pathologic Examination of Prostate Tissue", Phoenix5, 1997, URL: http://www.phoenix5.org/Infolink/oppenpath.html#Tis.
Othman et al. "Colour appearance descriptors for image browsing and retrieval," in Proc. SPIE Electronic Imaging 2008, 2008.
Palomares et al. "General logarithmic image processing convolution", IEEE Transactions on image processing, 15(11), 3602-3608, 2006.
Panetta et al. "Logarithmic edge detection with applications", Journal of computers, 3(9) (2008), 11-19.
Panetta et al. "Human visual system based image enhancement and logarithmic contrast measure", IEEE transactions on systems, man, and cybernetics, part b, 1(38) 174-188(2008).
Panetta et al. "Parameterization of logarithmic image processing models", IEEE Transactions on Systems, Man, and Cybernetics, Part A: Systems and Humans (2007).
Panetta et al. "Techniques for detection and classification of edges in color images", SPIE Proc., vol. 6982, pp. 69820W-69820W-11 (2008).
Panetta "Parameterized logarithmic framework for image enhancement," IEEE Trans. Systems, Man, and Cybernetics, vol. 41, pp. 460-473, 2011.
Peng et al. "Feature Selection based on Mutual Information: Criteria of Max-Dependency, Max-Relevance, and Min-Redundency", IEEE Transactions on Pattern Analysis and Machine Intelegnce, vol. 21, No. 8, pp. 1226-1237, Aug. 2005.

Phoenix5 "Understanding Gleason Grading", Phoenix 5 with permission from CoMed Communications and Vox Medica, 1997. URL: http://www.phoenix5.org/Infolink/GleasonGrading.html.
Pinoli "The logarithmic image processing model: connections with human brightness perception and contrast estimators", Journal of mathematical image and vision,7(4), 341-358(1997).
Reinhard et al. "Color transfer between images," IEEE Comput. Graph. Appl., vol. 21, No. 5, pp. 34-41, 2001.
Rodriguez et al. "Steganography anomaly detection using simple-one-class classification", Defense and Security Symposium (pp. 65790E-65790E). International Society for Optics and Photonics. (2007).
Roushdy "Comparative study of edge detection algorithms applying on the grayscale noisy image using morphological filter", the International Journal on Graphics, Vision, and Image Processing, 6(4), 17-23 (2006).
Roula et al. "A Multispectral Computer Vision System for Automatic Grading of Prostatic Neoplasia" Proc. IEEE International Symposium on Biomedical Imaging , pp. 193-196, 2002. (Abstract).
Ruzon et al. "Color edge detection with compass operator", IEEE Proc. Conference on Computer Vision andPattern Recognition '99, 2, 160-166, 1999.
Sankar et al. "Fractal Features based on Differential Box Counting Method for the Categorization of Digital Mammograms", International Journal of Computer Information Systems and Industrial Management Applications (IJCISIM), Nov. 7, 2010, vol. 2, pp. 011-019, 2010.
Sarkar et al. "An Efficient Differential Box-Counting Approach to Compute Fractal Dimension of Image", IEEE Trans. on Systems, Man and Cybernetics, vol. 24, No. 1, pp. 115-120, Jan. 1994. (Abstract).
Senanayake et al. "Colour transfer by feature based histogram registration," in British Mach. Vision Conf. (BMVC). Citeseer, 2007, pp. 1-10.
Sharifi et al. "A Classified and Comparative Study of Edge Detection Algorithms", Proceedings of the Internaional; Conference on information Technology:Coding and Computing (ITCC 2002).
Shin et al. "Comparison of edge detection algorithms using a structure from motion task," IEEE Transactions on Systems, Man, and Cybernetics, Part B., (4), 589-601 (2001).
Silva et al. "Quantify similarity with measurement of enhancement by entropy," in Proc. SPIE Mobile Multimedia/Image Processing for Military and Security Applications, 2007.
Smith et al. "Similarity Measurement Method for the Classification of Architecturally Differentiated Images" Computers and Biomedical Research vol. 32,No. 1, pp. 1-12, Feb. 1999.
Smith et al. "Effect of pre-processing on binarization", Proc. SPIE, (7534), document recognition and retrieval XVII (2010).
Smith "A tutorial on principal components analysis" Cornell University, USA, (2002), 51, 52.
Stotzka et al. "A hybrid neural and statistical classifier system for histopathologic grading of prostatic lesions" Anal Quant Cytol Histol. (1995); 17(3):204-18. (Abstract).
Tabesh et al. "Automated Prostate Cancer Diagnosis and Gleason Grading of Tissue Microarrays", Proc. SPIE, vol. 5747,pp. 58-70, 2005.
Tabesh et al. "Tumor Classification in Histological Images of Prostate Using Color Texture," Proc. IEEE ACSSC 06, pp. 841-845, Oct.-Nov. 2006.
Tabesh et al. "Multifeature Prostate Cancer Diagnosis and Gleason Grading of Histological Images," IEEE Transactions on Medical Imaging, vol. 26, No. 10, pp. 1366-1378, Oct. 2007.
Tai et al. "Computer-Assisted Detection and Grading of Prostatic Cancer in Biopsy Image", Proc. of the International MultiConference of engineers and Computer scientists IMECS2010, vol. 1, Mar. 17-19, 2010.
Tao et al. "Nonlinear image enhancement to improve face detection in complex lighting environment", International Journal of Computational Intelligence Research, 4(2), 327-336(2006).
Trahanias et al. "Color Edge Detection Using Vector Order Statistics" . IEEE Trans. on image processing, 2(2), 1993.

(56) References Cited

OTHER PUBLICATIONS

Wang et al. "An edge detection algorithm based on Canny operator," Intelligent Systems Design and Applications, ISDA 2007. Issue , Oct. 20-24, 2007 pp. 623-628. (Abstract).

Wang et al. "Progressive Switching Median Filter for the Removal of Impulse Noise from Highly Corrupted Images". Circuits and Systems II: Analog and Digital Signal Processing, IEEE Transactions on (vol. 46, Issue: 1); 1999, 78-80.

Wang et al. "A universal image quality index," IEEE Signal Processing Letters, pp. 81-84, 2002.

Wesolkowski et al. "Comparison of color image edge detectors in multiple color space". ICIP-2000, 796-799, 2000.

Wetzel et al. "Evaluation of prostate tumor grades by content-based image retrieval" Proc. SPIE 27th AIPR Workshop, (1999); vol. 3584, pp. 244-252. (Abstract).

Wharton "Comparative study of logarithmic enhancement algorithms with performance measure," in SPIE Electronic Imaging, 2006.

Yagi "Color standardization and optimization in whole slide imaging," Diagnostic Pathology, vol. 6, No. 1, p. S15, 2011.

Ying et al. "Anisotropic filter based modified Canny algorithm,". Fourth International Conference on Fuzzy Systems and Knolwedge Discovery. Aug. 24-27, 2007 vol. 1, on pp. 736-740.

Yu-Qian et al. "Medical images edge detection based on mathematical morphology". Proceedings of the 2005 IEEE, Engineering in Medicine and Biology 27th annual conference. Shanghai, China Sep. 1-4, 2005.

Zelelew et al. "Application of digital image processing techniques for asphalt concrete mixture images" The 12th international conference of international association for computer methods and advanced geomachines (IACMAG). Goa, India, Oct. 1-6, 2008.

Zelelew et al. "A volumetric thresholding algorithm for processing asphalt concrete x-ray CT images". International journal of pavement engineering, vol. 12, Issue 6, 2011, 543-551 (Abstract).

Zhang et al. "A new edge detection method in image processing", IEEE Proc. of the International Symposium on Communications and Information Technology. (ISCIT2005), 1, 445-448, 2005 (Abstract).

Zhou et al. "Edge detection and linear feature extraction using 2D random field model", IEEE transactions on pattern analysis and machine intelligence, 11(1), 84-95(1989).

Ziou et al. "Edge detection techniques—an overview" International Journal of Pattern Recognition and Image Analysis, 1998.

\* cited by examiner

| COLOR COMPONENTS | | | | | STRUCTURE |
|---|---|---|---|---|---|
| i | COLOR | R | G | B | (class) |
| 1 | | 255 | 255 | 255 | Lumen and non-tissue areas |
| 2 | | 205 | 146 | 178 | Epithelial cytoplasm |
| 3 | | 219 | 133 | 168 | Stroma |
| 4 | | 225 | 77 | 109 | |
| 5 | | 159 | 167 | 203 | Blue mucin |
| 6 | | 90 | 37 | 90 | Epithelial nuclei |

SYSTEMS AND METHODS FOR AUTOMATED SCREENING AND PROGNOSIS OF CANCER FROM WHOLE-SLIDE BIOPSY IMAGES

PRIORITY CLAIM

This patent application is a continuation of U.S. patent application Ser. No. 14/347,912 to Agaian et al., entitled "SYSTEMS AND METHODS FOR AUTOMATED SCREENING AND PROGNOSIS OF CANCER FROM WHOLE-SLIDE BIOPSY IMAGES", filed Mar. 27, 2014, which is the National Stage of International Patent Application No. PCT/US2012/057264 to Agaian et al., entitled "SYSTEMS AND METHODS FOR AUTOMATED SCREENING AND PROGNOSIS OF CANCER FROM WHOLE-SLIDE BIOPSY IMAGES", filed Sep. 26, 2012, which claims priority to U.S. Provisional Patent Application No. 61/539,827 to Almuntashri et al., entitled "EXPERT SYSTEM FOR THE PROGNOSIS AND ANALYSIS OF PROSTATE CANCER USING BIOPSY IMAGES", filed Sep. 27, 2011, all of which are incorporated by reference in their entirety.

BACKGROUND OF THE INVENTION

1. Field of the Invention

The invention generally relates to diagnostic procedures for the detection, analysis, assessment, classification, and grading of cancer from digitized histopathological images. More particularly, the invention relates to the use of computer analysis of biopsy samples to detect and classify/grade and score prostate cancer.

2. Description of the Relevant Art

Prostate cancer is the second killer of American men. Current statistics indicate that 1 in 6 men will suffer from prostate cancer, 1 in 32 men will die from prostate cancer. Although prostate cancer can be diagnosed at early stages, 80% of men diagnosed with prostate carcinoma are above 65 years old.

The risk of developing prostate cancer is commonly attached with the patient's age. In general, doctors recommend males of age 50 or higher to screen for prostate cancer. However, screening could be recommended for males who are at a higher risk of developing prostate cancer even at younger age, e.g. 40-45. Risk factors generally increase the chances of developing prostate cancer. The major risk factor is age, since 63% of prostate cancer cases occur in males of age 65 or older. Furthermore, family history is another major indicator. Men who have a family history of prostate cancer have higher chances of developing prostate cancer. Considering race, it is reported that African American men have a higher rate of developing prostate cancer compared to Asian and Native Americans who have the lowest rate. Considering food diet, it has been shown that diets that are higher in fats may lead to a higher chance in developing prostate cancer.

Biopsies provide the most significant information to urologists by indicating the stage and the grade of prostatic carcinoma using the Gleason grading system.

Tissue samples are sampled by urologists from different prostate areas called "cores" using a hollow needle. When biopsy samples are taken from prostate tissues, they are prepared for observation under microscope by specialized pathologists. Cores are sampled from suspicious and non suspicious areas in order to have prognostic information on the areas where cancerous cells may spread to. Also, sampling different cores would identify cases where cancer is slowly growing compared to other areas where cancer is growing more aggressively.

There are different methodologies and protocols that laboratories follow in preparing slides of prostate biopsies. In one method, for a single core examination, three slides are usually prepared. Each slide may have serial sections of biopsy slices or multiple slices sections from the same core. The number of sectioned slices may vary between 2-4 slices. Assuming that four slices are extracted for each slide, the total number of slices needed to prepare three slides is 12 slices. For serial slices, only the 1st and the 3rd slides are stained using Hematoxylin & Eosin (H&E) or Keratin 903 (K903) prior to pathologists' investigation. Staining is a significant step that clearly differentiates various textural components of the biopsy especially basal cells of the prostate glands. Malignant cells do not have these cells and hence, can be observed clearly. The next step is microscopic investigation where the stained slides 1 and 3 are checked for malignancy. If any suspicious patterns are observed, the 2nd slide is then stained using (K903) and observed. However, if the 3rd slide only shows suspicious patterns, further slices are sectioned from the same core and stained for further investigation. In case of a negative diagnosis of the current core, slides from other cores of the prostate gland are prepared for further diagnosis.

Pathologists grade cancer tissues by observing biopsy samples under the microscope to describe their appearance and architectural features by assigning a grade using Gleason grading system. Gleason system of grading is a significant histology grading method due to its popularity and usage in many medical institutions as well as in literature. The Gleason grading system was named after Dr. Gleason in 1977, who devised a system of five grades to describe and differentiate the unique histology features of each biopsy image excluding the cytological features. The Gleason grading system assigns grades from 1 to 5 according five patterns where grade 1 is the most differentiated pattern, and grade 5 is the least differentiated one. FIG. 1 illustrates the different architectures of these patterns labeled with their corresponding grade. Gleason grade 1: cancerous patterns are composed of generally consistent, well separated, and closely packed glands. This pattern resembles the normal prostate biopsy tissue. Gleason grade 2: tumors of this pattern show less uniformed glands having size and shape variations, with loose arrangements of the glands and more gaps in between. Gleason grade 3: tumor glands in this pattern can be recognizable but with higher variations of shapes (elongated) and mostly smaller in size. Darker cells' nuclei can be noticed leaving the glands and invading the surrounding glands. Gleason grade 4: tumors of this pattern can be recognized by the loss of glands formation, and the inability to separate glands from each other. It has an architectural jump compared to previous grades by having fused and poorly defined structures. The invading of dark nuclei becomes a dominant pattern in this grade. Gleason grade 5: tumors of this pattern have no glandular differentiation and consist of sheets of single cells. They have a total loss of architecture with more dark nuclei pattern spread all over the prostate tissue.

Patterns in Gleason grades 1 and 2 are the least common patterns and seldom occur in general. Gleason pattern 3 and 4 are the most common patterns, and their existence indicate a worsen prognosis in general. Gleason pattern 5 is less common than the previous pattern and seldom seen as diagnosis usually occurs at an earlier stage of cancer development.

During a pathologist's examination of biopsy images, they assign two Gleason grades that represent the most two predominant patterns in the image. The first grade indicates the most dominant pattern, and the second grade indicates the second most predominant pattern. The addition of these two grades yields the Gleason score. For instance, a Gleason score of 7: 4+3 indicates that prostate cancer tumor of pattern 4 is the most dominant pattern, combined with second predominant pattern of grade 3. It is important to note here that a Gleason score of 4+3 is not the same as 3+4. Although this yields a total score of 7, the first and second predominance grades are different at both cases.

During the microscopic observation of Gleason patterns in order to assign the two most predominant grades to the biopsy sample, pathologists may note the existence of a third pattern, or a "tertiary pattern". Tertiary patterns account for almost 5% of patterns belonging to grades 4 or 5 patterns. Hence, pathologists generally report the Gleason score with the tertiary pattern score even if it accounts for less than 5% due to its role in predicting advanced tumor stages at some cases.

Currently, pathologists visually grade prostate biopsy tissues using Gleason scoring system. This approach is very subjective and subject to intra and inter-observer variations. Also, it is a time consuming task and raises difficulties as far as spatial resolution is considered especially in the subgroups of grades 3-5 where further classification is needed. There is a considerable variation of pathologists' grading of prostate biopsy images. For instance, at Johns Hopkins Hospital, it was reported that most "2+2" biopsies sent for evaluation were actually "3+3" biopsies that had been under graded by a general pathologist. Pathologists experience is another factor that contributes to errors in reporting the correct Gleason grades. Most of these errors result in a repeat needle biopsy procedure for the patient that could have been avoided if the original biopsy specimens had been reviewed by more experienced pathologists. In a study conducted on 3,789 patients collected from 18 studies, the following were reported: the exact correlation of Gleason grade was found in 43% of the total cases, the accuracy of Gleason grade plus or minus one grade was found in 77% of total cases, the under grading of prostate carcinoma using needle biopsy occurred in 43%, and the over-grading cases accounted for 15% of the total cases.

There is a clear need of improved systems and methods for screening, quantitative image analysis, and grading of prostate cancer, providing reliable information on the lesion's extension and localization. An accurate diagnosis is a crucial step towards patient treatment selection and management. Several systems have been proposed for prostate cancer detection and grading from digitized biopsy slides. The following patents and patent applications may be considered relevant to the field of the invention:

U.S. Pat. No. 7,761,240 B2 to Saidi et al. discloses systems and methods are provided for automated diagnosis and grading of tissue images based on morphometric data extracted from the images by a computer in a 2-level procedure (detection and grading). The system proceeds as follows: (1) Input image, (2) Background removal, (3) Histogram-based objects segmentation, (4) Image-level and object—level feature extraction, (5) Feature selection and/or classification. The extracted features include: Fractal dimension of binarized image by several thresholds, fractal code, variance of symlet4 wavelet coefficients, color channel histograms and tissue structures classification. The maximum reported accuracy in the detection stage is 96% and 77.6% in the grading stage. These systems do not have explored the integration among the color channels, which could improve the features extraction steps.

U.S. Pat. No. 8,139,831 B2 to Khamene et al. discloses a method for unsupervised classification of histological images obtained from a slide simultaneously co-stained with NIR fluorescent and H&E stains. The system proceeds as follows: (1) Prostate gland units segmentation, (2) Feature extraction, (3) Principal Component Analysis, (4) Bayesian multiclass classification (PIN, Gleason grades 1 to 5). (5) Gleason score is also computed. The extracted features include: gland boundary and region description, structural descriptors of glands by using Voronoi, Delaunay and Minimum spanning tree graph features, as long with textural descriptors (Haralick features and Gabor filters). In this system, only gland centroids are used for graph construction. Some other important structures such as cell nuclei were not explores as a nodes of Voronoi, Delaunay and MST graphs. A drawback of this method is that additional NIR stain must be used. The most widespread in clinical practice is H&E stain.

U.S. Pat. App No. 2010/0098306 A1 to Madabhushi et al. relates to computer-aided diagnosis using content-based retrieval of histopathological (prostate/breast/renal) image features based on predetermine criteria and their analysis for malignancy determination. The method classifies a region into normal, cancerous and suspect. The system proceeds as follows: (1) Input image, (2) Feature extraction, (3) Manifold learning (feature dimensionality reduction and classification) for classification and reclassification at higher magnifications. The extracted features include: first and second order statistics of color channels, graph features (Voronoi, Delaunay and MST from nuclei centers. The features are standard deviation, average, ratio minimum to maximum, entropy of edges and areas of polygons and triangles, Statistics of Co-adjacency matrix constructed from the glands centers), textural features (Haar wavelet feature and Gabor filter response, Sobel, derivatives and Kirsch filter response) and morphology information (nuclear density and gland morphology). The maximum reported accuracy is 92.8% in Grade 3 vs. Stroma recognition. However, the classification between Grade 3 vs. 4 is 76.9%.

U.S. Pat. App No. 2011/0243417 A1 to Madabhushi et al. discloses a method and a system for detecting biologically relevant structures in a hierarchical fashion, beginning at a low-resolution. The relevant structures are classified using pairwise Markov models (PPMMs). The invention provides a fast CAD system for detection/diagnosis of medical images. This invention is used for CaP detection in whole mount WMHS, but can be used for other organs. The extracted features include: Graph features (Voronoi diagram, Dealunay triangulation and MST from lymphocyte centroids) and Gland features and nuclei density. The performance of the system is estimated by using AUC of ROC curves. The maximum reported AUC is 0.812.

U.S. Pat. App No. 2007/0019854 A1 to Gholap et al. discloses a method and a system that provide automated screening of prostate needle biopsy specimen in a digital image of prostatectomy specimen. The system proceeds as follows: (1) Input image, (2) Contrast modification (if needed), (3) structure segmentation (lumen, cells, cytoplasm), (4) filtering of isolated cells in stromal area, (5) cell dilation, (6) gland reconstruction, (7) feature extraction, (8) classification using neural networks. 2-level process (disease detection and further grading). The features are: Number of glands, gland size, shape (circularity, elongation), arrangement and destruction, stroma area, lymphocytes presence, among others.

U.S. Pat. App No 2010/0312072 to Breskin et al. discloses a method of estimating a grade of a prostate cancer from zinc data associated with the prostate, the zinc data being arranged gridwise in a plurality of picture-elements representing a zinc map of the prostate. The method performs cancer grading of at least one tissue region based on zinc levels associated with zinc map. In this case, the assessment of cancer severity is not made from histological quantitative analysis of tissue images.

It is therefore desirable to have more effective and accurate procedures for the detection of prostate cancer using biopsy samples. Unfortunately, all of the above procedures and apparatus suffer deficiencies in the degree of quantitative analysis and diagnostic accuracy in the assessment of human or animal tissue images.

SUMMARY OF THE INVENTION

The large number of disparate, differently-scaled Gleason scoring methods can lead to a variety of misinterpretations of reading actual cancer aggressiveness. We propose generalized scoring methods which simultaneously covers all previous scoring methods by relieving the dependency on only two or three of the most dominant patterns, extending the range of measured patterns to all possible Gleason patterns, and combining all observed Gleason pattern grades into one, continuous-scale Gleason score which is bounded by the traditional Gleason Grade limits, 1 through 5. These novel scores provide a more accurate, unambiguous measure of prostate cancer aggressiveness.

Only few systems have addressed the biopsy whole slide processing. While some of the systems and methods mentioned above are able to classify predefined regions of interest, they do not apply to a biopsy image as a whole. Certain embodiments disclosed herein map Gleason scores to every, individual pixel within a sample image or group of image slides. From each pixel score, local to global measurements about the entire sample are made available.

Furthermore, biopsy assessment through integration of both whole slide 2-D and 3-D systems is described herein. To the best of our knowledge 3-D classification systems have not been investigated for Gleason grading. We propose a novel approach in cancer diagnosis providing a revised Multidimensional Gleason grading when 2-D and 3-D evaluation results are provided. Furthermore, systems and methods for cancer tele-screening by integrating CAD systems and pathologist experience are presented in this invention.

To tackle the limitations of tissue cancer imaging systems, the present disclosure addresses and overcomes the aforementioned limitations of the prior art by providing methods and systems of automated or partially automated quantitative analysis and assessment of human or animal tissue images such as liver biopsy, endometrial biopsy, lung biopsy, lymph node biopsy, renal biopsy, bladder biopsy, rectal biopsy, skin biopsy, and other serial sections/slides of prostate core images. The methods and systems are completely general and independent of the process under consideration.

In an embodiment, a complete scheme/framework for detecting and grading of cancerous lesions through automated quantitative analysis and assessment of human or animal tissue images is provided. The framework detects, grades, predicts stages of cancers on serial sections/slides of core or biopsy images. This output provides information about disease severity, location, and distribution. Specifically, the output of the invention provides both an overall Gleason grade and a "map" of cancerous tissue locations. From this, it is possible to determine the sizes and amounts of tissue affected by cancer, the primary sample grade, secondary sample grades, continuous-scale Gleason score, and higher-order sample grades. Furthermore, it is possible to determine the most likely distribution of grades within a sample.

The framework of the system consists of a diversity of sub-systems. Each sub-system could be used separately or in a combined/fused way. Each system use different approaches. For instance, one sub-system is based on tissue structural and morphology features and other sub-systems are based on textural characteristics of the tissue.

Also provided are systems and methods for accurate detection and mapping of disease in whole slide images, generating so called "cancer maps" by extracting new features and integrating one or more of the classification systems mentioned above.

In one embodiment, new methods for image analysis and description of biopsy images are based on edge detection, transform based features, color and bit-plans based fractal dimensions, and color mapping are described.

In another embodiment, new methods for image analysis and description of biopsy images are based on machine learning, sequential prediction, and information analysis.

In one embodiment, a novel "Hard" Gleason score is generated by (see FIG. 23): Hard Gleason Score=Most Likely Integer Gleason Grade.

In another embodiment, a novel "Soft" Gleason score is generated by (see FIG. 24): Soft Gleason Score=Most Likely Continuous-Scale Gleason Grade.

In another embodiment, a novel "Hard" Gleason map is generated using the most likely Gleason grade of each sample image pixel (see FIG. 25).

In another embodiment, a novel "Soft" Gleason map is generated using the most likely continuous-scale Gleason grade of each sample image pixel (see FIG. 26).

In one embodiment, a novel "Gleason distribution" is generated using the uncertainty in the most likely Gleason grades of each sample image pixel.

The scheme/framework based system and sub-systems have many advantages. They are fast, simple, inexpensive, and provides a screening test for cancer that does not give a high percentage of false negative or false positive results. The method facilitates early detection of the disease and it can be used for screening of large populations. The invention systems can be used by pathologists or without pathologists.

In other embodiments, a novel revised Gleason value is generated by (see FIG. 16): Revised Gleason Value=2D Gleason Grade+3rd Dimensional Core Grade.

In other aspects, systems and methods for the development of a tele-screening system are provided in which the proposed computer-aided diagnosis (CAD) systems are integrated as biopsy readers according to the system configuration, pathologists—expert systems level of agreement and diagnosis decision rules.

Embodiments of the computer-aided system can be used for both: (1) assisting pathologists in several stages. For example: localization of cancer regions in a large digitized tissue biopsy, and grading of detected regions, automated quantitative analysis and assessment, (2) Independent assessment without pathologist interaction.

These and other aspects of the present invention will become evident upon reference to the following detailed description

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
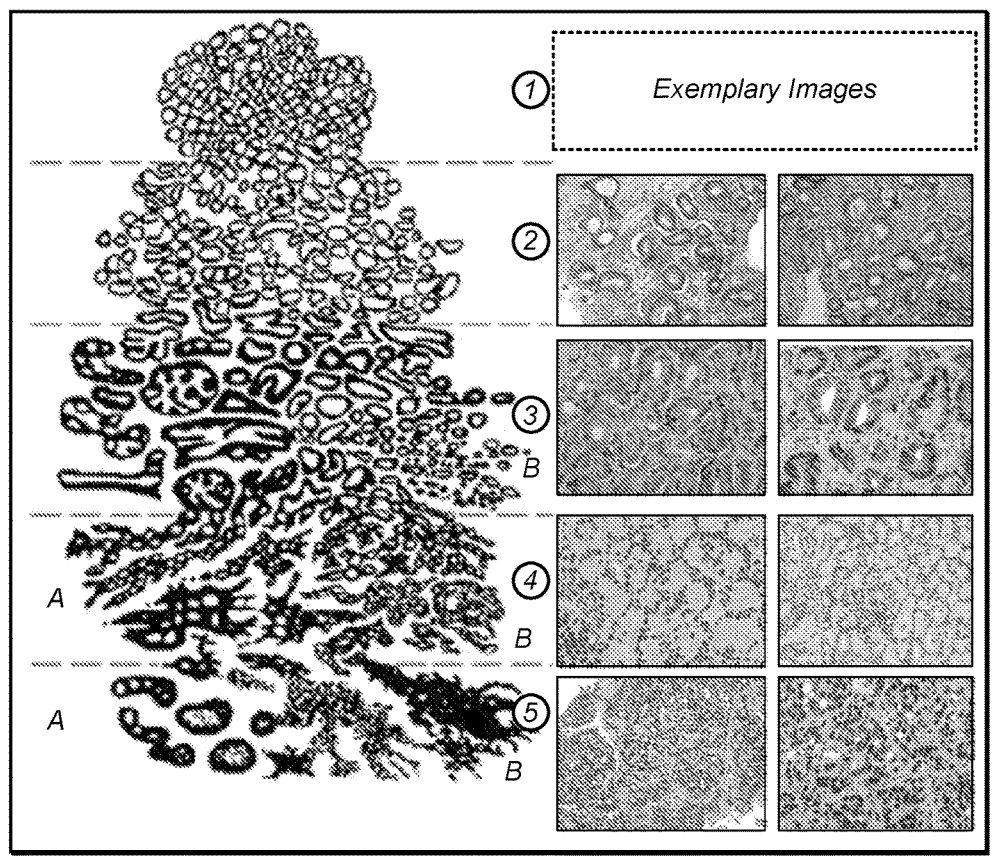
FIG. 1 is visual representation of the Gleason grading system.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Embodiments herein relate to automated quantitative analysis and assessment of human or animal tissue images such as liver biopsy, endometrial biopsy, lung biopsy, lymph node biopsy, renal biopsy, bladder biopsy, rectal biopsy, skin biopsy, and other serial sections/slides of prostate core images. More particularly, but not exclusively, the invention relates to detection, grading, prediction, and staging of prostate cancer on serial sections/slides of prostate core images, or part of biopsy images, which are illustrated as examples.

It is to be understood that the present invention is not limited to particular devices or methods, which may, of course, vary. It is also to be understood that the terminology used herein is for the purpose of describing particular embodiments only, and is not intended to be limiting. As used in this detailed specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. The abbreviation "CaP" refers to prostate cancer.

Described herein is the framework for the development of the cancer grading systems, the functional classification of components and methods for image analysis and systems integration.

The Edge Detection Method

Image edge detection is one of the most effective preprocessing tools that provide essential image edge information and characteristics. An edge detector can be defined as a mathematical operator that responds to the spatial change and discontinuities in a gray-level (luminance) of a pixel set in an image. This method can be used in wide areas such as image segmentation, image categorization, image registration, image visualization, and pattern recognition. These applications may vary in their outputs but they all share the common need of precise edge information in order to carry out the needed tasks successfully. Medical images edge detection is an important step towards object recognition of the human organs such as brain soft tissues, and other different organs. It represents an essential preprocessing work in medical image segmentation. It has also been used for other medical applications concerned with the reconstruction of Computed Tomography (CT) and MRI scans. Conventionally, after image acquisition takes place, various post processing algorithms are applied to these images in order to extract more information. This information can be obtained after edge detection, especially of tissue borders. This process plays a significant rule in recognition of pathological alternations especially in MRI images.

One of the well-known edge detection algorithms is the Canny edge detection method. Canny method has proven to be superior over many of the available edge detection algorithms and thus was chosen mostly for real time implementation and testing. It is considered as the modern "standard" in the sense that the validity of all other algorithms is often checked against it. In Canny algorithm, the Gaussian function is used to smooth the image prior to edge detection. The filtering or smoothing operation actually services two purposes. The first one is the reduction of the effect of Gaussian noise prior to the detection of pixel intensity changes. The second purpose is setting the resolution or scale at which intensity changes are to be detected. These factors contribute effectively towards a precise edge detection method, overcoming the problem of detecting false edges resulted from noise sitting on some pixels.

Canny algorithm has the limitation of being vulnerable to noise disturbances and impulsive noise. Hence, there are certain limitations to its application. Also, the traditional Canny operator has a precise edge positioning but quite sensitive to noise and may detect false edges, as well as missing some details of real edges in an image. This issue is of a great importance in noisy images where many false edges resulting from noise are detected. Furthermore, the Canny edge detector cannot detect branching edges to some extent. Because of the existence of impulsive noise in medical images, traditional Canny algorithm doesn't perform well since it can't eliminate some noise patterns, thus, generating many false edges. It is difficult to design a general edge detection algorithm which performs well in many contexts and captures the requirements of subsequent processing stages. Consequently, over the history of digital image processing, a variety of edge detectors have been devised which differ in their mathematical and algorithmic properties.

Figure 2:
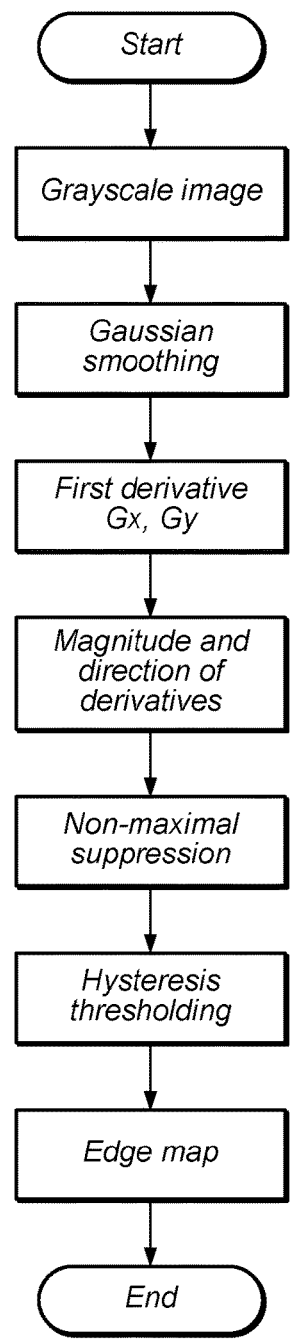
FIG. 2 is a flow diagram of the Canny's edge detection algorithm.

Canny operator consists of the main processes shown in FIG. 2. The major steps of Canny edge detection algorithm can be summarized as follows: (1) Smooth an image with Gaussian filter to have a noise-free image prior to applying the derivative function; (2) calculate gradient magnitude and gradient direction; (3) perform non—maximal suppression to ensure the desired edge with one single pixel width; (4) Determine two threshold values, and then select possible edge points and trace edges.

In one limitation with the Canny method, gradient magnitude and direction are calculated by pixels within a 2-by-2 neighborhood is sensitive to noise and may detect false edges. Another limitation is the failure to detect branched edges and curves especially in neighborhoods where the change in intensity values is inconsiderable. Furthermore, non-maximal suppression can have a negative impact on edge detection precision and may miss some edge connected points. However, it becomes a very essential task to detect all of these edges especially in medical scans where a diagnosis decision is going to be made. The developed algorithms proposes different modifications to the existing Canny algorithm that succeeds in detecting more edge details as well as image denoising when compared to the traditional Canny edge algorithm. Also, one might note that the upper and lower threshold levels are fixed at Canny algorithm regardless of the nature of the image. The determination of such threshold values needs to be an image dependent procedure where the characteristics of different images/edge information are utilized for an automated selection of threshold levels.

There are a few improved algorithms that were developed based on the traditional Canny algorithm that has a superior performance to suit our recognition purposes. Such proposed algorithms may include replacements/modifications of different processes in Canny method. In one embodiment of the present invention, a novel algorithm provides methods for multiple edge detection. This algorithm has a superior performance in localizing and detecting edges that cannot be detected using the classical edge detection techniques, including Canny's method. To this end, several modifications to the original Canny's algorithms are introduced:

(1) Improved preprocessing: Gaussian smoothing filter is replaced by median/adaptive median filter depending on the nature of noise in the image. This enhances the accuracy of detecting true edges at areas of interest as well as avoiding the detection of noise edges that could not be removed using the Gaussian filter.

(2) Improved calculation of the gradient vector: introducing different kernel sizes at the traditional 9-pixels neighborhood area replacing the existing 3×3 kernel. This adds more freedom in calculating the magnitude at different directions other than 45 and 135 degrees. Also, other algorithms may place certain weights of the gradient at the direction of interest.

(3) Improved selection of threshold values: algorithms utilizing adaptive approach in automating the selection of threshold values may replace the existing fixed threshold values introduced by Canny. This improves edge preservation at different areas of the image.

(4) Improved non-maximal suppression (NMS): Canny NMS process compares pixels in the n-pixels neighborhood area at eight different directions in order to determine local maxima. An improved algorithm considers dividing the area into different sub-areas and applies NMS at each area before a final decision is made about the local maxima.

In an embodiment, an approach in edge detection is developed based on dynamic range enhancement algorithm. The introduced algorithm succeeds in integrating the concepts of logarithmic ratio of human visual system with contrast enhancement in order to develop a new edge detection method. The developed method has the advantage over other traditional methods in terms of enhancing, detecting, and segmenting different spots and shapes having significant dark gray levels. The introduced algorithm is tested on different classes and shows a superior performance compared to Canny's edge detection operator. Also, it has the advantage of the precise segmentation and topology/shape preservation of regions of interest needed for further measurements and analysis purposes. In the embodiment algorithm, a non-linear image enhancement which is based on Human Visual System (HVS) dynamic range is integrated with morphological log-ratio approach in order to come up with an effective edge detection operator that is sensitive to edges of dark areas in the image. In applications where edges of interest are represented by dark gray levels such as cracks texture, a pre-processing step is needed where spatial filters such Gaussian/median filters are used to smooth the image prior to applying any sort of enhancement to avoid noise enhancement.

As mentioned previously in an embodiment, a Human Visual System (HVS)-based contrast enhancement and edge detection algorithm may be used to analyze images. The introduced algorithm integrates image enhancement, edge detection and logarithmic ratio filtering algorithms to develop an effective edge detection method. Also a parameter ($\beta$) is introduced to control the level of detected edge details and functions as a primary threshold parameter. The introduced algorithm functions in tracking and segmenting significant dark gray levels in an image. Simulation results have shown the effectiveness of the introduced algorithm compared to other traditional methods such as Canny's algorithm in preserving object's topology and shape. The developed algorithm functions at various applications where measurements and segmentation of dark gray level spots for classification and tracking purposes are required such as road cracks, lunar surface images, and remote objects.

The Human Visual System (HVS) is responsible for transferring data into information received by the viewer. The received information can be characterized by attributes such as brightness, edges, and color shades. Considering brightness, it can be shown that it is not a simple function of intensity when simultaneous contrasts are considered since it relates the perceived brightness of a given region to its background. The reason behind this is that our HVS perception is sensitive to luminance contrast rather than the absolute luminance values themselves. Also, one might consider eyes sensitivity to white noise added to a uniform background more than in an area with a high contrast. Eyes are more sensitive to random noise in smooth areas of an image than in busy areas with many details. Hence, it is obvious that HVS is not a simple function of intensity. Weber's law depends on the ratio of intensity values at two points $f(x,y)$ and $f_o(x,y)$ more than the difference of these values according to the following Weber's law:

$$\frac{|f-f_o|}{f_o} = \frac{\nabla f}{f_o} = \omega \text{ (Weber's constant)}$$

In another application of parameterized logarithmic image processing (PLIP), images are processed as gray tone function according to the following expression:

$$g(i,j)=M-f(i,j)$$

To begin with, the concept of parameterized logarithmic image processing (PLIP) was designed to both maintain the pixel values inside the bounded range [0,M] where M is the maximum value of the range. For instance, M could be 256 for 8 bit gray level images. Also, PLIP model processes images from human visual system (HVS) point of view in a more accurate way. The usual arithmetic operations such as addition and scalar multiplication are argued not to be suitable for human visual system. The PLIP model considers processing images as gray tone functions. The relationship between the traditional gray level function and the gray tone function is given in as follows:

$$f(x,y)=M-\tilde{f}(x,y)$$

Where M is the maximum value of the range. The various operations associated with PLIP include the PLIP addition, PLIP subtraction, and PLIP multiplications. The operation of interest in the developed edge detection algorithm is the PLIP addition operation. For two gray tone functions a and b, and an arbitrary linear function $\gamma(M)=AM+B$ for constants A and B, the PLIP addition is defined as:

$$a \oplus b = a + b - \frac{ab}{\gamma(M)}$$

In order to develop PLIP-based edge detection, Canny algorithm operations are modified to suit PLIP operations. The gradient magnitude g and direction $\theta$ calculations are replaced by PLIP-based formula as follows:

$$\text{Magnitude } g=M(1-\exp((-\sqrt{\overline{gx}^2+\overline{gy}^2})/M))$$

$$\text{Direction } \theta=\text{Arc tan}(\overline{gx},\overline{gy})$$

As an example of this embodiment, gx and gy may be defined in a m×n window m, n=1, 2, 3 . . . . The values of m and n may be arbitrary and should be selected according to the application. For instance, a window of 3×3 of 9 gray tone pixels may be generated as follows:

$$\begin{array}{ccc} f_1 & f_2 & f_3 \\ f_4 & f_5 & f_6 \\ f_7 & f_8 & f_9 \end{array}$$

$$g_x = M - M\left(\frac{\tilde{f}_3\tilde{f}_6^2\tilde{f}_9}{\tilde{f}_1\tilde{f}_4^2\tilde{f}_7}\right), \quad g_y = M - M\left(\frac{\tilde{f}_1\tilde{f}_2^2\tilde{f}_3}{\tilde{f}_7\tilde{f}_8^2\tilde{f}_9}\right) \quad \overline{g} = \varphi(g)$$

where $\varphi(g)$ is described as isomorphism operator:

$$\varphi(g) = -M\ln\left(1-\frac{g}{M}\right)$$

This section illustrates the mathematical derivation used in developing the new edge detector. In current classical edge detection methods, an edge is detected based on a variation of gray level intensity levels. The levels of detected edges details are controlled by the selection of threshold levels where a lower threshold value corresponds to more edge details and vice versa. In this introduced approach, edges are detected based on the difference of adjacent pixels' gray levels instead. The gray level difference is described for the horizontal and vertical directions as follows:

$$\Delta_x I(i,j)=I(i,j)-I(i-1,j); \Delta_y I(i,j)=I(i,j)-I(i,j-1)$$

Such difference in gray levels is applied also using the ratio operation of the same surrounding pixels. The maximum ratio only should be selected when examining rows falling/rising edges, and column falling/rising edges.

Rational morphological operations have been investigated in order to design rational morphological filters:

$$R = \left(\frac{MF1}{MF2}\right)^\alpha, \quad R = \frac{\sum_{i=1}^m a^i \left(\frac{MF1}{MF2}\right)^i}{\sum_{j=0}^n b^j \left(\frac{MF1}{MF2}\right)^j}$$

Where MF1 and MF2 represent two different classes of filters $a^i$ and $b^i$, i=0, 1, . . . m are constants.

Other forms of the developed visual filters deploy logarithmic ratio as the following examples:

$$\left(\frac{\log MF_i}{\log MF_j}\right)^n ; \left(\frac{\log(MF_i) \ominus \log(MF_j)}{\log(MF_i) \oplus \log(MF_j)}\right)^n$$

The basic steps of the new algorithm are the following: (1) Smooth an image with shape dependent filter. (2) Calculate the joint shape-dependent gradient magnitude and direction. (3) Fusion of edge images. Some examples of this embodiment are the following:

Step 1: For example the Smoothing operator could be the Gaussian kernel, or $$\begin{bmatrix} -1 & -1 & -1 \\ -1 & \alpha & -1 \\ -1 & -1 & -1 \end{bmatrix}, \begin{bmatrix} & & -1 & & \\ & -1 & -2 & -1 & \\ -1 & -2 & \alpha & -2 & -1 \\ & -1 & -2 & -1 & \\ & & -1 & & \end{bmatrix},$$

$$\begin{bmatrix} & & -1 & & \\ & & -2 & & \\ -1 & -2 & \alpha & -2 & -1 \\ & & -2 & & \\ & & -1 & & \end{bmatrix}, \begin{bmatrix} & & -1 & & \\ -1 & -2 & \alpha & -2 & -1 \\ & & -1 & & \end{bmatrix}$$

Where $\alpha$ = 2, 4, or 8.

Step 2: Joint shape-dependent gradient magnitude and direction could be described as:

$$\text{Magnitude } (x, y, \theta) = \text{Max}\left(\cos\theta \frac{\partial G}{\partial x}, \sin\theta \frac{\partial G}{\partial y}\right)$$

Where the gradient magnitude and direction are joined and calculated using pixels within an m×n neighborhood, where m, n=1, 2, 3 . . . .

This argument assigns the maximum value of the two functions to the magnitude at a given point, hence, reduces the magnitude value at angles with low intensity values. Note that the Canny method gradient magnitude and direction are calculated by pixels within a 2×2 neighborhood is sensitive to noise and may detect false edges. Also, a set of defined gradient kernel sets for derivative approximation can be used effectively for edge detection, line detection, and consequently for feature extraction. Such kernels are shape dependent and may vary in sizes and dimensions. A kernel size could be of n×m pixels, for example of 3×5, 5×7 or 9×5 as shown in the next kernel matrices.

$$\begin{bmatrix} 1 & \sqrt{2} & 0 & -\sqrt{2} & -1 \\ \sqrt{2} & 2 & 0 & -2 & -\sqrt{2} \\ 1 & \sqrt{2} & 0 & -\sqrt{2} & -1 \end{bmatrix}$$

$$\begin{bmatrix} 1 & \sqrt{2} & 2 & 0 & -2 & -\sqrt{2} & -1 \\ \sqrt{2} & 2 & 2\sqrt{2} & 0 & -2\sqrt{2} & -2 & -\sqrt{2} \\ 2 & 2\sqrt{2} & 4 & 0 & -4 & -2\sqrt{2} & -2 \\ \sqrt{2} & 2 & 2\sqrt{2} & 0 & -2\sqrt{2} & -2 & -\sqrt{2} \\ 1 & \sqrt{2} & 2 & 0 & -2 & -\sqrt{2} & -1 \end{bmatrix}$$

$$\begin{bmatrix} 1 & \sqrt{2} & 0 & -\sqrt{2} & -1 \\ \sqrt{2} & 2 & 0 & -2 & -\sqrt{2} \\ 2 & 2\sqrt{2} & 0 & -2\sqrt{2} & -2 \\ 2\sqrt{2} & 4 & 0 & -4 & -2\sqrt{2} \\ 4 & 4\sqrt{2} & 0 & -4\sqrt{2} & -4 \\ 2\sqrt{2} & 4 & 0 & -4 & -2\sqrt{2} \\ 2 & 2\sqrt{2} & 0 & -2\sqrt{2} & -2 \\ \sqrt{2} & 2 & 0 & -2 & -\sqrt{2} \\ 1 & \sqrt{2} & 0 & -\sqrt{2} & -1 \end{bmatrix}$$

Figure 3:
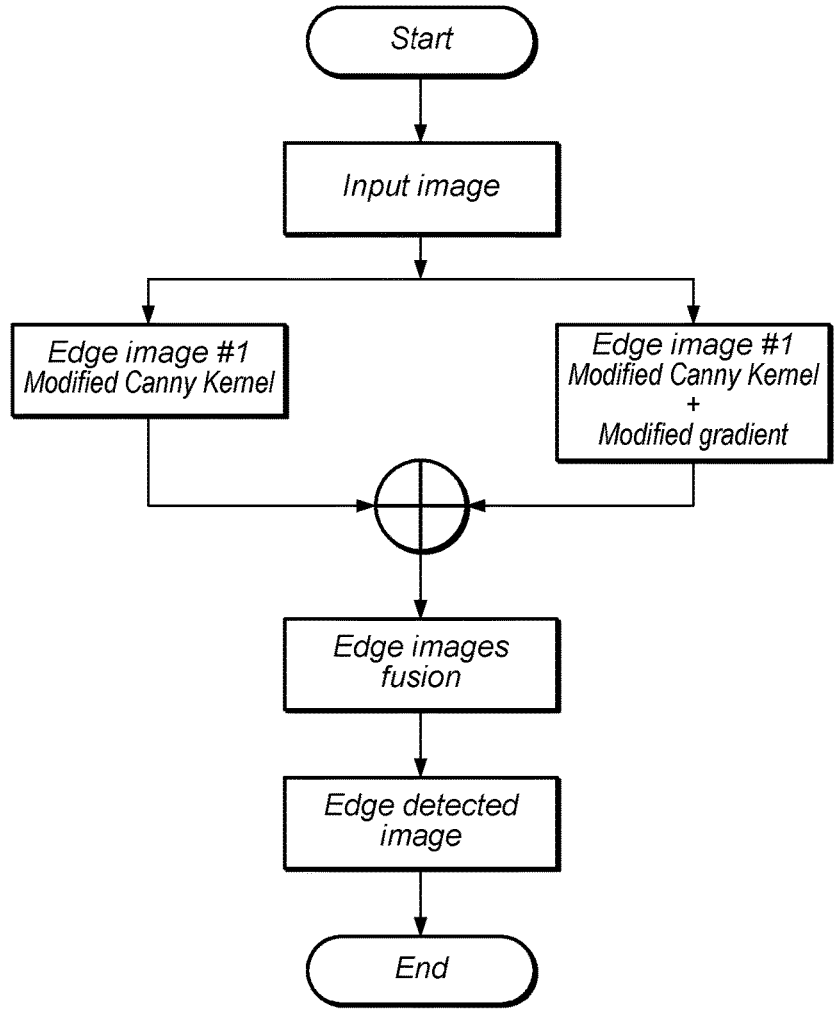
FIG. 3 is an illustration of the concept for fusion of edge detected images.

Step 3: Fusion of edge images. Conventional Canny algorithm uses a method of non-maximum suppression (NMS) to process the smoothed image and make sure each edge is of one-pixel width. In this method, a fusion of two edge detection techniques is proposed. The first edge-detected image contains the modified kernel set. The second edge-detected image contains the same kernel set mentioned previously in addition to using the modified gradient magnitude. The fusion of the two edges would guarantee the existence of all edges that one image may miss over the other one. FIG. 3 shows the proposed fusion concept.

There are several algorithms that are developed for edges fusion. Considering medical images, the criteria for selecting the fusion operator of interest must preserve edge information in both images as well as noise detection avoidance. Hence, the average energy fusion method proposed may be utilized. For two edge images $G_L$ and $G_H$, the fused edge image $G_F$ can be defined as:

$$G_{F,i} = \omega_L G_{L,i} + \omega_H G_{H,i}$$

Where $G_{L,i}$ is the grey-level value at a given pixel location Pi in the edge image $G_L$, $G_{H,i}$ is the grey-level value at a given pixel location Pi in the edge image $G_H$. The average value of the corresponding coefficients in each edge image $\omega$ is defined as:

$$\omega = \frac{E_i}{E_L + E_H}$$

Where $E_L$ and $E_H$ represent the low frequency and high frequency energy of edge image respectively. Such an average value can judge on the contents of the fused image, and can reduce the unnecessary details that are contained on one edge image over the other. On the other hand, the energy $E_i$ contained in an image at a pixel location $P_j$ can be defined as:

$$E_i = \frac{\sum_{j=1}^{N} P_j}{N}$$

Figure 4:
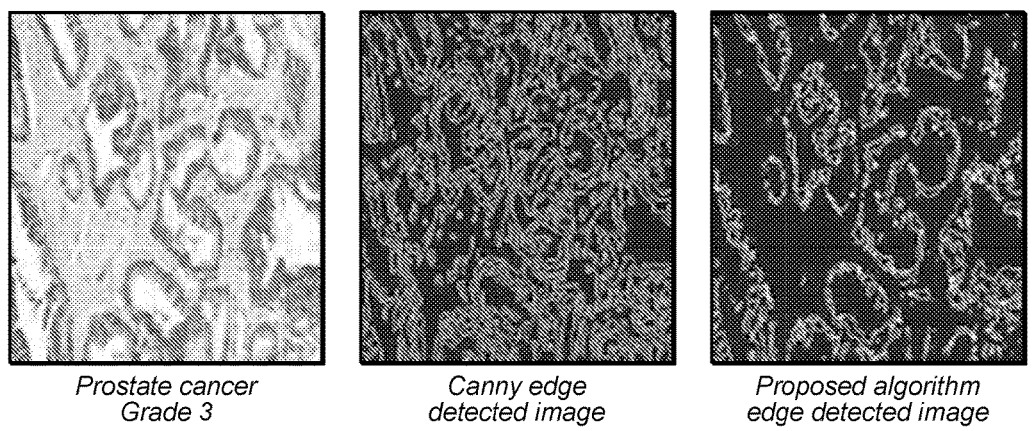
FIG. 4 is a comparison of the results between one Canny edge detected image and the output of the proposed edge detection algorithm.

Application to prostate cancer biopsy images: the algorithm is simulated on a biopsy image having prostate cancer of Gleason grad 3. FIG. 4 illustrates simulation results of the algorithm and shows how the proposed edge detection algorithm succeeds in detecting edges more precisely compared to canny edge detector.

As mentioned previously, one might consider integrating a proper enhancement algorithm as a preprocessing stage for a better visualization and hence, an effective detection of different edge details.

This combination succeeds in providing useful information about objects and structural information as well as an enhanced visualization when variation of a constant parameter a is considered. In this algorithm, Logarithmic "log" functions replace the morphological filters operation. That is, the deployment of PLIP model while the maximum ratio of horizontal adjacent gray level values is investigated. The new rational expression becomes:

$$Rx(i, j) = \max\left(\log\frac{(I(i,j))^\alpha}{(I(i,j-1))^\alpha}, \log\frac{(I(i,j))^\alpha}{(I(i,j+1))^\alpha}\right)$$

Applying PLIP gray tone function on the row ratio $R_x$ yields:

$$gx(i, j) = \max\left(\log\frac{\text{int}(\alpha f_3)\text{int}(\alpha f_6^2)\text{int}(\alpha f_9)}{\text{int}(\alpha f_1)\text{int}(\alpha f_4^2)\text{int}(\alpha f_7)}, \log\frac{\text{int}(\alpha f_1)\text{int}(\alpha f_4^2)\text{int}(\alpha f_7)}{\text{int}(\alpha f_3)\text{int}(\alpha f_6^2)\text{int}(\alpha f_9)}\right)$$

Where $f$ denotes pixels in gray tone; int is the integer operation; $\alpha$ is a predefined constant.

Similarly, the column ratio becomes:

$$gy(i, j) = \max\left(\log\frac{\text{int}(\alpha f_1)\text{int}(\alpha f_2^2)\text{int}(\alpha f_3)}{\text{int}(\alpha f_7)\text{int}(\alpha f_8^2)\text{int}(\alpha f_9)}, \log\frac{\text{int}(\alpha f_7)\text{int}(\alpha f_8^2)\text{int}(\alpha f_9)}{\text{int}(\alpha f_1)\text{int}(\alpha f_2^2)\text{int}(\alpha f_3)}\right)$$

In order to utilize the above expressions to compute the magnitude in LIP edge detection, the isomorphic transformation is applied to have the magnitude components gx and gy. An enhanced magnitude computation considers the maximum horizontal and vertical ratios as follows:

$$\text{Magnitude} = M\left(1 - \exp\left(-\max\left(\frac{\overline{gx}}{M}, \frac{\overline{gy}}{M}\right)\right)\right)$$

Different images were tested in order to verify the functionality of the introduced algorithm. Images range from medical images to images of other objects where a different parameter a is selected for each image. The introduced algorithm succeeds in detecting the objects of interest only by eliminating other unwanted objects that belong to different gray tone levels. Also, it has the ability to detect unforeseen edges that no other edge detection algorithm can detect due to the very slight level of intensity variations. Furthermore, it serves as a tracking application to track the development of certain gray level in certain areas.

Most of the traditional edge detection algorithms share one objective which is to detect accurate and more edge details. In an embodiment, the previous algorithms are utilized in image filtering process. Noisy communication channels and sensors may contribute to the existence of impulsive noise in images. Such images corruption can be eliminated by implementing image filtering algorithms. Various image filtering techniques have been introduced but median-based filters have proven to attract much attention due to their ability in preserving edge details as well as simplicity in removing impulsive noise.

The following steps summarize the process of image filtering based on edge detection technique: (1) Edge detection processing where edge detection operator could be any edge detection algorithm or one of these described previously in this embodiment including shape dependent edge detection, Noise-resilient edge detection algorithm for brain MRI images, or logarithmic-ratio based edge detection. (2) Locate edge pixels coordinates in order to avoid such edges during image filtering. (3) Map coordinates to the original/noisy image in order to save gray level intensity values at these locations. (4) Detect the existence of impulsive noise on edges. Detection is based on a rapid change of intensity values between two adjacent pixels. (5) Apply switching filter algorithm for image filtering. One filter is a filter of different sizes m×n, e.g. 3×3, 5×5, 7×7 among others square and rectangular kernels, which is applied depending on impulsive noise density. The second filter operates on noisy edges which is weighted filter with less weight at the centers of the impulsive noise locations. Switching occurs only whenever impulsive noise is detected on edges at locations determined at step (4) previously.

Simulation results of applying the previous algorithm on different images were studied. Prior to implementing the developed algorithm, impulsive noise with different densities is added to the image. The simulation results show a superior performance of the developed algorithm in terms of preserving edge details while filtering the impulsive noise.

In conclusion, an edge preservation filtering technique may be used for image analysis. The idea behind such a concept is to avoid blurring edges during the filtering of the images, and hence, avoiding missing some significant branched edges, especially in medical application, e.g. biopsy tissue images. Simulation results showed a superior performance in edge preservation compared to other filtered images where edges appear to be blurry.

Visual Rational Morphological Filters for Image Enhancement and Edge Detection

Considering image contrast enhancement, there are various methods for image enhancement that operate globally on an image such as histogram equalization, gamma correction, logarithmic compression, alpha-rooting, and level or curve-type methods. The drawback of these algorithms is that they are not always adaptive and in general, they do not take into consideration local statistical variations within an image. Also, they do not match the larger dynamic range the human visual system opposes. Hence, the need to utilize an image enhancement algorithm where pixels are processed in local neighborhoods is mandatory.

An Edge-Preserving Contrast Enhancement (EPCE) is developed based on dynamic range compression. The enhancement part of this algorithm is based on local mean at each pixel as follows:

$$I(x, y) = \frac{2}{1 + e^{-2\tau(x,y)/\lambda(x,y)}} - 1$$

Where I(x,y) is the output image, τ(x,y) is either the V component of the image in HVS color space or the gray level, and λ(x,y) provides a measure of the local statistic at a given window for the adjustment of the transfer function to the local mean and given by:

$$\lambda(x, y) = C + (M - C)\left(\frac{\mu(x, y)}{M(Qx + N)}\right)$$

Where C is an enhancement parameter in the range 0≤C<255, M is the maximum value in that range, Q and N are arbitrary constants. This enhancement algorithm functions in an adaptive manner by enhancing dark area of the image while the light area is preserved. In order to enhance edges where a significant gray level discontinuity exists, the ratio of difference of gray levels is investigated locally to calculate the ratio magnitude R. An illustrative example is shown for a 3×3 neighborhood as follows:

| I(i−1, j−1) | I(i−1, j) | I(i−1, j+1) |
|---|---|---|
| I(i, j−1) | I(i, j) | I(i, j+1) |
| I(i+1, j−1) | I(i+1, j) | I(i+1, j+1) |

$$Rx(i, j) = \max\left(\frac{I(i, j)}{I(i, j-1)}, \frac{I(i, j)}{I(i, j+1)}\right),$$

$$Ry(i, j) = \max\left(\frac{I(i, j)}{I(i-1, j)}, \frac{I(i, j)}{I(i+1, j)}\right)$$

$$R(i, j) = \sqrt{Rx(i, j)^2 + Ry(i, j)^2}$$

The above expression is used to emboss edges details and to yield a new and adaptive dynamic range enhancement as follows:

$$Ien_{(i,j)} = \frac{\alpha(R(i, j))}{1 + e^{-2\tau(i,j)/\lambda(i,j)}} - 1$$

Where $Ien_{(i,j)}$ is the enhanced pixel, R(i,j) is the ratio coefficient, α is an arbitrary function operating according to the value of R. The proposed formula succeeds in enhancing and highlighting edges where gray levels transitions are significant.

Recall from the log-ratio approach for morphological filters. The effect of such ratio is to give more weight to edges of interest that need to be enhanced to the highest dynamic range of the HVS based on the local statistics as follows:

$$I_{ed}(i, j) = \beta\left(\log\frac{\tau(i, j)}{F(i, j)}\right)I_{en}(i, j)$$

Where β is a normalization coefficient controlling the enhancement saturation level and acting as a primary edge detection threshold, F(i,j) is local a filtering operation based on local neighborhood statistics. A further threshold stage is introduced as an adaptive process to reflect local statistics by deploying standard deviation in local windows. Several thresholds may be used. Particularly, we use a threshold T(i, j) for illustrative purpose which is calculated as follows [16]:

$$T(i,j) = \alpha \cdot tm(i,j) + C \cdot \sigma(i,j^{20})$$

Where α·tm(i,j) is the local alpha-trimmed mean, C is a global constant, and σ(i,j) is the standard deviation. Once potential edge gray levels are detected, binarization process takes place. A summary of the developed algorithm is provided in the table below:

| Process | Algorithm |
|---|---|
| Pre-processing | Gaussian/Median/Order-statistics filtering |
| Ratio magnitude calculation | $R(i, j) = \sqrt{Rx(i, j)^2 + Ry(i, j)^2}$ |
| Adaptive enhancement | $I_{en}(i, j) = \frac{\alpha(R(i, j))}{1 + e^{-2\tau(i,j)/\lambda(i,j)}} - 1$ |
| HVS-based edge detection | $I_{ed}(i, j) = \beta\left(\log\frac{\tau(i, j)}{F(i, j)}\right)I_{en}(i, j)$ |
| Threshold T | Adaptive thresolding<br>Example: $T(i, j) = \alpha \cdot tm(i, j) + C \cdot \sigma(i, j)$ |
| Binarization | $I_{ed}(i, j) = \begin{cases} 1 \to I_{ed}(i, j) \geq T \\ 0 \to \text{elsewhere} \end{cases}$ |

The architecture and characteristics of dark nuclei is an essential feature in deciding the grade of cancer besides other glandular features. In this case, the proposed algorithm operates on the image and succeeds to segment dark nuclei. This result can be used as an input to feed classification systems of interest such as fractal analysis based classifier for features extraction.

In this embodiment, we also present an algorithm for visualizing edges in colored images as well as edge detection using the previously developed logarithmic ratio approach. The developed visualization algorithm has a superior performance in highlighting more unforeseen color edges than the standard color-grayscale conversion method can present. Also, by integrating the proposed algorithm with a logarithmic-ratio based edge detector operator, the developed algorithm outperforms the standard edge detection operators in gradient colored images where color boundaries transitions are hard to detect.

Most of edge detection operators operate on grayscale images since color image components impose some sort of complexities in detecting edges. In grayscale images, an edge can be detected by investigating the discontinuity in gray levels. However, in color images there are no clear and defined color edges although color images carry more information and therefore have the potential of having more hidden and accurate edges. The limitation factor in detecting all the edges in gray levels images is due to the fact that different colors have different hue values but they share the same intensity value. Hence, an effective approach to convert color components from several color models such as RGB components into gray level scale is needed.

Considering color space, there are different representations of three dimensional color spaces having different characteristics. One set of color spaces uses Cartesian coordinates for point's representation in space. Examples of this type of sets are the three primary illumination colors Red, Green, and Blue (RGB), the complementary colors Cyan, Magenta, and yellow (CMY), and the opponent color representation luminance, in-phase and quadrature (YIQ).

Another space representation utilizes polar/cylindrical coordinates such as Hue, Saturation, and Lightness (HSL) and Hue, Saturation and Value (HSV). Generally, each color space can be converted to another color space representation.

For color images edge detection, previous researches in this area utilized vector order statistics, distribution of pixel colors and fusion techniques of edges detected at different color spaces. Hence, more focus was given to analyzing and extracting color information rather than investigating new edge detection operators.

Considering real world images, one might consider the precision of edge maps as a result of human visual system (HVS) perception. One of the well-known image processing frameworks that incorporate the characteristics of HVS in image enhancement as well as edge detection is the Parameterized Logarithmic Image processing (PLIP) model. In PLIP model, a new set of arithmetic operations are introduced taking into consideration the characteristics of human visual system.

Furthermore, the concept of utilizing ratio operations in morphological filters design that oppose some characteristics of HVS was introduced. In previous embodiment, the logarithmic image processing framework and the concept of rational filters design were integrated to produce a new edge detection algorithm based on HVS model. The proposed method provided a new approach in edge detection focusing on the class of images where the variations and discontinuities in gray levels follow a gradient pattern. In this embodiment, we introduce an algorithm for visualizing unforeseen edges represented by any color model. An example is presented taking the representation of an image in RGB color space.

RGB color model consists of three independent color planes representing the three chromaticity components: Red, Green, and Blue. In order to specify a pixel RGB value, each color component is specified independently within the range 0 to 255. RGB color model is used in many applications such as computers, television, and electronic systems. Conversion of RGB color space to grayscale is the common preprocessing step prior to applying edge detection. The concept of converting RGB to grayscale depends on assigning weight for each color component based on HVS and its perception of colors. The common weighting vector used is [L, M, N], where L+M+N=1.

Some of the common edge detection techniques for color images utilize fusion technique of edges detected at different color space using traditional edge detectors. The first fusion method finds the gradient and the edge map at each of the three RGB levels, then fuses the resultant edge maps output. The second method fuses the gradients at each RGB component, and then finds the edge map of the final fused gradient.

The developed algorithm focuses on extracting edge details that cannot be highlighted for detection using the standard assigned HVS vector weight. To illustrate the operation of the algorithm, the RGB color model is considered. Given a tri-chromatic color image, one might consider designing a rational morphological filter that takes into consideration the assigned HVS weight for each component in tri-chromatic space. For instance, for a RGB image let and Fn and Fm represent two different filters as follows:

$Fn=(L*R,M*G,N*B)$ $Fm=[\beta R \log^{\alpha R}(L*R), \beta G \log^{\alpha G}(M*G), \beta B \log^{\alpha B}(N*B)];$ $[\beta R \log^{\alpha R}(w_1R-w_2G), \beta R \log^{\alpha R}(w_1R-w_2B)];$ $[\beta G \log^{\alpha G}(w_2G-w_1R), \beta G \log^{\alpha G}(w_2G-w_3B)];$ $[\beta B \log^{\alpha B}(w_2B-w_1R), \beta B \log^{\alpha B}(w_2B-w_3G)];$ Where $\beta$ and $\alpha$ are constants assigned to each color component, $w_1$, $w_2$, $w_3$ represent different assigned weight for R,G,B color components respectively. The ratio of different morphological operations may take any of the following forms:

$$\beta 1\left(\frac{\max(Fn)}{\max(Fm)}\right); \beta 2\left(\frac{\min(Fn)}{\max(Fm)}\right); \beta 3\left(\frac{\min(Fn)}{\min(Fm)}\right); \beta 4\left(\frac{\max(Fn)}{\min(Fm)}\right);$$

where $\beta$ is normalization constant

The above expressions yield successful results in investigating the intensity of each RGB component at each pixel taking into consideration the HVS perception characteristics. The result of carrying out these different operations produces a gray level image having more edge details than the standard translation of RGB to grayscale.

Image processing algorithms presented herein highlight and visualize different information that can be obtained from variety of images including biopsy images as well as real world images. The developed preprocessing algorithms succeed in detecting, segmenting and visualizing different image details compared to the state of the art current image processing algorithms.

Method for Carcinomas Color Region Mapping

Referring now to another embodiment of the invention, a method for finding carcinomas dominant colors is provided. The goal of this method is to reduce the number of distinct colors or define the most populated color in the biopsy image. The resulting quantized image should be as visually similar as possible to the original image for the further tissue structure objects segmentation. For example we may map a biopsy image containing millions of colors into an image containing a few colors, which are closely tied to tissue structures in H&E stained needle biopsy images are also included in the color map. Additional colors of interest can be added manually to keep information for further studies.

Before performing color region mapping, color standarization in digital histopathology images is performed. Various algorithms me be used to make the appearance of the image similar to those in the training database and tackle the problem of color constancy. Examples of color normalization algorithm include: Reinhard's method and its modifications [18], color deconvolution, histogram matching, among others.

The general algorithm for constructing color region mapping comprises the following steps: (1) Survey the colors which compose biopsy images. (2) Determine the 'best' set of colors for a biopsy image by using algorithms for localization of local maxima in 2-D color histograms. (3) Generate color table. (4) Assign each color to a class for segmentation purposes. (5) Map images into the reduced color space.

For instance, to construct the color region mapping shown in the following table, instead of adopting an absolute set of color features for our segmentation algorithm, the 2-D projections of 3-D RGB color model of a large variety of prostate needle biopsy images of different grades are computed to construct 2-D histograms and generate a good approximation of color region distribution in those images. This is an important step since the variations in colors of stained images constitute an aspect to take into account before applying segmentation procedures based on their color composition, since these variations are always present even if there are defined laboratory controls and protocols to prepare tissue core samples. Based on the calculated 2-D histograms, a color region mapping is proposed taking the colors that appear more frequently in our image set and that represent any object of interest in the evaluation of histopatholy images.

In more detail, still referring to the carcinomas color region mapping method, the most prominent colors may found by using an automatic algorithm for local maxima location in 3-D surfaces.

The procedure explained above is valid for finding representative colors of any image dataset. In this embodiment, the resulting region mapping for prostate cancerous class of test images is presented in the FIG. 29.

It is important to note that any color model can be used to apply the above method. In this case, color model transformation must be performed before constructing 2-D projections.

This embodiment also provides a method for tissue structure segmentation. Segmentation procedure is carried out through pixel classification. This automatic process consists of minimizing the distance between each pixel and the colors considered in the color map, and assigning to each pixel the class corresponding to the nearest color. To classify a pixel, an appropriate distance metric may be used. As an example Euclidean distance is:

$$d_i(m,n) = \sqrt{(r_{(m,n)} \beta r_i)^2 + (g_{(m,n)} - g_i)^2 + (b_{(m,n)} - b_i)^2}$$

Figure 5:
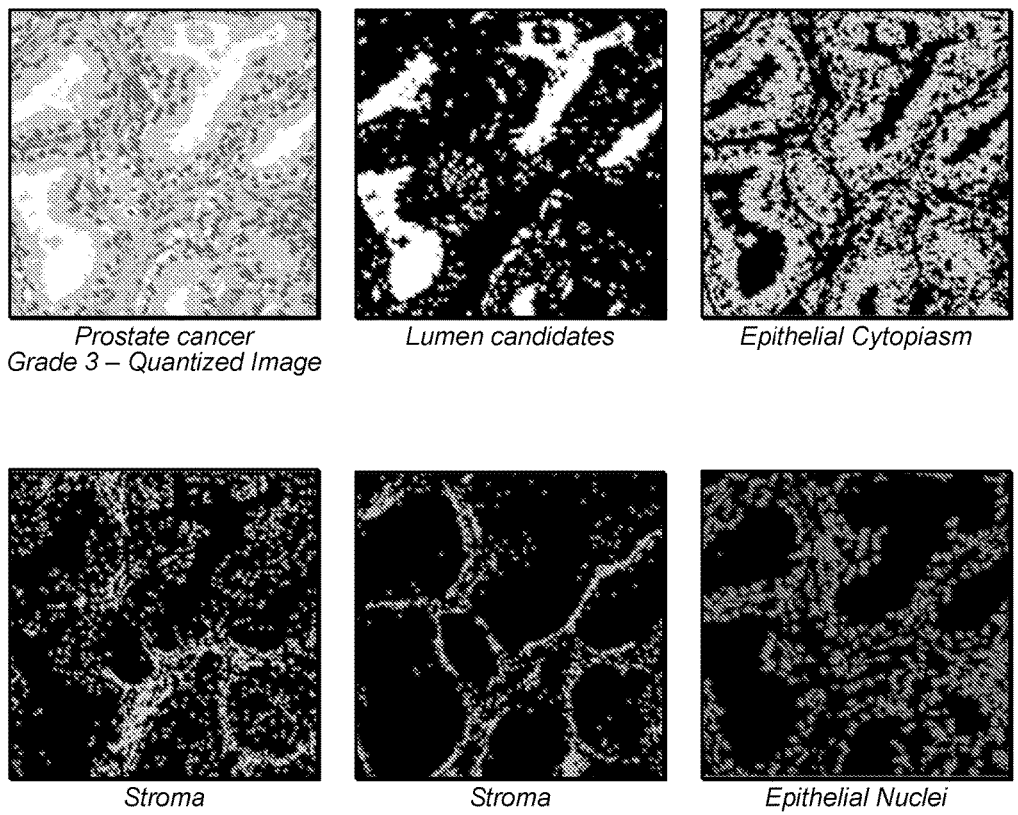
FIG. 5 is an example of results of tissue structure segmentation using color region mapping in prostate cancer biopsy.
Figure 6:
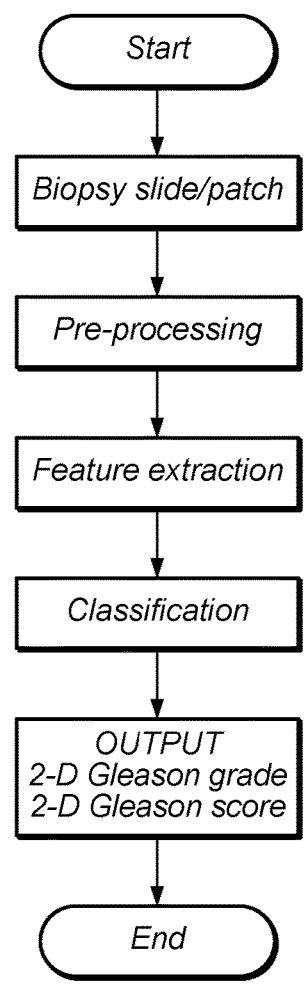
FIG. 6 shows an exemplary flow diagram of 2-D Gleason grading systems.

In the equation above $d_i(m,n)$ is the distance in RGB color model from pixel (m,n) to the i'th color region defined in the color map table. FIG. 5 shows the structure segmentation results based on color information of an image that belongs to prostate cancer, Gleason grade 3 pattern.

Method for Pattern Detection

The novel Gleason grading concept exploits the ability of an optimal predictor/compressor to compress (in an informational sense) its predicting class optimally. In this embodiment, an implementer selects an appropriate machine learning technique and an appropriate prediction technique (which may be one in the same) to train a set of predictors on images or pre-processed images containing a plurality specific Gleason pattern grade. By pre-processed we imply that operations may have been performed on the image (such as architectural segmentation/classification, textural segmentation/classification, feature segmentation/classification, denoising, scaling, etc.) prior to predictor training. Subsequent use of the word "image" with regard to predictors refers to an image that has already been appropriately pre-processed.

Each predictor should be trained on a specific type of Gleason pattern. Possible techniques include: maximum likelihood estimation, Bayesian estimation, Kalman filtering, prediction by partial matching, context tree weighting, and others. Paired with an appropriate entropy encoder, each predictor/encoder pair forms the best compressor for its respective pattern type compared to the other predictor/encoder pairs. Hereafter, predictor/encoder pairs shall be referred to as pattern compressors (PCs) for simplification. Scoring of a biopsy sample image (hereafter referred to as the query or query image) amounts to compressing each query pixel with each PC. Smaller compressed sizes per pixel imply more significant membership to the pattern class of a PC. Selection, combination, or other analysis of the all PC compression rates can then be used to estimate the grade of a particular pixel or the query image on a whole.

As an exemplifying embodiment, universal detector/classifiers (UDCs) constructed from a variable order Markov model which utilizes a prediction by partial matching (PPM) algorithm for prediction and an arithmetic encoder for compression can be used as PCs. Each UDC trains on a given Gleason pattern type such that each is the best UDC data compressor of that pattern type on average. Grading of a query sample involves selection, combination, or other analysis of the classifier's relative compression performance. Optionally, a PC optimized to the query image can be used for comparison purposes.

Method for Hard Gleason Scoring & Mapping

Figure 23:
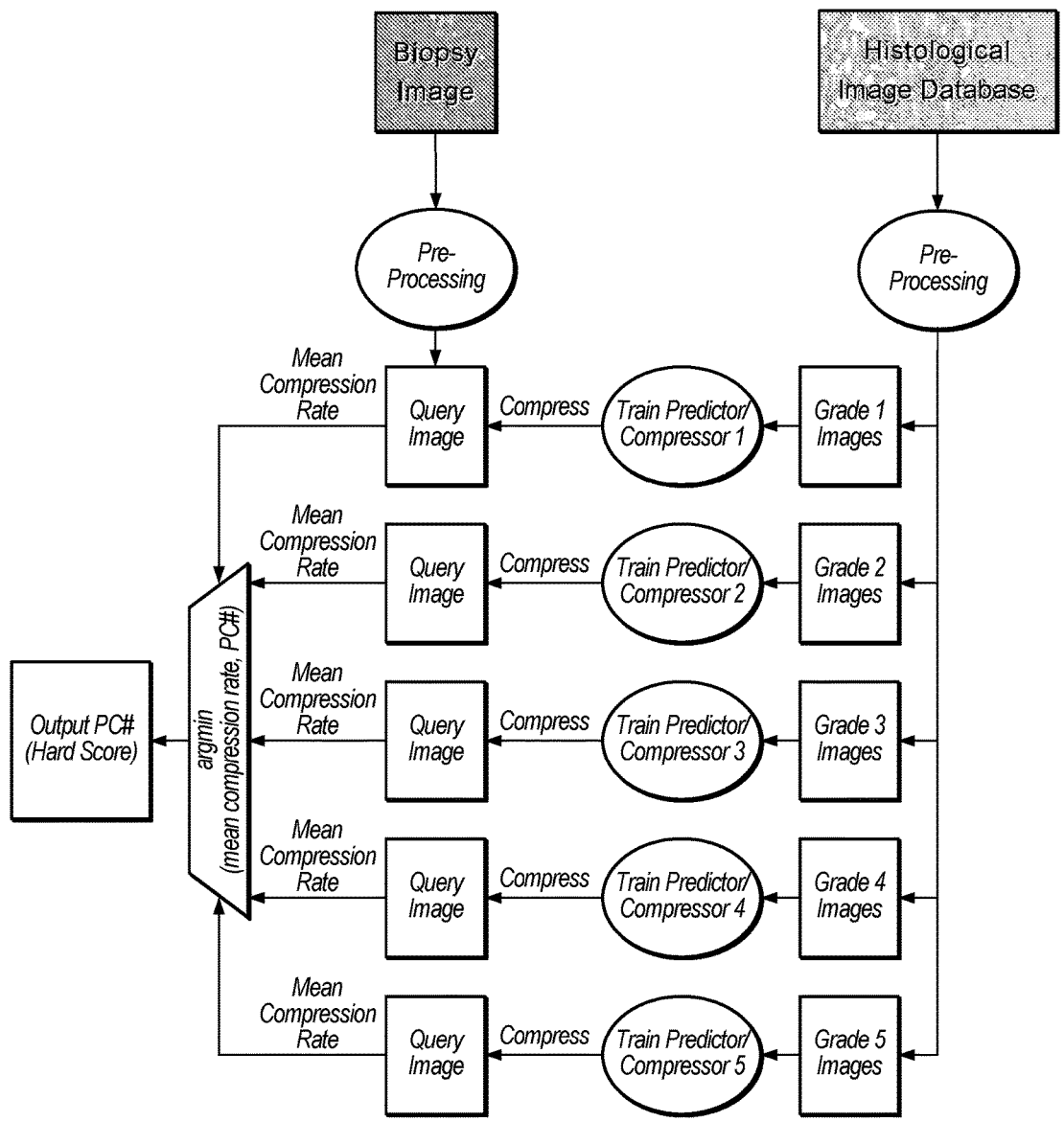
FIG. 23 shows exemplary steps for computation of a "Hard Gleason grade"

A "Hard Score" may be assigned to a biopsy image to directly correspond to the single most-likely pattern observed within a query image. This is analogous to a pathologist's choice of grade, where a hard decision must be made between possible Gleason grades. This is achieved by choosing the predictor/encoder pair which best compresses a query image on average. The hard score of the sample is the grade of the pattern for which the predictor/encoder pair was optimized (see FIG. 23).

Figure 24:
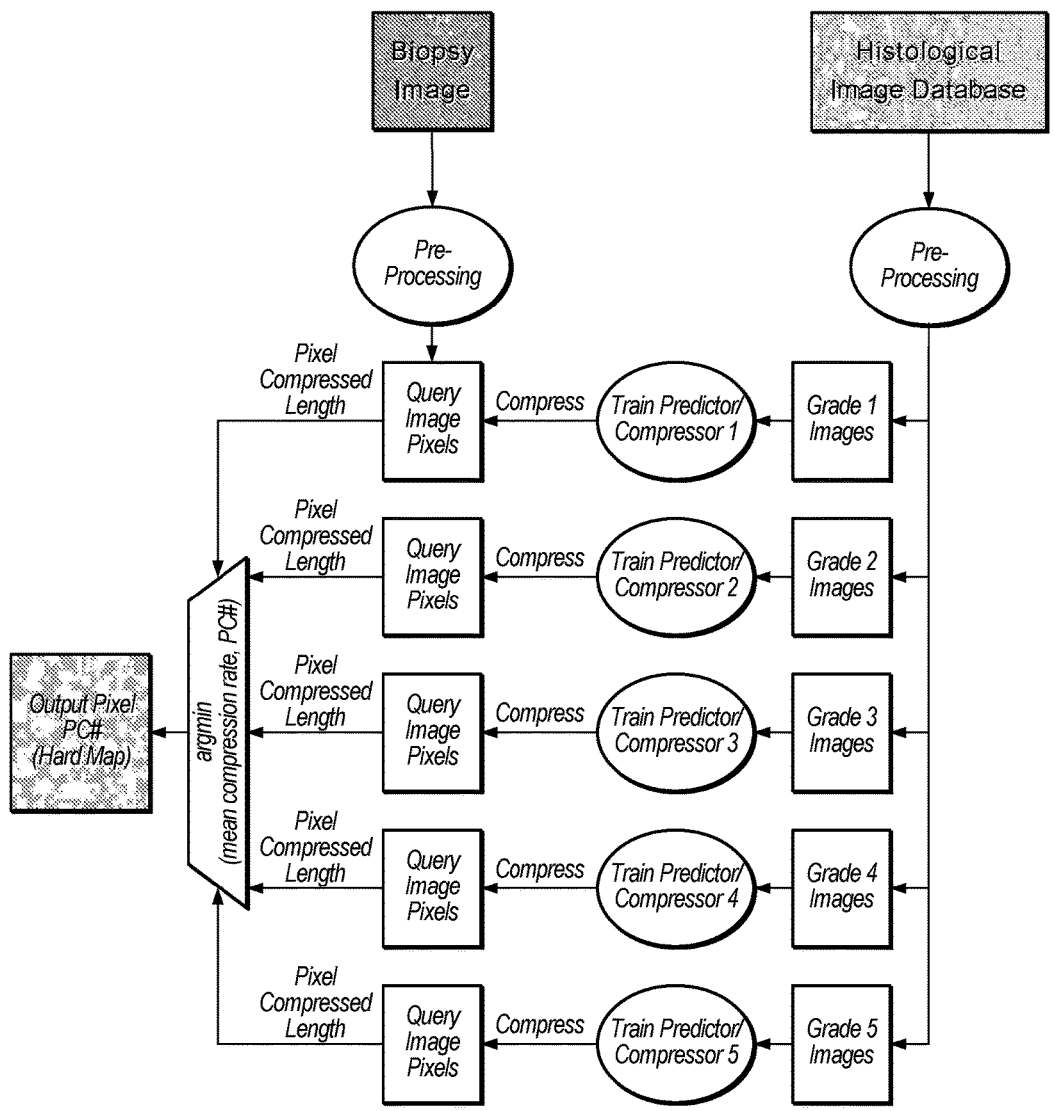
FIG. 24 shows exemplary steps for computation of a "Soft Gleason grade"
Figure 25:
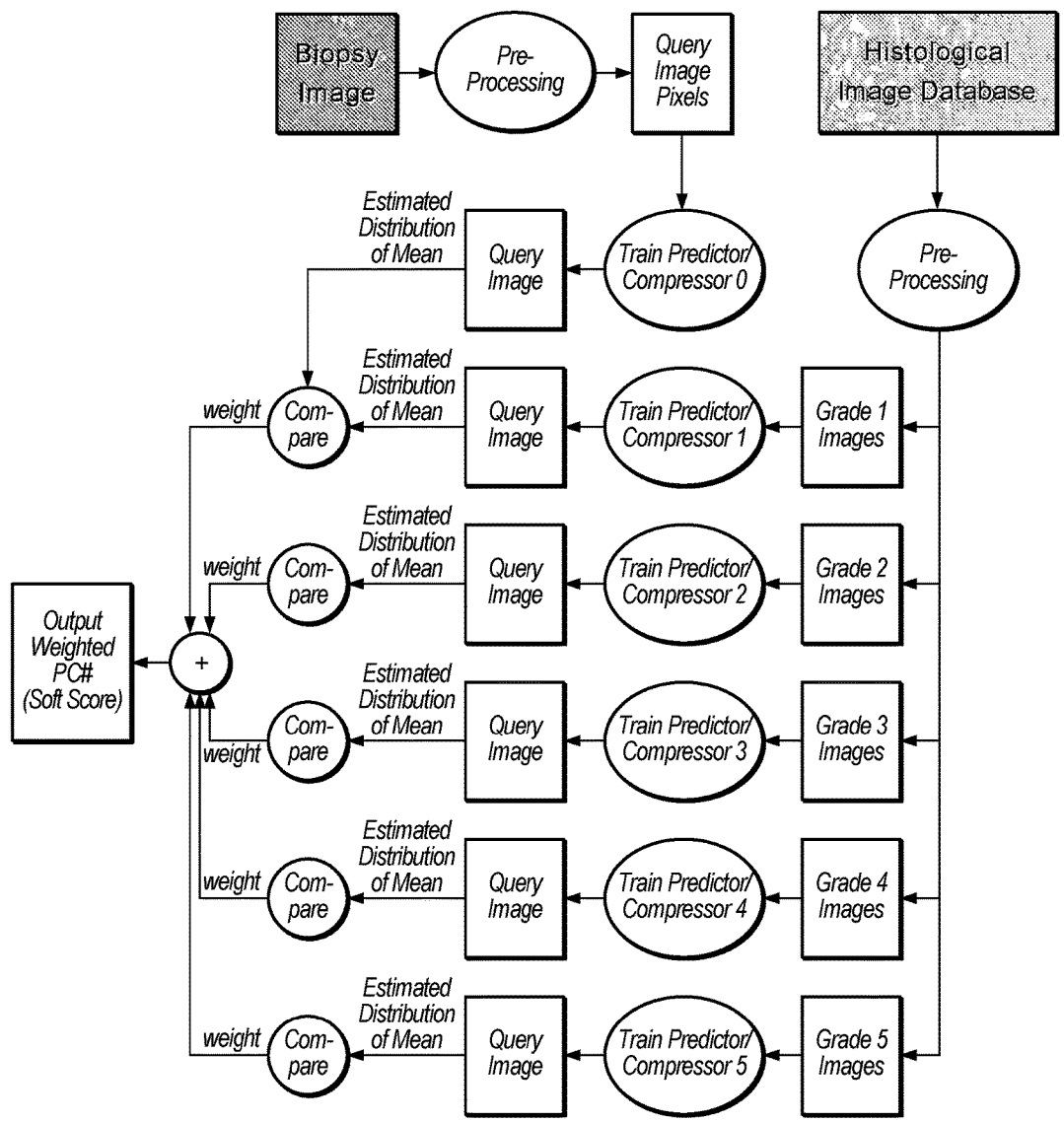
FIG. 25 shows exemplary steps for computation of a "Hard Gleason map"
Figure 26:
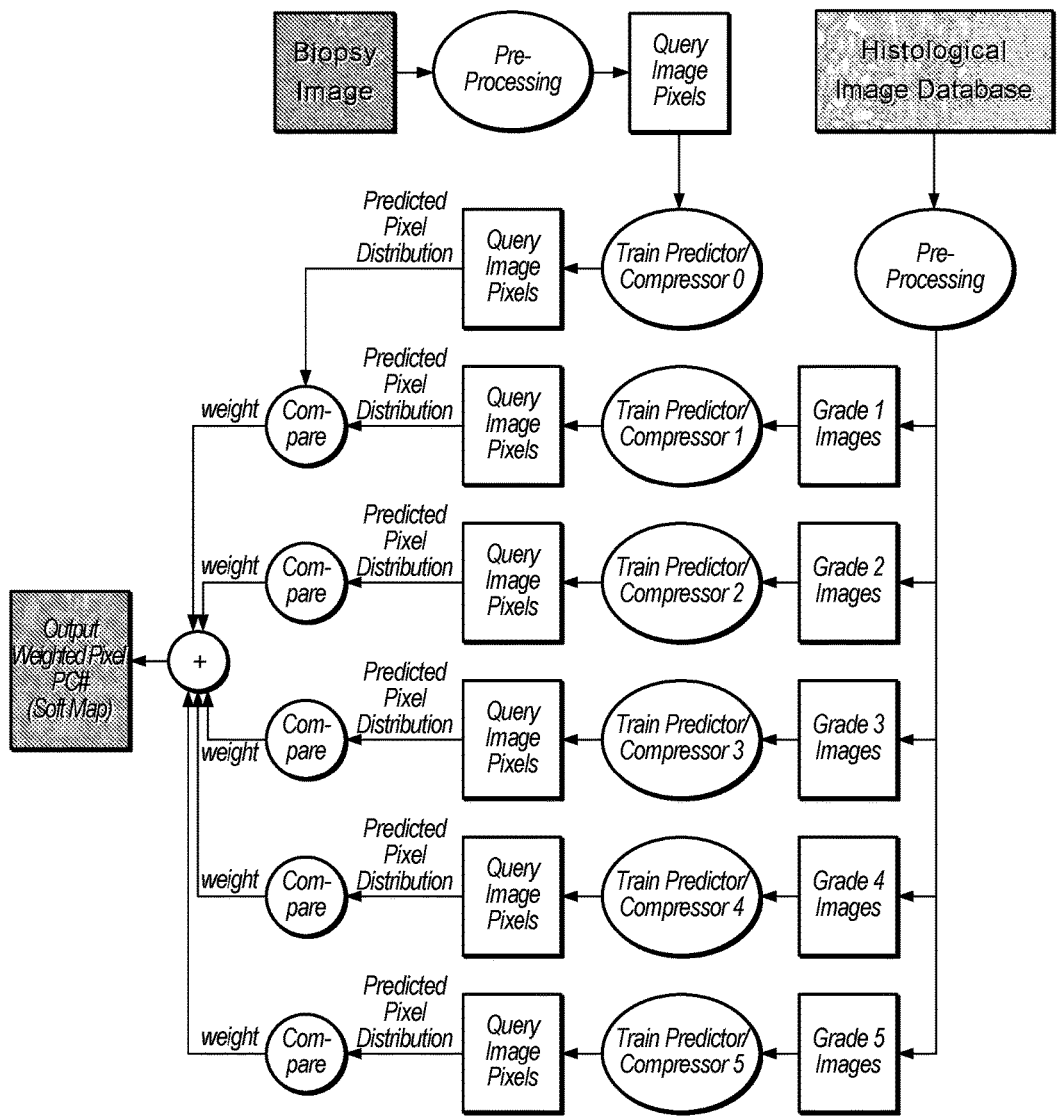
FIG. 26 shows exemplary steps for computation of a "Soft Gleason map"

The same hard grading method may be used on a pixel by pixel basis, assigning a hard Gleason grade to each pixel individually depending on which trained UDC compresses it best. This results in a map of pixel grades which can distinguish between regions of different Gleason patterns within a single biopsy image (see FIG. 24). It should be noted that the average hard map grade is not necessarily equal to the hard grade as determined above. For instance, if patterns 3 and 5 are both prevalent within a query image, then the average hard score is likely to be near 4 despite grade 4 Gleason patterns being absent within the image. The hard score, however, will be 3 or 4 depending on which pattern is most prevalent.

Method for Soft Gleason Scoring & Mapping

A biopsy image may also be assigned a "Soft Score," here denoted s. A soft score can better characterize a biopsy image which is a member to some extent of one or more predictor/encoder pair classes. One way to generate such a score is to assign membership values, or weights $w_g$, to each possible class found within an image and to compute the weighted mean. Thus, the score is a weighted combination of all Gleason grades where the grades $G_i$ range from 1 to 5 and the weights $w_i$ are determined from a query image:

$$s = w_1 \times G_1 \oplus w_2 \times G_2 \oplus w_3 \times G_3 \oplus w_4 \times G_4 \oplus w_5 \times G_5$$

In the above equation, the x symbol indicates a scaling operation defining how much of each pattern grade is within a given sample. $\oplus$ is a generalized combination operator defining how the weighted grades should by joined into one, global Gleason score. Other embodiments may include, but are not constrained to:

$$s = {}^{w_1+w_2+w_3+w_4+w_5}\sqrt{G_1^{w_1} G_2^{w_2} G_3^{w_3} G_4^{w_4} G_5^{w_5}}$$

$$s = \frac{w_1 + w_2 + w_3 + w_4 + w_5}{\frac{w_1}{G_1} + \frac{w_2}{G_2} + \frac{w_3}{G_3} + \frac{w_4}{G_4} + \frac{w_5}{G_5}}$$

$$s = \arg\max(w_g, G_g), g = 1, 2, 3, 4, 5$$

$$s = \arg\min(w_g, G_g), g = 1, 2, 3, 4, 5$$

$$s = PLIP(w_1 \times G_1) + PLIP(w_2 \times G_2) +$$
$$PLIP(w_3 \times G_3) + PLIP(w_4 \times G_4) + PLIP(w_5 \times G_5)$$

One embodiment is the form the above equation takes by using standard multiplication as the scaling operation and addition as the combination operation. The equation then becomes linear combination of pattern grades:

$$s = \frac{w_1 \times G_1 + w_2 \times G_2 + w_3 \times G_3 + w_4 \times G_4 + w_5 \times G_5}{w_1 + w_2 + w_3 + w_4 + w_5}$$

While traditional binary and tertiary scores prove a score that is the sum of the weighted grades, the above equation normalizes the score by the sum of the weights to ensure that the final measure is a score ranging continuously between 1 and 5.

The relation to the traditional binary Gleason score can be described as follows: the traditional binary score assigns a weight of 1 to the two most prevalent pattern grades and a weight of 0 to the three remaining pattern grades without normalizing the sum by the sum of the weights. The modified and previously-mentioned continuous-scale scores can be similarly defined through appropriate definition of the pattern weights $w_i$ and the removal of the normalization factor. The benefit of a normalized system is that it provides a continuous, threat level grade ranging from 1 to 5 in correspondence to the traditional Gleason grading system.

Often, only grades 3, 4, and 5 patterns are considered in medical practice. Thus, if we have available to us 3 predictor/encoder pairs, each optimal for a grade 3, 4, or 5 Gleason pattern, then predictor/encoder pair's respective pattern grade is scaled by its respective weight for averaging:

$$s = \frac{w_3 \times 3 + w_4 \times 4 + w_5 \times 5}{w_3 + w_4 + w_5}$$

The weights $w_3$, $w_4$, and $w_5$ are the membership values determined through statistical analysis of the compression rates $Y_{PC}$ obtained for each trained PC on a query image combined with compression rates obtained by a fourth PC, $PC_0$, trained on the query image itself. Compression by $PC_0$ generates a more optimal self-compression rate which is the amount of information the query image provides about itself.

For one embodiment utilizing analysis of variance (ANOVA) as a statistical comparison tool, confidence interval estimates $\hat{Y}_{PC}$ for the four PC mean compression rates are t-distributed around their respective measured mean compression rates, $\overline{Y}_{PC}$, parameterized by the degrees freedom in the sum squared error (which depends on both sample size and the number factor levels in question). When the sample size is large enough, the t-distributions are practically normal, centered at $\overline{Y}_{PC}$ with variance $$\sigma^2\{\hat{Y}_{UDC}\} = \frac{MSE}{n}$$

where n is the number of samples (which is just number of query image pixels) and MSE is the mean square error as determined through 4-level, single factor ANOVA testing of the four PCs' compression rates.

Figures 27, 29:
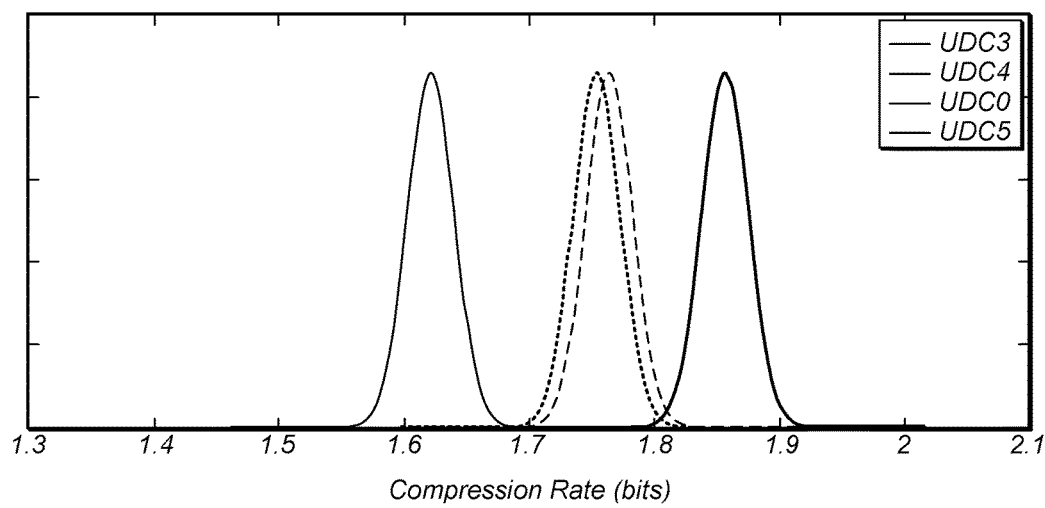
FIG. 27 shows exemplary results for computation of pattern weights used for the "Soft Gleason Score"
FIG. 29 shows region mapping for prostate cancerous class of test images.

FIG. 27 gives an example of the four PC estimate intervals as overlapping normal distributions centered at their respective mean compression rates. The total area of the intersection between the $PC_0$ distribution, $\hat{Y}_4$, and a particular Gleason pattern-trained PC distribution, $\hat{Y}_g$, is a measure of how similar the curves are to one another and therefore provides a membership value of the query image to that particular PC and can be used as a weight. For the example in FIG. 27, the amount of overlap between the compression rate estimates for PCs 3, 4, and 5 with that of $PC_0$ are 2.55e-10, 3.51e-4, and 1.23e-4, respectively. Then, the soft scores is computed:

$$s = \frac{2.55e-10 \times 3 + 3.51e-4 \times 4 + 1.23e-4 \times 5}{2.55e-10 + 3.51e-4 + 1.23e-4} = 4.26$$

A 3-level, single factor ANOVA test provides information for whether or not the three Gleason pattern-trained PCs compress the query image significantly differently. If they do not, then the soft score is unreliable and the image either belongs to all classes equally or is not likely a member of any of the classes (at least as defined by the training set). In this case, the soft grade returns "CANNOT BE CLASSIFIED" which may prompt a pathologist to manually inspect an image and possibly add it to a training set for the proper PC.

Like hard Gleason mapping, soft Gleason mapping assigns each pixel an Gleason grade dependent on the compressibility of a query image pixel I(i, j) by each PC. However, rather than selecting the best-compressing PC class, soft grading factors in the performance of all PC classes to generate an average grade. Thus, the soft grade of each pixel is a weighted mean of each Gleason class. If only grades 3, 4 and 5 are considered:

$$s_{ij} = \frac{w_{3,ij} \times 3 + w_{4,ij} \times 4 + w_{5,ij} \times 5}{w_{3,ij} + w_{4,ij} + w_{5,ij}},$$

or if a PC of each pattern class is available:

$$s_{ij} = \frac{w_{1,ij} \times 1 + w_{2,ij} \times 2 + w_{3,ij} \times 3 + w_{4,ij} \times 4 + w_{5,ij} \times 5}{w_{1,ij} + w_{2,ij} + w_{3,ij} + w_{4,ij} + w_{5,ij}}.$$

Computation of the weights $w_{g,ij}$ may differ substantially from the method used to compute the global weights $w_g$ because global image compression statistics may neither be available for nor relevant to the local grade. However, PC predictions are based on a pixel's local context and are locally applicable. In fact, a PC estimates the local likelihood function defining the probability of observing a particular pixel's value under the assumption that local the pixels are members of the PC's class. The observed likelihood models produced by each PC after observation of a pixel can be compared to the optimal likelihood function as measured by the query image's self-PC, $PC_0$, and measured as an error.

A convenient measure of error (and the error for which is used to prove universality) is the Kullback-Leibler divergence. The KL divergence measures the amount of extra bits produced using one probabilistic model instead of a more accurate probabilistic model. In this case, we compare the likelihood function for a subsequent observation generated by a PC conditioned on a specific Gleason pattern to the true likelihood function generated by the PC conditioned on the query image I after observation of pixel I(i, j). The KL divergence of $PC_g$ to $PC_0$ after pixel I(i, j) is given by $$\varepsilon_{ij}^{PC_g} = \sum_a L^{PC_0}(a \mid I(1,1) \ldots I(i,j)) \times \log_2\left(\frac{L^{PC_0}(a \mid I(1,1) \ldots I(i,j))}{L^{PC_g}(a \mid I(1,1) \ldots I(i,j))}\right)$$

where $L^{PC_k}(a|I(1,1) \ldots I(i, j))$ is the likelihood of observing the next pixel with value a conditioned on the previously observed pixel values if those pixels belong to grade g tissue and $L^{PC_a}(a|I(1,1) \ldots I(i,j))$ is the true likelihood of observing the next pixel with value a.

The smaller the error, the more likely a pixel belongs to a PC class. It is reasonable, therefore, to weight by the inverse error:

$$w_{g,ij} = \frac{1}{\varepsilon_{ij}^{PC_g}}$$

Once the weights are computed for each PC level on each pixel, then the soft map can be calculated using.

Method for Determining the Most Likely Gleason Distribution

A new method provides a measure of the uncertainty about whether a particular observed query image pixel is of one pattern grade or another. This uncertainty is here called a transition probability and represents that probability that a pixel is part of one specified pattern instead of another specified pattern. This measurement applied to every pixel within a query image then provides information about the global structure of the image—specifically, the uncertainty in the distribution (or relative population) of pixel grades within a map. Analysis of this uncertainty combined with the observed soft map distribution allows for estimation of the most likely Gleason distribution within the image, which is the amount of each grade pattern within the image.

Specifically, the percentages of dominant patterns (as determined from either hard or soft maps) along with their computed transition probabilities generate a prediction of the most probable pattern distribution within the sample.

Secondary likelihoods are given by the weight of one Gleason pattern when another is dominant. The total transition probability from the dominant pattern to the secondary pattern is the sum of the weights of the secondary pattern where the other is dominant divided by the total sum of all pattern weights where the other is dominant. Using the 3, 4, and 5 patterns only, the transition probability $T_{d \to s}$ from a dominant pattern d into secondary pattern s is then $$T_{d \to s} = \frac{\sum_{i,j} c_{d,ij} w_{s,ij}}{\sum_{g,i,j} c_{d,ij} w_{g,ij}}, \text{ where } c_{dij} = \begin{cases} 1 & w_{d,ij} > w_{g \neq d, ij} \\ 0 & \text{otherwise} \end{cases},$$

for each $d = 3, 4, 5$; $s = 3, 4, 5$; and $g = 3, 4, 5$

The transition probabilities from each pattern into another can be collected into a single transition matrix:

$$T = \begin{bmatrix} T_{3 \to 3} & T_{4 \to 3} & T_{5 \to 3} \\ T_{3 \to 4} & T_{4 \to 4} & T_{5 \to 4} \\ T_{3 \to 5} & T_{4 \to 4} & T_{5 \to 5} \end{bmatrix}$$

Define a density of states vector M(k) which contains the observable membership percentages of each pattern within a biopsy sample at iteration k. Each iteration describes a more likely distribution than the last based on the transition probabilities. If there are $n_3$ hard grade 3 pixels, $n_4$ hard grade 4 pixels, and $n_5$ hard grade 5 pixels in a query image, then the image's initial density of states is $$M(k=0) = \begin{bmatrix} \% \text{ of Grade 3 Patterns} \\ \% \text{ of Grade 4 Patterns} \\ \% \text{ of Grade 5 Patterns} \end{bmatrix} = \begin{bmatrix} \frac{n_3}{n_3 + n_4 + n_5} \\ \frac{n_4}{n_3 + n_4 + n_5} \\ \frac{n_5}{n_3 + n_4 + n_5} \end{bmatrix}$$

A prediction for the density of states at time k is given by $$M(k) = T^k M(0)$$

(if and only if the transition matrix is stationary with respect to k). If all transition probabilities are greater than zero, then T is ergodic and models an aperiodic Markov chain which has a unique, steady state solution for any initial density of states with nonzero entries:

$$M(\infty) = \overline{V}_{\lambda=1}$$

where $\overline{V}_{\lambda=1}$ is an eigenvector of T for eigenvalue $\lambda=1$ (which in this case is guaranteed to exist) with entries that sum to 1. Because the eigenvalue of the eigenvector equals 1, successive operations of the transition matrix T on $\overline{V}_{\lambda=1}$ can only yield $\overline{V}_{\lambda=1}$, which must be the most likely distribution of Gleason patterns within a sample comparable to the query image. Under these assumptions, the most likely distribution of Gleason patterns within query sample are completely characterized by observed secondary transition probabilities irrespective of the initial distribution of patterns observed within the sample.

System for Prostate Cancer Gleason Grading/Scoring Based on Morphology and Architecture of Prostatic Tissue (System 1)

Figure 7:
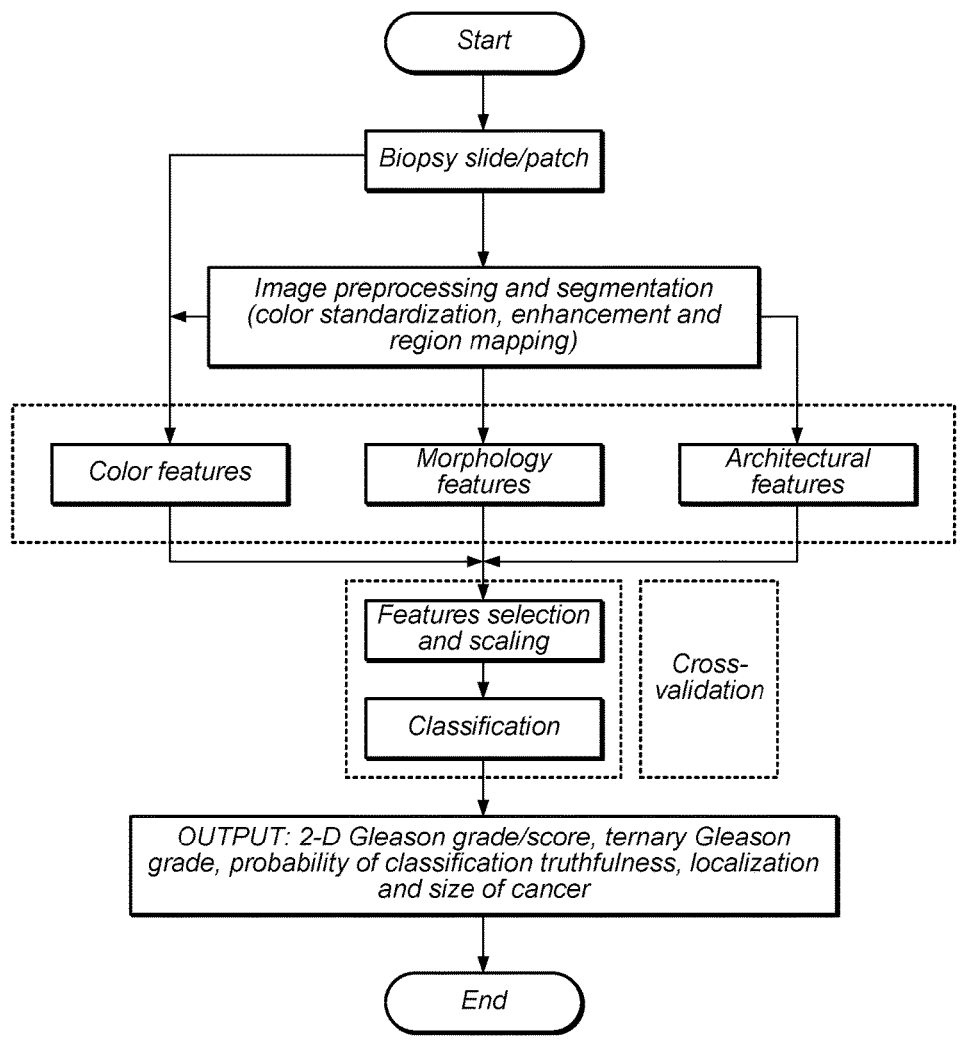
FIG. 7 shows exemplary morphology- and architectural-based Gleason grading systems.

Referring now to another embodiment of the invention, this system provides several methods including methods for tissue objects segmentation, gland reconstruction, morphology and architectural features extraction, and image classification. The proposed system proceeds into two phases: (1) the description (Color, tissue structures, gland and architectural features) that extracts the characteristics from the biopsy image pattern and (2) the classification that recognize the Gleason grades by using some characteristics derived from the first phase by implementing learning algorithms. The flow diagram of the proposed system is presented in FIG. 7.

Referring now to this embodiment of the invention in more details, the image-level features include, color information such as color distribution entropy and 2-D color histograms. To compute 2-D histograms feature vector a color model transformation may be perform. This transformation converts each RGB image into its equivalent form in a suitable color space; for instance, L*a*b or HSV (Hue, Saturation and Intensity) color models. Next, 2-D histograms are computed using n bins at each dimension. The number of bins may be selected by various heuristic methods, for example, cross-validation.

In further detail, still referring to the morphology- and architectural-based grading system, tissue structure are segmented using any suitable segmentation method, for example the color region mapping proposed in another embodiment of this invention. Having segmented tissue structure and gland units the following features may be extracted from the objects: First order statistics of morphology of lumen and gland such as size and shape, gland boundaries features, nuclei density at several scales, nuclei area and circularity. In addition, architectural features from graphs, for example Voronoi, Delaunay and Minimum Spanning Tree (MST) graphs constructed from color primitives (after segmentation procedures) may be extracted. Such architectural features include but are not restricted to number of nodes, statistics and entropy of edge length and polygon area, eccentricity, fractal dimension, among others. Once the feature extraction process is finished, algorithms for feature selection and ranking may be implemented to choose the features that best represent the tissue for classification purposes. The selected features are processed such that they are scaled according to their importance.

Referring now to the image classification step, several learning algorithms may be used. The classifiers may be decision trees, k-nearest neighbor, Bayesian, neural networks, and/or SVM. Boosting algorithms such us AdaBoost, SVM Boost, etc. can be used to improve the classification performance. Next table shows the classification accuracy ranges of the multiclass recognition task for grading prostate carcinomas regions of interest.

| Gleason pattern | Correct classification rate for different classes of images |
|---|---|
| Grade 3 | 93.33%-99.9% |
| Grade 4 | 86.67%-99.9% |
| Grade 5 | 100% |

Textural-Based System for Prostate Cancer Gleason Grading and Scoring (System 2)

Figure 8:
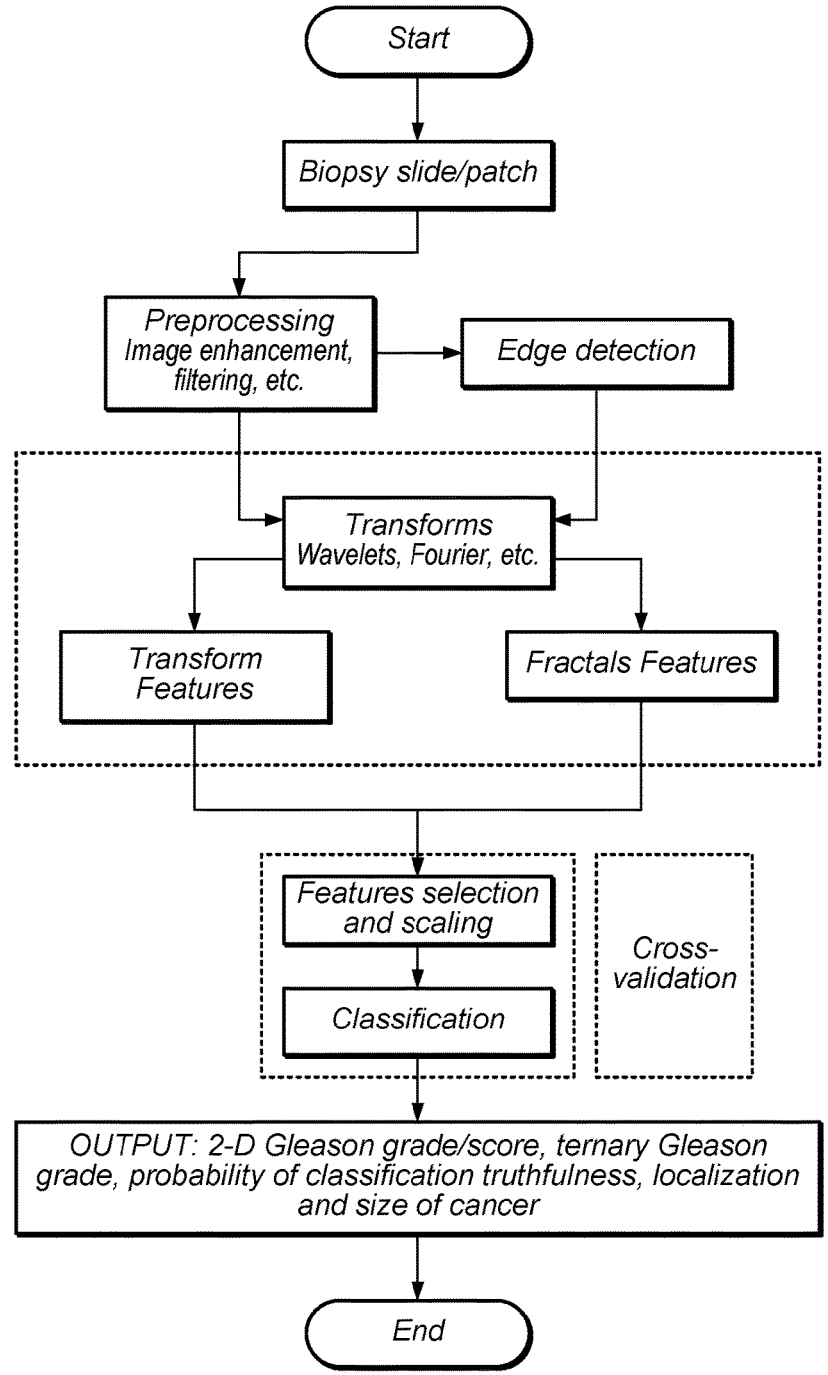
FIG. 8 is a block diagram of the first textural-based 2-D Gleason grading/scoring system.

In this embodiment, transform is considered for transform (wavelets, cosine, Fourier, and others) features extraction for classification of prostate cancer biopsy images. The flow diagram of this system for a wavelet transform is outlined in FIG. 8. Images are preprocessed using some of the previously discussed preprocessing techniques in the previous embodiments prior to image transform and features extraction. Features are classified using any suitable learning algorithm for example Support Virtual Machine (SVM). Classification performance showed that Haar wavelet transform produced an improved result in terms of energy features extractions when images are first preprocessed using the concept of morphological filtering and transform coefficients ratio.

Wavelet Transform:

In wavelet transform, the signal is decomposed into a family of orthogonal $\psi_{m,n}(x)$ and $\psi(x)$ as follows:

$$\psi_{m,n}(x)=2^{-m/2}\psi(2^{-m}x-n) \text{ for integers } m \text{ and } n$$

For the construction of the mother function $\psi(x)$, the determination of a scaling function $\Phi(x)$ is needed to satisfy the two-scale difference equation:

This yields the wavelet kernel $\psi(x)$ as follows:

$$\phi(x) = \sqrt{2}\sum_k h(k)\phi(2x-k); \psi(x) = \sqrt{2}\sum_k g(k)\phi(2x-k);$$

where $g(k) = (-1)^k h(1-k)$

For wavelet decomposition to a Jth-level, the relation of the decomposed coefficients to direct previous coefficients can be given as:

$$c_{j+1,n}=\Sigma_k c_{j,k}h(k-2n) \text{ and } d_{j+1,n}=\Sigma_k c_{j,k}g(k-2n)$$

where $0 \leq j \leq J$

For 2-D wavelet transform, the basis functions operate along the horizontal and vertical directions as a pair of low pass and high pass filters, h and g, respectively. The coefficients at the HH, HG, GH, and GG correspond to the Approximated, Horizontal, Vertical, and Detailed submatrices in the 2D transform space.

To illustrate the use of a transform in this embodiment, the Haar wavelet transform is shown as an example. The Haar basis function can be expressed as follows:

$$H(2) = \begin{pmatrix} +1 & +1 \\ +1 & -1 \end{pmatrix}$$

$$[Haar]_{2^n} = H(2^n) = \begin{pmatrix} H(2^{n-1}) \otimes (+1 \ +1) \\ \sqrt{2^{n-1}} I(2^{n-1}) \otimes (+1 \ -1) \end{pmatrix}, n=2, 3, \ldots,$$

Many different features can be extracted from wavelets and orthogonal transforms such as cosine, sine, Hartley, Fourier, and others. Some exemplary features may include the normalized coefficients of energy and entropy features for each decomposed submatrix at a given level as follows:

$$energy = \frac{\sum_i \sum_j x_{ij}^2}{n \times n}$$

$$entropy = -\left(\frac{1}{n \times n}\right) \sum_i \sum_j \left(\frac{x_{ij}^2}{norm^2}\right) \log\left(\frac{x_{ij}^2}{norm^2}\right)$$

Where $x_{ij}$ represents wavelet coefficients; n is the dimension of the submatrix, and $$norm^2 = \sum_i \sum_j x_{ij}^2$$

Due to the diversity of staining colors at each image, the performance of these features should be evaluated against each color component of any color model, for example RGB color. Energy and entropy features are then extracted for each submatrix and classified using the Support Vector Machine (SVM) classifier as an example. Features in the training set contain one class label and several multiple features. The learning objective is to sort the training data into groups/classes so that the degree of association is strong among the features of the same class and weak among other members of other classes. The set of features in our case represent the wavelet-based feature vectors.

As discussed previously, there is significant classification performance diversity among the different grades. In order to improve the classification performance, the concept of deploying the Human Visual System (HVS) rational filters is considered in both, the spatial domain of color channels, and in the wavelet transform domain.

In previous embodiment, we developed an algorithm for visualizing and detecting edges in a colored image using logarithmic approach. Some of the proposed morphological filters include the following:

$$\beta1\left(\frac{max(Fn)}{max(Fm)}\right); \beta2\left(\frac{min(Fn)}{max(Fm)}\right); \beta3\left(\frac{min(Fn)}{min(Fm)}\right); \beta4\left(\frac{max(Fn)}{min(Fm)}\right)$$

Where $\beta n$ is a constant used for grayscale normalization.

For the class of biopsy images, taking as an example the RGB color model, the filter considers the logarithmic ratio of the minimum RGB component to the maximum one. This type of filters has the ability to segregate the dark basal cells from other tissue characteristics. It operates on biopsy images as follows:

$$I_{new} = \beta \log_{10}\left(\frac{min(RGB)}{max(RGB)}\right)^{\alpha}$$

Where $I_{new}$ is the output processed/filtered image.

In another embodiment, the concept of rational filters in the transform domain is used. The wavelet transform provides a good localization property in space-frequency domain. Since the most significant coefficients information exist mainly in the approximated and detailed coefficient sub matrices, the ratio of these two matrices is taken, then the energy of the coefficients ratios is considered in classification.

A transform approach for image quality measurement using the properties of HVS has been proposed. For any wavelet transform, the rational filter coefficients for the low-low "Approximated" and high-high "Detailed" frequency filter banks in a 1-D signal can be given as follows:

$$C_{ratio_{1D}} = \frac{\sum_i Ci_A}{\sum_i Ci_D}$$

Similarly, the coefficients ratio, $C_{ratio}$, for the 2-D case is calculated as follows:

$$C_{ratio_{2D}} = \frac{\sum_i \sum_j Cij_{AA}}{\sum_i \sum_j Cij_{DD}}$$

Another proposed method is to use the phase information of the Lo and Hi coefficients ratio, which is expressed for 1-D signal as:

$$\theta_i = \tan^{-1}\left(\left|\frac{\sum_i C_i Lo}{\sum_i C_i Hi}\right|\right)$$

Features extracted from the proposed method are fused with the wavelet energy feature. The following table tabulates the classification performance for different classes of prostatic carcinomas by employing the explained approach.

| Gleason pattern | Correct classification rate for different classes of images |
| --- | --- |
| Grade 3 | 77.0%-99.9% |
| Grade 4 | 85.3%-99.9% |
| Grade 5 | 96.0-100% |

The classification performance using the proposed method succeeded in outperforming the previous method where energy feature is extracted from some color channels of the biopsy images directly.

Another extracted feature is related to the fractal dimension (FD) measure. One embodiment of the invention provides two developed algorithms in fractal analysis. The developed algorithms are based on edge detection information as a preprocessing stage as well as quad-tree decomposition algorithms. The classification performance resulting from adopting such pre-processing algorithm showed an improved performance in some Gleason grades over the classical implementation of the box counting method.

Methods for Computation of Fractal Dimension by Improved Box-Counting Algorithm

The architecture and geometrical features of biopsy images of prostate presents a rich domain for fractal analysis through the concept of fractal dimension (FD). The fractal dimension provides a geometrical description of an image by measuring the degree of complexity and how much space a given set occupies near to each of its points. The growth of cancer through the development of different architectures associated with different grades shows distinct features that can be used for classification using fractal dimension. Malignant cancerous cells demonstrate darker intensity gray level values compared to the surrounding tissue parts. In this part, fractal features through Differential Box Counting (DBC) will be used.

Given a set S in Euclidean n-space, the self similarity of S is obtained if Nr distinct copies of S exist by r ratio. The following equation provides the fractal dimension measure "D" as follows:

$$D = \frac{\log(N_r)}{\log(1/r)}$$

To find the box-counting dimension, the image is binarized by using any proper approach in order to have two levels of intensities, either 0 or 1, rather than 256 gray levels intensities. To find a suitable binary image for fractal dimension computation several algorithms such as the proposed logarithm edge detection, gray level thresholding, adaptive thresholding, and bit-plane decomposition may be used. Then, the binary image is divided into grids of size r and the number of grid boxes Nr exhibiting self similarities is counted. The next step is to reduce the grid size, r2 and find the corresponding number of boxes, Nr2. Grid sizes are reduced in a pattern following 2n. For instance, a 512×512 image yields the following grid sizes, 512, 256, 128, 64, 32, 16, 8, 4, and 2 grid sizes. The resulting fractal dimensions for each grid size are fused together to obtain a unique fractal dimension.

Also, in this embodiment we proposed an edge detection-based fractal dimension measure (EDFDE). It is utilizing the concept of edge detection using parameterized logarithmic image processing, which was developed in previous embodiments. Biopsy images go through PLIP-based edge detection prior to box counting.

In summary, feature vectors were extracted from wavelet and fractal analysis domain. Each extracted feature vector represents a different architectural property used for classification purposes feature vectors from wavelet transform provided a high performance for classifying and grading biopsy images. Before classification step, feature selection is performed. The objective is to select features sets that best describes the statistical property of the biopsy images classification features. There are various algorithms for features selection and validation of features prior to classification in literature. For example, the minimum-Redundancy Maximum-Relevance (mRMR) features selection method may be used. Using the mRMR method, the features space (N-features) is reduced to M-features (N>M).

Referring in more details to the image classification step, several learning algorithms may be used. The classifiers may be decision trees, k-nearest neighbor, Bayesian, neural networks, and/or SVM. Boosting algorithms such us AdaBoost, SVM Boost, etc. can be used to improve the classification performance. The table below shows an example of classification of images from different Gleason grades and highlights the final SVM classification performance using "leave-one-out" cross-validation.

| Gleason pattern | Correct classification rate for different classes of images |
|---|---|
| Grade 3 | 93.0%-99.9% |
| Grade 4 | 89.3%-99.9% |
| Grade 5 | 96.0-100% |

Textural-Based System for Prostate Cancer Gleason Grading and Scoring (System 3)

Figure 9:
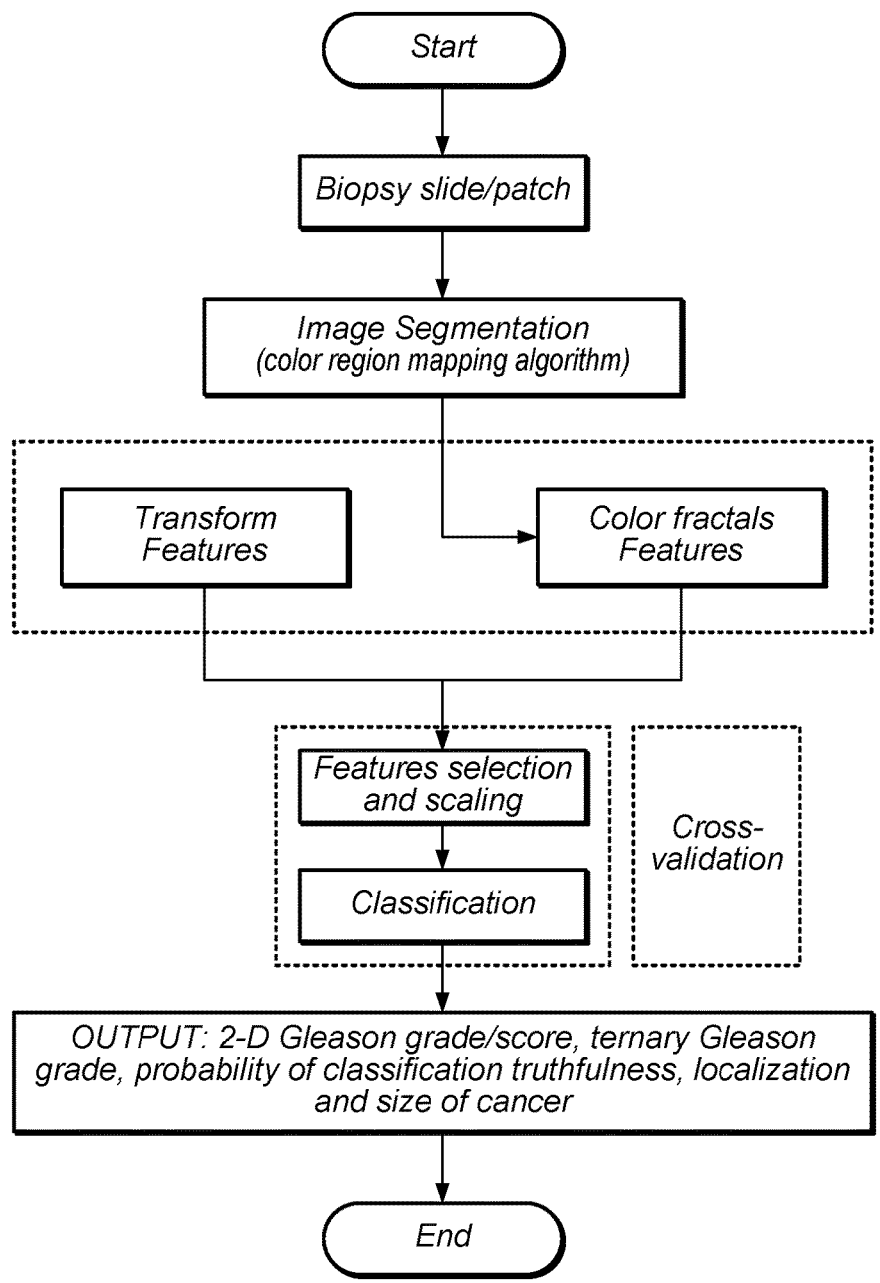
FIG. 9 is a flow diagram of the second textural-based 2-D Gleason grading/scoring system using the proposed new Color Fractal Dimension.

In this embodiment, the invention provides a system with several methods for automatic classification of prostate cancer carcinomas by using wavelet-based and fractals-based textural features. Image-level features are extracted from wavelet decomposition and color fractal analysis of images, as well as object-level fractal dimension features as it is shown in FIG. 9. Referring now to the embodiment in more detail, the following features are extracted from the cancerous images:

Transform-Based Features:

In order to compute the feature vectors, real/complex wavelets or multi-wavelets or other orthogonal transforms (e.g. Fourier, cosine, sine, Hartley, Hadamard) may be used in general. Several wavelet transforms are widely used for quantitative image processing since they provide an effective tool for multi-resolution analysis. A particular approach may include parameterized Slant-Haar transform [19], which is described below:

Slant-Haar wavelet is the wavelet transform of choice for this example. The slant-Haar transform of order $2^n$ for n=3, 4, 5 . . . , is defined by:

$$X = S_{2^n} X$$

Where x is an input data vector of size n.

$$S_{2^n} = S_{2^n}(\beta_4, \ldots, \beta_{2^n})$$

$$S_{2^n} = Q_{2^n} \begin{bmatrix} A_2 \otimes S_{2,2^{n-1}} \\ \ldots \\ I_2 \otimes S_{2^n - 2, 2^{n-1}} \end{bmatrix}$$

For $-2^{2n-2} \leq \beta_{2^n} \leq 2^{2n-2}$ and $n \geq 3$

Where $S_{2,2^{n-1}}$ is a matrix of dimension $2 \times 2^{n-1}$ comprised of the first two rows of $S_{2^{n-1}}$, and $S_{2^{n-1}-2,2^{n-1}}$ is a matrix of dimension $(2^{n-1}-2) \times (2^{n-1})$ comprised of the third to the $(2^{n-1})$th rows $S_{2^{n-1}}$. The symbol $\otimes$ denotes the operator of the Kronecker product. The matrix $A_2$ is given by:

$$A_2 = \frac{1}{\sqrt{2}} \begin{bmatrix} 1 & 1 \\ 1 & -1 \end{bmatrix}$$

And the matrix $S_{2^{n-1}}$ is the recursion kernel defined by:

$$Q_{2^n} = \begin{bmatrix} 1 & & & & \\ & b_{2^n} & a_{2^n} & & \\ & a_{2^n} & -b_{2^n} & & \\ & & & 1 & \\ & & & & 0 \\ & & & & & 1 \end{bmatrix}$$

$$a_{2^n} = \sqrt{\frac{3(2^{2n-2})}{4(2^{2n-2}) - \beta_{2^n}}}, \quad b_{2^n} = \sqrt{\frac{(2^{2n-2}) - \beta_{2^n}}{4(2^{2n-2}) - \beta_{2^n}}}$$

For $-2^{2n-2} \leq \beta_{2^n} \leq 2^{2n-2}$ and $n \geq 3$

Another approach may include parameterized PLIP Slant-Haar transform. In PLIP Slant-Haar wavelet, the arithmetic operations in wavelet definitions are replaced by PUP operations [14]:

$$g_1 + g_2 \rightarrow g_1 \oplus g_2 = g_1 + g_2 - \frac{g_1 g_2}{\gamma(M)}$$

$$g_1 - g_2 \rightarrow g_1 \ominus g_2 = k(M) \frac{g_1 - g_2}{k(M) - g_2 + \varepsilon}$$

$$g_1 g_2 \rightarrow g_1 * g_2 = \varphi^{-1}(\varphi(g_1)\varphi(g_2))$$

Where k(M), γ(M) are arbitrary linear functions of the type γ(M)=AM+B for constants A and B. The parameter ε is a very small constant included to avoid division by zero in the case k(M)=$g_2$.

Referring now in more detail to the features which can be extracted from wavelet coefficients, the following features are considered:

Statistics of wavelet detail coefficients: Using a wavelet transformation of the three color components of the image in one or more color models at a specific scale, the first order statistics of scaled coefficients of each sub-band are computed and arranged as a feature vector. Those statistics may include average, median, standard deviation, high order moments, among others.

Phase information of approximation and detail coefficients: After transforming the image using any suitable wavelet basis, the phase information generate by the approximation and detail coefficients may be computed as follows:

$$\theta_i = \tan^{-1}\left(\left|\frac{\sum_i C_i \text{Lo}}{\sum_i C_i \text{Hi}}\right|\right)$$

Joint Probability distribution of wavelet detail coefficients: The color input image is first decomposed into its RGB components. Before applying 2-D wavelet filters, color model transformation can be performed. Next, wavelet decomposition is performed for each channel separately and joint probability of scaled detail coefficients is computed for each possible pair of channels. The joint distribution consists of a set of bins which counts the number of wavelet details coefficients at a given scale falling in a given area of the plane:

$$p_{Chi,Chj}(x, y) = k \sum_x \sum_y \text{ AND } (Ch_i = x, Ch_j = y)$$

$$\forall i \neq j; i, j = 1, 2, 3$$

In equation 3, i, j=1, 2, 3 indicate the three channels of a color input image. x, y represent the numerical value of the coefficients which range, in our experiments, from 0 to 255. The logical AND function will return 1, when both arguments are true, and 0 otherwise in order to count the number of coefficient falling in a given bin.

Wavelet Generalized Energy Distribution: In order to capture how the wavelet energy is distributed within the images, each input image (gray scale image or R-G-B components) is divided into non-overlapping s×s blocks. A wavelet transformation, for example Haar transform, is then applied to each block independently. The wavelet transform converts the data array into a series of wavelet coefficients, each of which represents the amplitude of the wavelet function at a particular location within the array and for a given wavelet scale. The generalized energy of approximation sub-band can be computed as:

$$E_i^A = \sum_{j=1}^{N} |A_{ij}|^P, i = 1, \ldots, K, P =, 1, 2, 3, \ldots$$

Here, K is the wavelet decomposition level. N is the number of the coefficients in the approximation sub-band at each decomposition level. First order statistics, i.e. mean, standard deviation, median, minimum to maximum ratio, etc, of the energy distribution are computed to produce feature values.

According to an embodiment of this invention, the sub-band coefficients are processed by a window function, wherein the center coefficient $x_{ij}$ is replaced by the result of the function $f_w(x_{i,j\to m\times n})$ in a small neighbor w of size m×n, m, n=1, 2, 3, . . . .

For example, the function for a 3×3 neighbor could be:

$$f_w(x_{i,j\to 3\times 3}) = \Sigma[x_{i,j}(x_{i-1,j-1}{}^{\alpha 1} x_{i-1,j}{}^{\alpha 2} x_{i-1,j+1}{}^{\alpha 3} x_{i,j+1} \times_{i,j}{}^{\alpha 4} x_{i,j-1}{}^{\alpha 5} x_{i+1,j-1}{}^{\alpha 6} x_{i+1,j-1}{}^{\alpha 7} x_{i+1,j}{}^{\alpha 8} x_{i+1,j+1}{}^{\alpha 9})]^2$$

Where $\alpha_i$ are user-defined constants, for example 0, 1, 2, . . . .

Or, $$f_w(x_{i,j\to 1\times 1}) = \sum x_{i,j}^2,$$

$$f_w(x_{i,j\to 1\times 1}) = \sum \text{Log}^2 |x_{i,j}|,$$

$$f_w(x_{i,j\to 1\times 1}) = \sum |x_{i,j}| \text{Log}|x_{i,j}|$$

$$f_w(x_{i,j\to 1\times 2}) = \sum (x_{i,j} x_{i,j-1})^2$$

$$\theta_i = \tan^{-1}\left(\left|\frac{\sum_i C_i \log(\text{Lo})}{\sum_i C_i \log(\text{Hi})}\right|\right)$$

$$\theta_i = \tan^{-1}\left(\left|\frac{\sum_i C_i \log(\text{Lo}(x_{i,j} x_{i,j-1}))}{\sum_i C_i \log(\text{Hi}(x_{i,j} x_{i,j-1}))}\right|\right)$$

The features above can be computed using the transformed wavelet coefficients. In the case complex wavelet are used, $x_{ij}$ refers to the magnitude of the coefficients.

Method for Computation of Color Fractal Dimension

Figure 10:
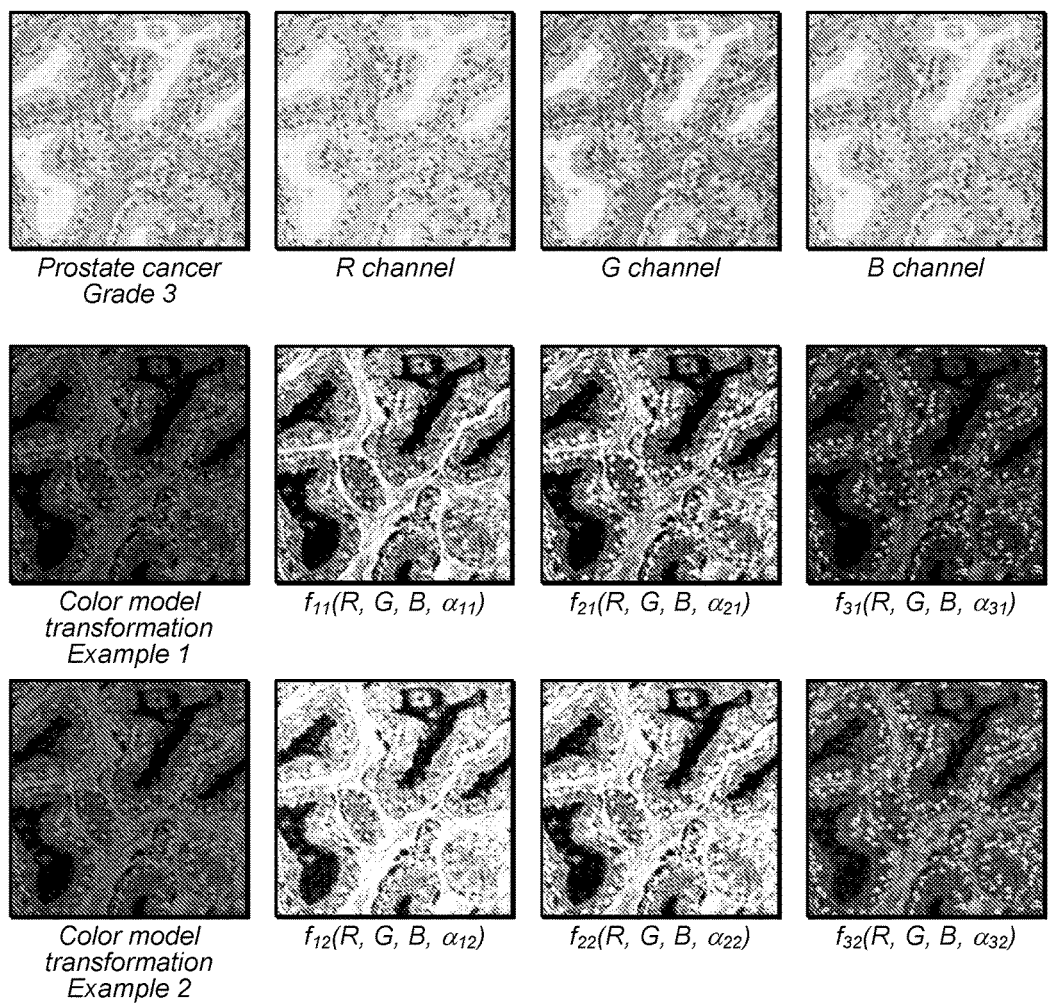
FIG. 10 shows two examples of color model transformation for computation of new Color Fractal Dimension.

In accordance with an embodiment of this invention, a new algorithm for computing fractal dimension of color images is proposed. The modified algorithm is based on a color space transformation of the histopathology images. To this end, a new modification in the (R,G,B) color space is used. The proposed algorithm extracts a single fractal dimension of a color image or a fractal dimension vector corresponding to the color fractal dimension of non-overlapping blocks of size m×n. In this algorithm the color image is considered a set of points in a 5-dimensional space S. Each point s∈S is represented by its two spatial dimensions and its three color components in the new color model $s_i$=(x,y, $f_1(R,G,B,\alpha_1)$, $f_2(R,G,B,\alpha_2)$, $f_3(R,G,B,\alpha_3)$) where $f_i$ is a function of 3 colors and some set of constants $\alpha_i$. The function should be adjusted to enhance the separation between cancer grades. Various examples of the color transformation are shown in FIG. 10. Color fractal dimension D of an image can be approximate by:

$$N(L) = g(L) \sum_{m=1}^{N} \frac{1}{m} P(m, L) \infty L^{-D}$$

Where, N(L) is the total number of boxes (size L) needed to cover the image, and it is multiplied by a function g(L), such as g(L)=1, L, $L^2$, log L, L log L. P(m,L) is the probability matrix having m points included into a hypercube (or box) of size L centered at an arbitrary point of S. Below, the probability matrix calculation procedure is outlined:

1. Count the number of points s∈S, $$s_i=(x,y,f_1(R,G,B,\alpha_1),f_2(R,G,B,\alpha_2),f_3(R,G,B,\alpha_3)) \text{ with}$$

d(F,Fc)≤L in which d (F,Fc) is a distance between the center pixel Fc and the rest of pixels F in the box, and $f_i, f_{ci}$ is the value of the i-th dimension of point s∈S in the 5-D space $s_i$=(x, y, r', g', b'). For example, the distance d (F, Fc) could be:

The Minkowski distance $$d(F,Fc)=|F-F_c|=\max(|f_i-f_{ci}|) \forall i=1,2\ldots,5$$

Or, p-norm distance $$d(F, Fc) = |F - F_c| = \left(\sum_{i=1}^{5} |f_i - f_{ci}|^p\right)^{1/p}$$

2. For an arbitrary size L normalize the matrix P(m,L) by using the following relationship $$\sum_{m=1}^{N} P(m, L) = 1$$

in which N is the number of pixels included in a box of size L.

Finally, the fractal dimension D is found by the linear fitting of the negative of the logarithm of L against the logarithm of its corresponding. The best function g(L), can be found using $$G = \max_{g}\left\{\min_{i,j}(d_{i,j})\right\}$$

Where $d_{i,j}$ is the distance between pairwise averages $Av_i$ with i=3, 4, 5, of the fractal dimension of the set of class of images of Gleason grades 3, 4 and 5 calculated for each function g(L).

Simplifications of the invented algorithm result in the color fractal dimension introduced by Ivanovici [20].

Referring now to the image classification step, several learning algorithms may be used. The classifiers may be decision trees, k-nearest neighbor, Bayesian, neural networks, and/or SVM. Boosting algorithms such us AdaBoost, SVM Boost, etc. can be used to improve the classification performance. Next table shows the classification accuracy ranges of the multiclass recognition task for grading prostate carcinomas regions of interest.

| Gleason pattern | Correct classification rate for different classes of images |
|---|---|
| Grade 3 | 99.9%-100% |
| Grade 4 | 86.67%-99.9% |
| Grade 5 | 100% |

3-D Gleason Grading System (System 4)

Figure 11:
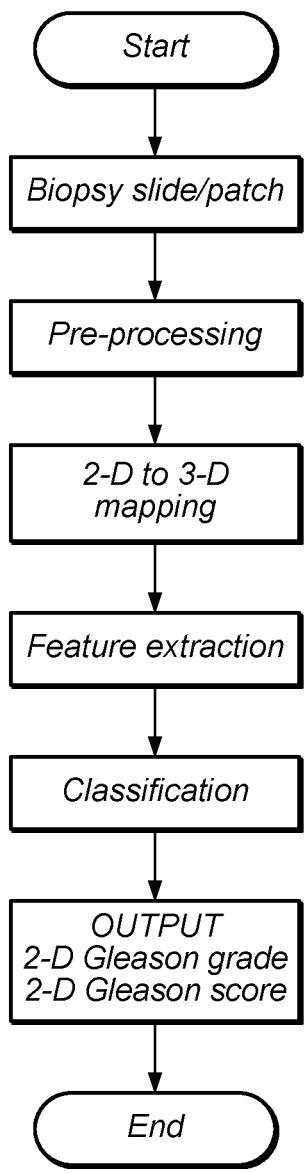
FIG. 11 is a general flow diagram of the 3-D Gleason grading system.

In this embodiment, 3-D image is obtained using a single 2-D tissue image to assign Gleason grade and score to the third dimension of the reconstructed image. The building blocks of this part are shown in FIG. 11 and will consider the following steps:
  (1) Mapping and pre-processing: feature vectors algorithms related to wavelet transform, and fractal analysis will be considered. The initial step considers mapping 2-D images into slices of layers using pre-developed mapping algorithms in order to have a 3-D voxel representation of a single 2-D image. Preprocessing algorithms will consider: Haar-HVS based algorithms, logarithmic RGB model representation, and edge detection-based algorithms.
  (2) Feature vectors normalization: feature vectors generated from above algorithms will be normalized.
  (3) Feature Selection and Classification: feature selection algorithms may be deployed to select dominant features generated as described above. Several classifiers can be used for recognition. For example SVM classifier may be used to classify such features and generate a Gleason score.
  (4) Integration and validation: the final output of this subsystem may be verified and integrated with the 2-D Gleason subsystem.

Referring now in more details to this embodiment of the invention, the mapping of a single 2-D image into a 3-D space may be done by using several mapping algorithms. The used algorithm are grouped in depth cues such as defocus, linear perspective, shading, patterned textures, symmetric patterns, occlusion, statistical patterns, among others.

System for Whole-Slide Processing and Prostate Cancer Diagnosis: Detection, Grading, Mapping, Scoring (System 5)

A computer-aided diagnosis system addresses the detection, Gleason grading, scoring and mapping of prostate carcinoma in whole digitized slides. The system follows a multi-resolution approach, in which specific features are extracted at a specific image magnification. For example: (1) at low resolution color and textural features are extracted, (2) at medium resolution, architectural tissue analysis is performed via graph features, and (3) At high resolution, the morphological and wavelet features are used for tissue characterization. The system proceeds as follows: The biopsy specimen is segmented from the background to save calculation time, a square or rectangular grid of size m×n is superimposed for patch-based cancer diagnosis (the size of the grid could change depending on the resolution), spatial and transform domain (multi-resolution analysis) features are extracted and block classification is performed by using any of the systems of the previous embodiments.

Figure 12:
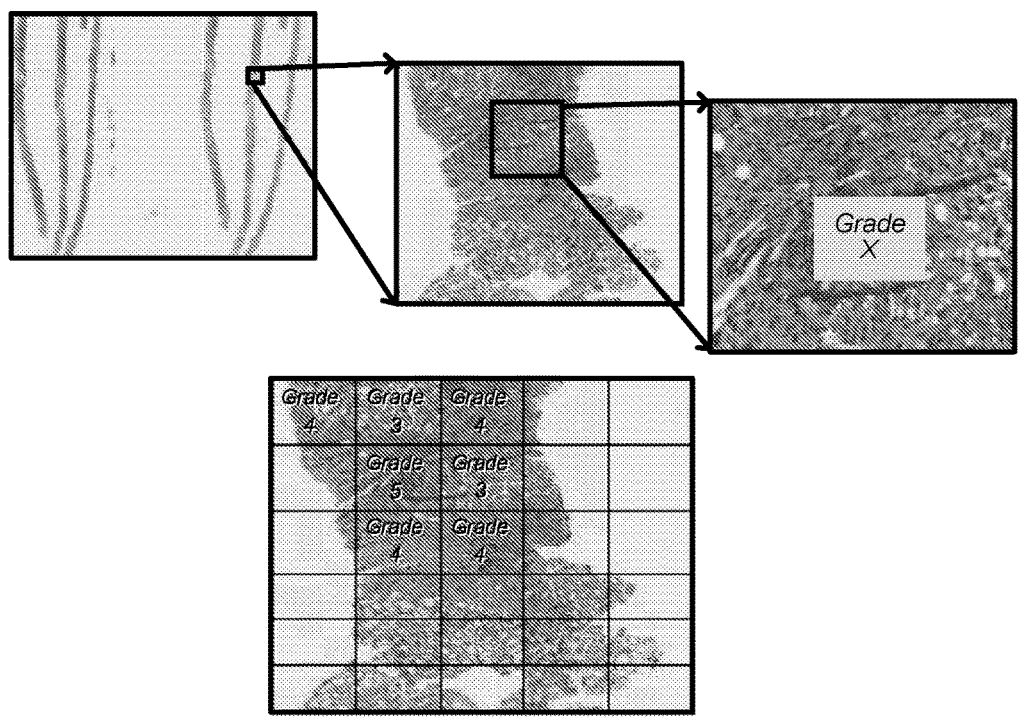
FIG. 12 presents an example of prostate cancer localization and cancer mapping from prostate cancer biopsy.

A classification system according to an embodiment of the invention uses multiple features for classification of Whole-Slide and several computer algorithms which produce the following final outputs: tumor extent in the needle biopsy, number and identification of positive needle cores, percentage of positive cores for cancer, length of the tumor in positive cores and length of the core, percentage of needle core tissue affected by carcinoma and area of tissue positive for cancer, Gleason grade of each selected cancerous region of interest, percentage of each Gleason pattern in biopsy specimens, Gleason score of each positive core, including tertiary pattern information, the most frequent Gleason score in slides, numbers of identical Gleason scores in the positive cores, and localized cancer map including the grade of each cancerous patch in all needle biopsy slides as shown in FIG. 12.

In accordance with this embodiment, the classification algorithm uses morphology-, textural-based classification subsystems or a combination of those systems provided in previous embodiments of the present invention. As a result, a grade of the Gleason grade scale is assigned to each cancerous patch in the whole slide and the Gleason score is computed automatically. In addition, the system is able to detect tertiary patterns present in the biopsy image. The percentage of extent of each grade found in the image is also computed.

The system of studying biopsy samples may be an automated procedure to process large number of biopsy slides by integrated a production line model. The automated system output automatically classifies 2-D and 3-D Gleason grades by using serial sections/slices of prostate core biopsy images. The automated system output automatically recognize de Gleason grade, compute the Gleason score and predicts the likelihood of prostate cancer reoccurrence after treatment, as well as more accurate risk assessment, and the decision on the necessity of further biopsy samples. The automated system output allows improved and efficient treatment planning.

In an embodiment, the method and system allow a surgeon to be immediately aware of whether the surrounding tissue of a specimen completely surrounds the tumor, prior to the time that the patient is closed up.

3-D Core Grading/Scoring System (System 6)

Digital 3-D reconstruction of tissue has many uses in medical research and it can be also used for cancer diagnosis because more features can be analyzed from high-resolution 3-D images. For example, additional information regarding the volume of tumor areas, the distribution of cells, the branching of blood vessels in a tumor, etc can be extracted to make better and more accurate cancer diagnosis and prognosis.

The building blocks of this embodiment will consider the following:

(1) Acquiring images: serial sets of images (M sets from N patients with 12 slices each) need to be pre-labeled by a multiple experienced pathologists with Gleason score ranging from 3+3 to 5+5 for learning algorithm training.

(2) Building 3-D model: building a 3-D image from a set of slices for preprocessing and featuring vectors generation in the next step.

(3) Preprocessing and feature vectors generation: preprocessing algorithms presented earlier in this proposal are used for the investigation of the core pattern and a possible feature vectors generation. The extracted features may include: shape and structure of cells, graph features, 'micro-architecture' of blood vessels, and tumors' volume, shape, regularity, among others.

(4) Classification and validation: in this part, a Gleason grade and score are given to the 3rd dimension of the core based on SVM classifier or other suitable classifiers with different validation methods. The labeled grades are investigated and verified with a pathologist to insure validation of the grade and its correlation with the 2-D grading subsystem.

In accordance to an embodiment of this invention, the image acquisition process may be performed by using a photon-light, a stereo-light microscope or an electron microscope. The selection of the microscope should be done according to the required image resolution.

Figure 13:
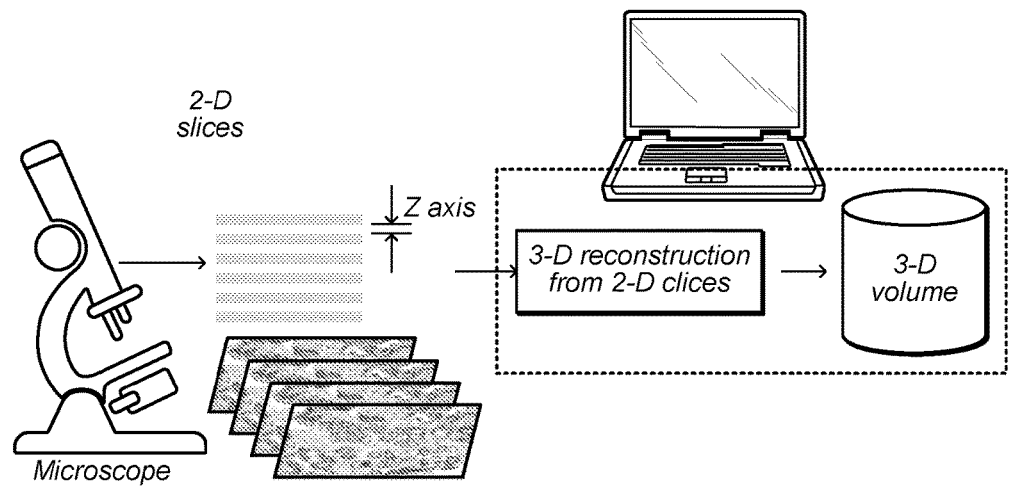
FIG. 13 illustrates a process to reconstruct 3-D images from 2-D slices.

To construct 3-D image from 2-D slices, different software tools can be used. For instance, ImageJ, Fiji, or developed algorithms in Maltab, among others. The general flow diagram for 3-D reconstruction is shown in FIG. 13.

Figure 14:
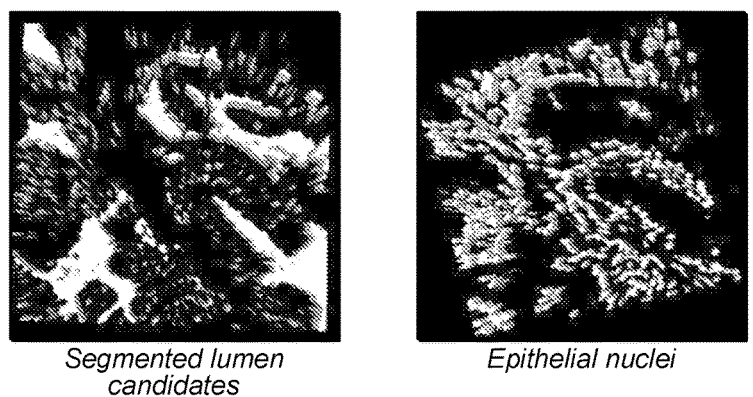
FIG. 14 shows an example of 3-D reconstruction of segmented lumens and epithelial nuclei from a prostate cancer biopsy image.

According to another embodiment of the invention, tissue image preprocessing and structure segmentation may be performed using 2-D slices. FIG. 14 shows an example of 3-D reconstruction of segmented lumens and epithelial nuclei from a prostate cancer biopsy image. Feature extraction may be performed from both 2-D and 3-D images.

Figure 15:
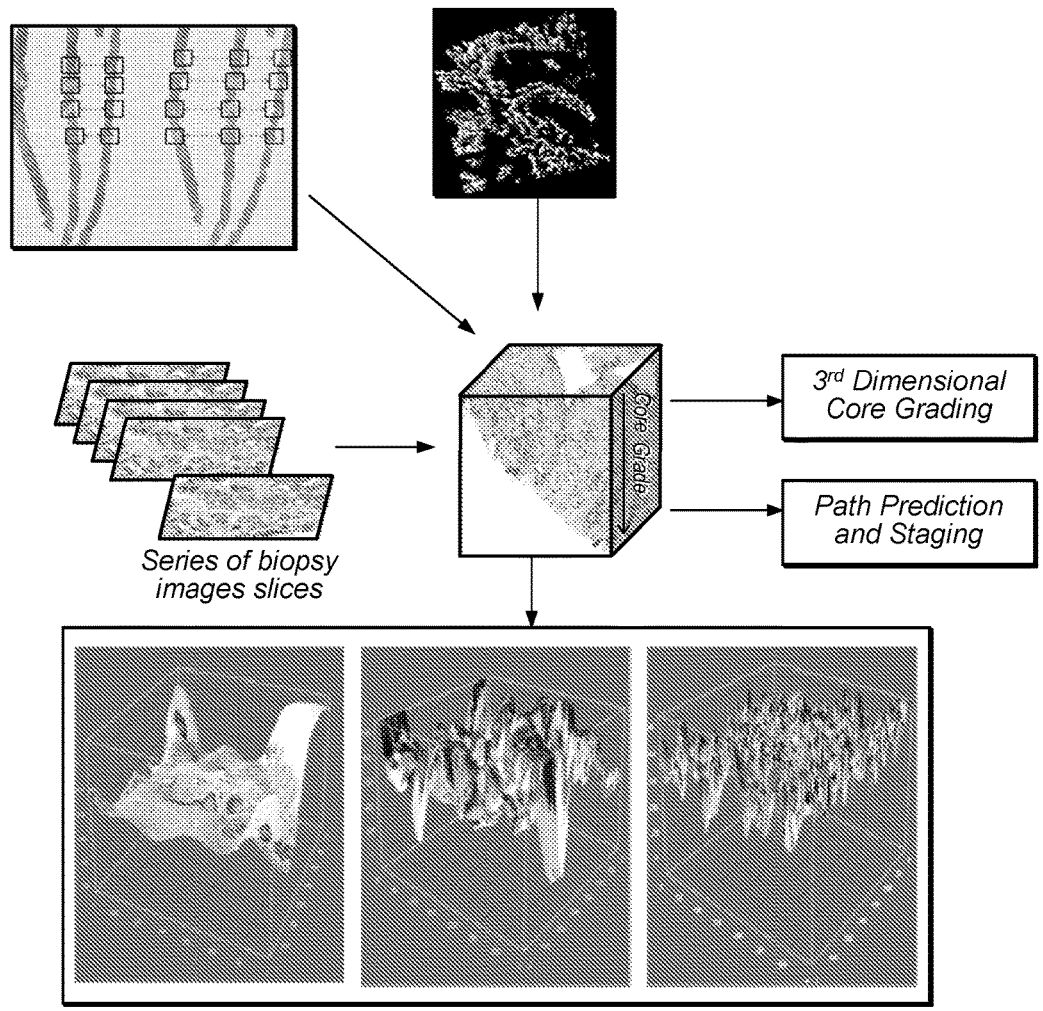
FIG. 15 presents a 3-D core grading system.
Figure 16:
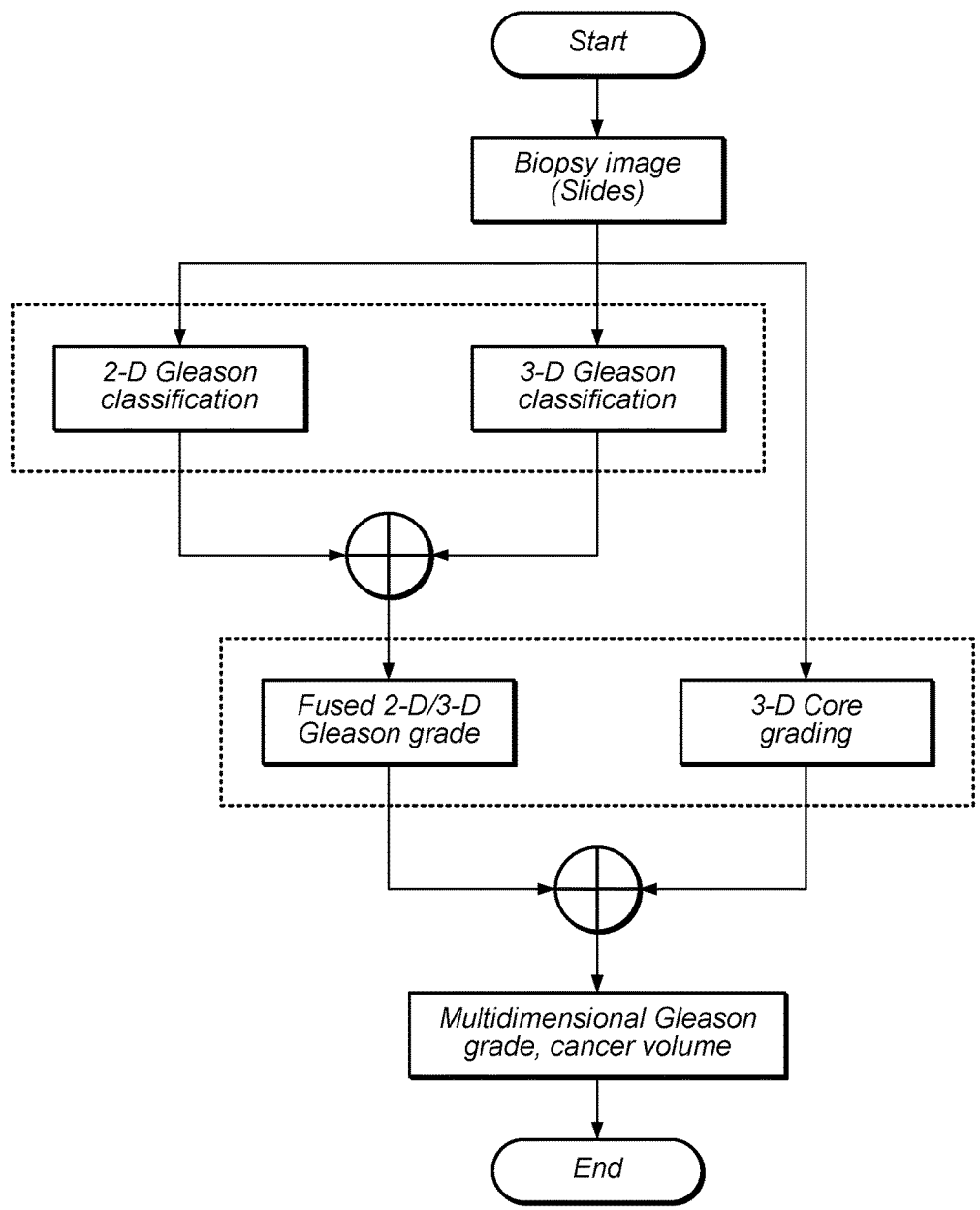
FIG. 16 shows the steps for computation of "Revised Gleason grade";"

According to another embodiment of the present invention, Gleason grading and scoring is performed in the 3-D tissue image from longitudinal and transverse views (see FIG. 15). The total volume of the tumor is also calculated. In this part, the Gleason score of the tumor will be computed as the combination of the most predominant grades in both directions. For example, the most predominant grade could be the average or mode of the grades which were found in the longitudinal and transverse tissue evaluation. If the distribution is bimodal or multimodal, the first component of the 3-D Gleason grade will be the maximum grade among the modal values and the second component will be the next grade value. Ternary patterns may be included in the final Gleason score, especially if those patterns correspond to a high Gleason grade.

System for Whole-Slide Processing and Prostate Cancer Diagnosis: Detection, Grading, Mapping, Scoring (System 7)

A computer-aided diagnosis system addresses the detection, Gleason scoring and mapping of prostate carcinoma in whole digitized slides. The system follows a prediction/compression (PC) approach, in which predictors are trained to optimally compress different Gleason patterns. For example: (1) segment the query image (color, tissue structures, gland and architectural features) into pattern-defining characteristics, (2) reduce query to quarter scale using a wavelet transform approximation, (3) unravel 2-D query into 8 distinct space-filling curves, (4) train a universal predictor/compressor (UDC) on each Hilbert curve, (5) train 3 UDCs on collections of already-graded 3, 4, and 5 patterned, archival images, (6) compress the query image Hilbert curves with each UDC, (7) statistically analyze compression results, and (8) grade query image and pixels with Hard and Soft scores computed from the statistical results.

Biopsy image preparation is necessary for formatting image data into a structure usable by the novel universal compressor-detectors (UDCs). Images need to be simplified and reduced to support fast data analysis and also need to be one-dimensionalized for construction and implementation of a UDC. Specifically, image data must support two phases of UDC action:

1. Training and
2. Detection.

Training builds UDC structures on pathologist-graded, one-dimensionalized, Gleason pattern images. Detection involves prediction and compression operations by a UDC on a similarly prepared query image Thus, image preparation for both training images and query images consists of three significant steps: (1) structural segmentation for image simplification, (2) image downscaling for data reduction, and (3) 1D conversion for UDC support. While different approaches may be taken to perform these steps, the methods chosen here are designed to facilitate computational speed while simultaneously maintaining the robustness of the system.

First, 512×512 pixel, H&E-dyed biopsy images are segmented into six significant structural elements including: lumen, epithelial cytoplasm, stroma, blue mucin, and epithelial nuclei. The method simultaneously extracts the important features found in the various Gleason patterns and reduces the dynamic range of pixel values (originally 0-255 in each of the red, green, and blue channels) to 0-5, effectively reducing the image alphabet size from the approximately $1.68×10^7$ color combinations of an RGB image to 6, which is a very practically sized alphabet for a UDC to handle.

Images are also reduced to quarter scale (64×64 pixels) in order to reduce the number of pixels from 262,144 per image to 4,096 per image. This action preserves significant regional statistics within the sample images while alleviating the amount of data on which a UDC must train or compress. Scale reduction is achieved using a 2-level integer Haar wavelet transform to generate a 64×64 approximation of the original 512×512 segmented images and to preserve the dynamic range of the alphabet. Other wavelets could be used for the same task; however, the Haar is chosen because of its ability to be computed with extreme speed.

Lastly, the scaled, segmented image is unwrapped into one dimension to support use with a UDC. For example, this can be achieved by using several Hilbert curve raster scans. A Hilbert curve is a fractally-generated, space-filling curve on integer powers of 2 sided hyper-squares. For example, for every square digital image with sides of $2^p$ (where p is an integer) pixels a Hilbert curve [25] can be constructed which traverses all pixels continuously through adjacent pixels. In fact, 8 unique Hilbert curves can be constructed for square 2-D images.

For UDC training (and compression), a 64×64 Haar approximation of an image is unwrapped into its 8 unique Hilbert curves on which UDCs can be trained. For query image compression, a UDC compresses each of the 8 Hilbert sequences separately, and the average compression rates for each pixel are recorded. Thus, if $UDC_g$ predicts the probability $p_{ijk}^g$ for pixel (i, j) from the context of kth Hilbert curve (k=1, 2 . . . 8), then the observed compressed size in bits of pixel (i, j) using $UDC_g$ is $$Y_{ij}^{UDC_g} = \frac{\sum_{k=1}^{8} -\log_2(p_{ijk}^g)}{8}$$

The distributions of average pixel compression rates for a query image using each UDC are used to determine the Gleason grade of the query image. In the following sections, reference to a query image or its pixels specifically refers to the segmented, down-scaled versions and not the original query image.

The novel grading system supplies both hard grades (grades where the decision must be either grades 3, 4, or 5 and no in between) and soft grades (where the grade is a fuzzy membership average of multiple classes, generating a continuous scale Gleason grade) to a query image as a whole based on UDC compression rates. Query image pixels are also assigned individual hard and soft grades depending on the "distance" of a trained UDC's compression model to an optimal compression model after observation of that pixel. (Note that only images of grades 3, 4, and 5 are considered as these represent the significant patterns to cancer grading and were available for our analysis.)

The system roughly consists of roughly 8 discrete parts, illustrated in FIG. 9:

1. UDC Training: 3 UDCs are trained on respective classes of images. 1 UDC is trained on a query image under inspection.
   a. $UDC_3$ is trained on pathologist-graded pure pattern 3 images.
   b. $UDC_4$ is trained on pathologist-graded pure pattern 4 images.
   c. $UDC_5$ is trained on pathologist-graded pure pattern 5 images.
   d. $UDC_0$ is trained on a single query image.
2. Query Image Compression: Each UDC compresses an ungraded query image, I, and each pixel (i, j)'s compressed size in bits is stored as an observation $Y_{ij}^{UDC_g}$. Concurrently, pixel errors $\varepsilon_{ij}^{UDC_g}$ are also computed using the Kullback-Leibler divergence of a pattern UDC with respect to $UDC_0$, which is the optimal compressor for the query image by construction.
   a. $UDC_3$ compresses I with compressed pixel sizes $Y_{ij}^{UDC_3}$.
   b. $UDC_4$ compresses I with compressed pixel sizes $Y_{ij}^{UDC_4}$.
   c. $UDC_5$ compresses I with compressed pixel sizes $Y_{ij}^{UDC_5}$.
   d. $UDC_0$ compresses I with compressed pixel sizes $Y_{ij}^{UDC_0}$.
   e. KL divergence measures the model errors $\varepsilon_{ij}^{UDC_3}$ of $UDC_3$ to $UDC_0$ produced by observation of pixel $I_{ij}$.
   f. KL divergence measures the model errors $\varepsilon_{ij}^{UDC_4}$ of $UDC_4$ to $UDC_0$ produced by observation of pixel
   g. KL divergence measures the model errors $\varepsilon_{ij}^{UDC_5}$ of $UDC_5$ to $UDC_0$ produced by observation of pixel 4.
3. Analysis of Variance Testing: ANOVA is used to determine whether or not the mean compression rates provided by $UDC_3$, $UDC_4$, and $UDC_5$ are statistically dissimilar.
4. Hard Grading: A hard decision H for the query image Gleason grade is made corresponding to the best-compressing UDC's class.
5. Hard Mapping: The query image is mapped, pixel by pixel, with a hard grades $H_{ij}$ corresponding to the minimally divergent UDC model at each pixel.
6. Soft Grading:
   a. If ANOVA testing indicates the UDC compression rates are not statistically dissimilar, the query image is given a soft grade S=UNLCASSIFIABLE, meaning the image is not a distinct member of any UDC class.
   b. If ANOVA testing indicates that at least 2 UDCs are statistically dissimilar
      i. Tukey's multiple comparison test is used to test the independence of each UDC's mean compared to the others' means.
      ii. The query image is given a soft grade S using weighted means based on the intersections of the t-distributions modeling the mean UDC compression rates.
7. Soft Mapping: The query image is mapped, pixel by pixel, with a soft grades $S_{ij}$ computed using weighted means based on the inverse KL divergence of each pixel.
8. Prediction of Most Likely Pattern Composition:
   a. The probability of grade transitions from each grade to the others are computed from the errors associated with each UDC model.
   b. The final pattern composition (in percent of each pattern) is computed through steady state analysis of the transition model.

Prognosis System for Integration of Biopsy Classifier Systems with Patient and PSA Information (System 8)

In one embodiment of the present invention, a computerized system is developed by introducing a unique recognition and prognostic system that provides the following: (1) Recognition and classification of Gleason grading in 2-D biopsy images, 3-D biopsy images, and 3-D core patterns; (2) faster and accurate classification with the introduction of image preprocessing algorithms; and (3) integration of patient personal data and prostate-specific antigen (PSA) information for more accurate recognition and prognostics analysis.

Figure 17:
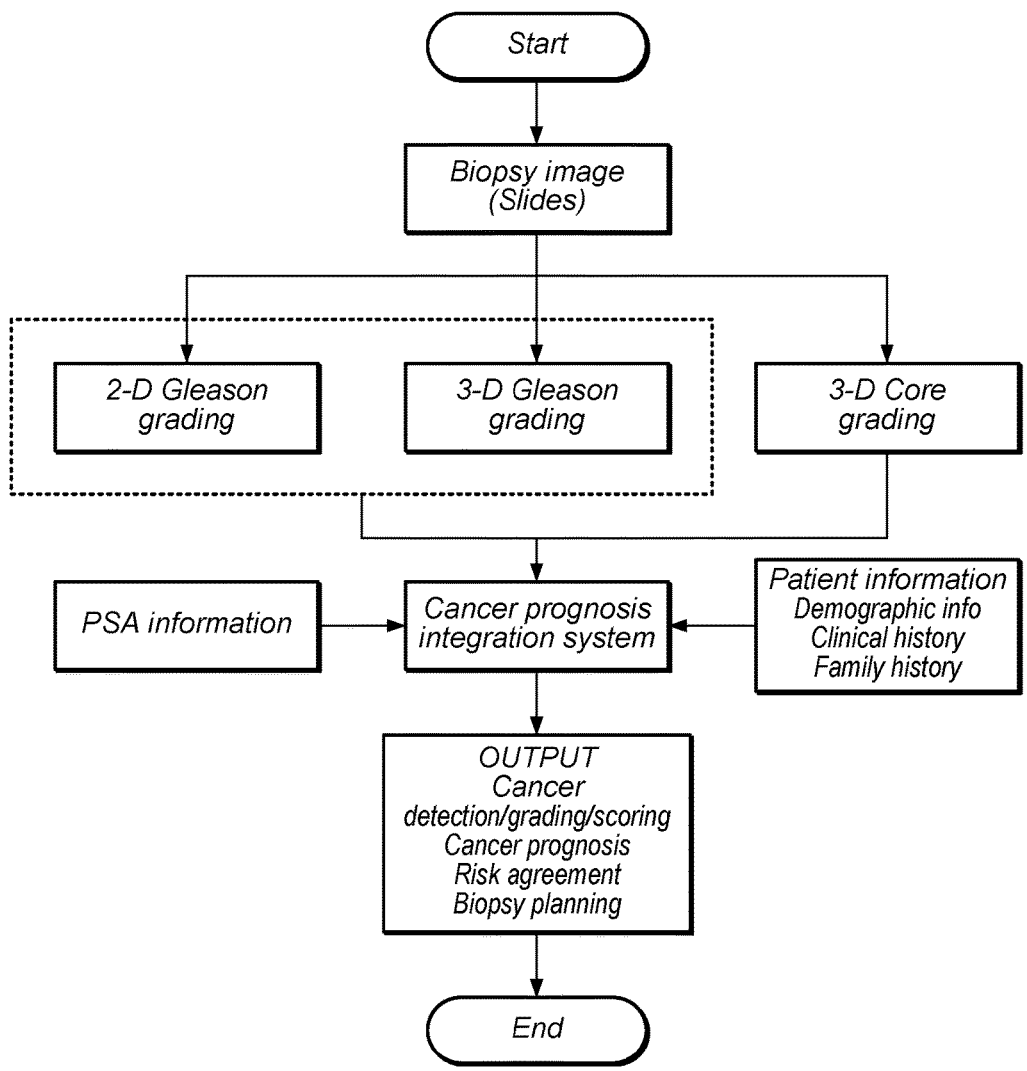
FIG. 17 is a flow diagram of the integration of CADs with PSA and patient's information for cancer prognosis.

Described herein is a system for the recognition and classification of Gleason grades of pathological biopsy images using three sub-systems for histology grading that are integrated at a later stage with patient information such as PSA information, age, race, and family history. The general hierarchy of such integration is illustrated in FIG. 17.

The first histology subsystem considers the classification of 2-D biopsy images; one or more of the previous systems may be used. The second subsystem, considers the classification of 3-D biopsy images. In this part, a 2-D image is mapped using certain mapping algorithms to 3-D space to have a 3rd dimension. The conventional way of visualizing regular 2-D biopsy images is replaced by a 3-D view to observe histological details in 3-D space. The objective of this subsystem is to verify the classification of the 2-D subsystem in terms of analyzing the unforeseen information that may exist in the 3-D representation. The classification performance of the 2-D and 3-D subsystem is going to be fused for accurate recognition performance. The third subsystem introduces the concept of 3-D core grading of prostate biopsy specimen. In this subsystem serial images of a stack of multiple 2-D tissue biopsy slices are captured from a given suspicious lesion in the prostate gland. The 3rd dimension of this stack represents the depth of the tumor or "core". It can be visualized as a 2-D internal image of the prostate gland when a vertical cut is made on the stack of the 3-D slices. The objective of this subsystem is to investigate tertiary patterns, and assigns a malignancy Gleason grade for the core (depth of the specimen). The final Gleason score resulted from these three subsystems can be looked at as a Gleason grade composed from 3 scores, the first two scores represent the Gleason score from the first two subsystems, and the third score is the core score as follows:

Gleason score=(predominant pattern grade+second predominant pattern grade+3-D core grade)

Regarding the PSA and patient information, information from these blocks will be integrated as an additional feature for accurate classification and prognostics purposes.

Biopsy images of prostate cancer form diversities in terms of structure, color information, edge information, and visualization of fine details associated with each distinct grade. A typical image recognition system for classification purpose is composed of the following three main blocks/phases: (1) Images preprocessing; (2) features extraction (feature vectors); and (3) classification. Considering the first block that is concerned with image preprocessing, image details are collected from images at different Gleason grades prior to feature vectors extraction phase. Preprocessing of images provides significant information in terms of visualization, segmentation, edge information prior to categorizing images in different cancer grades through feature vectors generation and classification.

In one embodiment of the present invention, methods for 2-D and 3-D grading systems integration are provided. The steps to achieve a prostate cancer prognosis system as a follows:

(1) Acquire PSA information attached with each graded biopsy image as follows: PSA level, PSA-Velocity, % free-to-total PSA.
(2) Acquire patient information attached with each labeled biopsy image as follows: age, race, Body-mass Index (BMI), and family history of cancer.
(3) Feature Vector Generation and Classifications of the above information for features integration with biopsy images features associated with 2-D, 3-D and Core grading classification. The systems provides in previous embodiments may be used.
(4) Verification of the whole system using subjective and/or objective measures. System output may be compared with biopsies graded by expert pathologists. Mean Opinion Score (MOS) may be used to measure the performance of the system. Also, DNA Microarrays results, if available for each patient, may be analyzed and compared with our system final output as an objective measure.

The introduction of a new novel Gleason grading concept considering different aspects of biopsy images ranging from 2-D to 3-D contributes to an enhanced output of more than just an accurate classification of cancer grade. The system of this embodiment integrates PSA and patient information along with results of cancer automatic grading from the proposed histology system. Hence, the final "expert system" output is expected to provide the following functions:

Provides an automated Gleason score to assets pathologist in accurate classification of cancer grades of prostate biopsy images.
Aids medical doctors by providing prognostic information about the stage and level of prostate cancer.
The generated accurate Gleason score contributes directly to more accurate risk assessment readings using the common available risk assessment calculators. Accuracy Contributes to more accurate risk assessment by integrating a more accurate Gleason grade with other risk assessment variables.
Biopsy planning by predicting biopsy locations having suspicious malignant tissues.

Implementation of the method/or system of embodiments of the invention can involve one/or combination of pre-developed or new risk assessment models and 2-D and 3-D Gleason grading/scoring systems. For example, we may use one of following risk assessment model: Prostate Cancer Prevention Trial Risk Calculator (PCPTRC) [21], D'Amico model [22], Kattan nomograms [23], and Cancer of the Prostate Risk Assessment (CAPRA) [24]). In general, a risk assessment system uses PSA level (blood test), Gleason grade, and T stage (size of the tumor on rectal exam and/or ultrasound) to group men as low, intermediate, or high-risk. In all these methods, the accurate detection, grading and scoring of biopsy images is a crucial step towards a better risk assessment.

Figure 28:
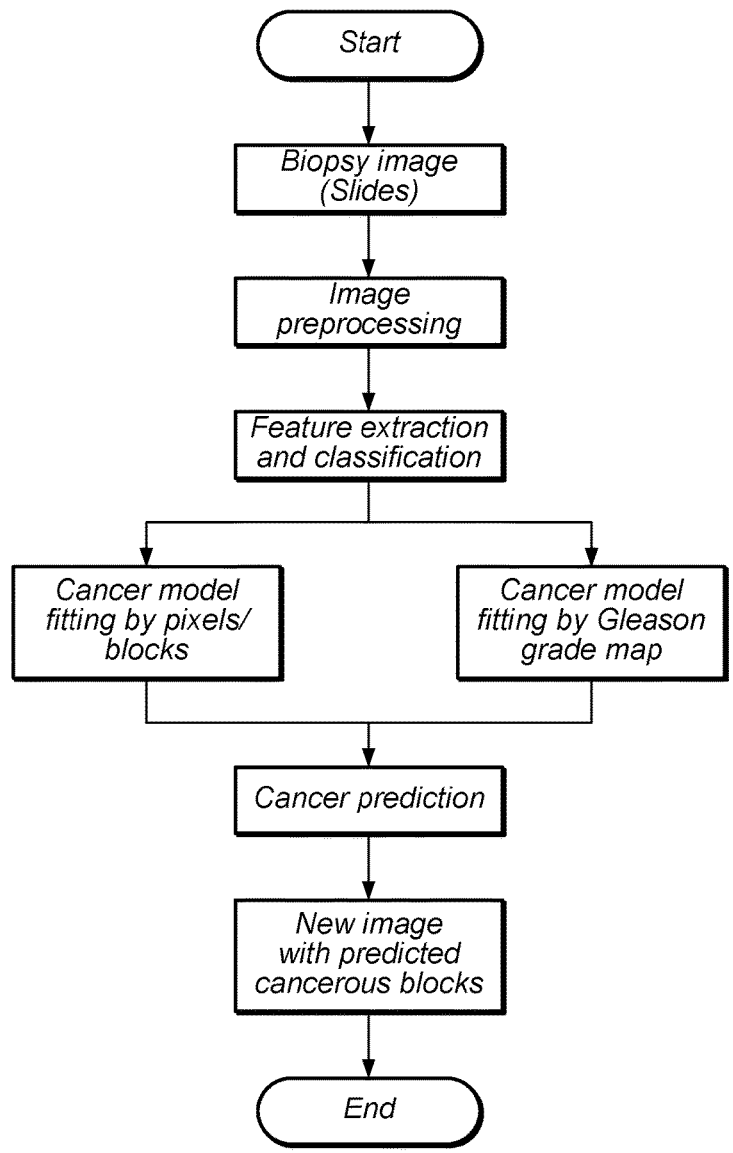
FIG. 28 shows a flow diagram for the implementation of a method for cancer prediction based on histopathology images grading.

System and Methods for Estimation, Prediction, and Cancer Grading Outside of the Histopathology Biopsy Images In another aspect of this embodiment, a method is provided for predicting the Gleason grade of blocks in histopathology biopsy images. The basic idea is to predict the state of missing blocks or to produce extrapolated values to know the cancer grade in a neighborhood outside the core extracted from the prostate gland during a needle biopsy procedure. To this end, two models are fitted. The first model is fitted by taking into account the distribution of Gleason grades within the processed 2-D or 3-D core. The second model is a pixel-based model, where the pixel value and other features discussed in previous embodiments can be extracted to construct a prediction model. Several algorithms, for example the Kalman filtering schemes [26] or similar techniques can be used to make the aforementioned predictions. Once the two predictions can be performed, they can be fused to get a unique cancer grade for the new predicted blocks. An exemplary procedure is shown in FIG. 28.

Referring in more details to the present embodiment, the model of the histopathology image is given by:

$$S(m,n)=AS(m-1,n)+Bw(m,n)$$

Where S is the state vector, A is a state transition matrix, B is an input matrix, w is random system noise. S represents the noisy observed image features, which is directly related to the morphology and textural features extracted for classification purposes. The vector w may be modeled as a Gaussian noise vector with zero mean, which represent variations in calculated features. As it was mentioned above, pixel- and block-based model fitting may be performed.

The observation equation is given by:

$$r(m,n) = h^T S(m, v(m,n))$$

Where h is an observation matrix and v is additive noise present in observations.

The next step is to generate a Kalman filter, for prediction of the cancerous grade of image blocks by estimating the state vector. In order to execute the 2-D filtering, we divide the 2-D problem into equivalent 1-D problems by applying line by line scanning or keeping constant the variable n or second dimension of the image or block, and then constructing a global state vector for all values of n.

For example, the equivalent 1-D Kalman filtering equations for a 1-D image scanning process are:

$$\vec{S}_{b\ b}(m) = A\ \vec{S}_{b\ b}(m-1)$$

$P_b(m) = AP_a(m-1)\ A^T + BQ_w B^T$, $Q_w$ is the correlation matrix of noise vector w.

$K(m) = P_b(m)h^T[hP_b(m)h^T + Q_v]^{-1}$, $Q_v$ is the correlation matrix of noise vector v.

$$\vec{S}_a(m) = \vec{S}_{b\ b}(m) + K(m)[r(m) - h\vec{S}_{b\ b}(m)]$$

$$P_a(m)[I - K(m)h]P_b(m)$$

The resulting estimated state vector is used as the input to a previously trained classifier to obtain the Gleason grade of the 2-D image patch. Extensions and generalizations of the theory of estimation by Kalman filtering may be used to generate estimated cancer grade of 2-D slices and then reconstruct 3-D images and assign a Gleason grade using the classifier for 3-D images developed in previous embodiments.

Cancer Tele-Screening System and Adjudication Schemes (System 9)

Figure 18:
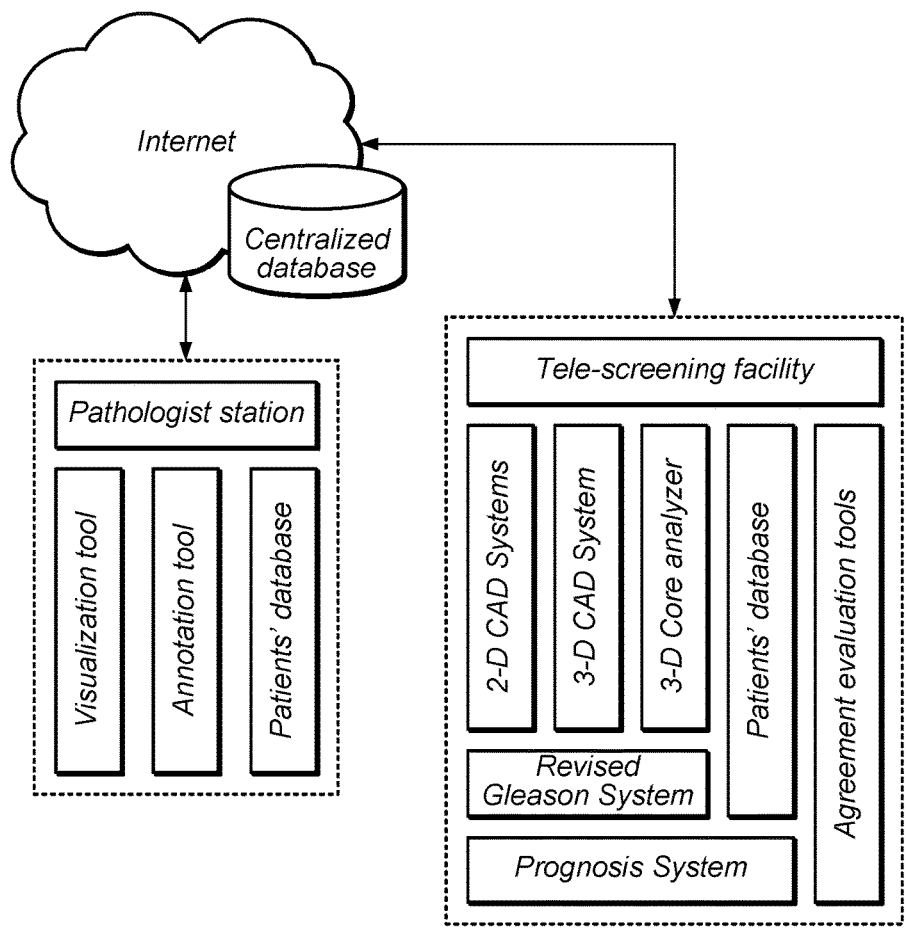
FIG. 18 shows the structure of the proposed cancer tele-screening system.

A tele-screening system according to an embodiment of the invention is provided for classification and diagnosis from digitized biopsy images in an ideal adjudication scheme. In this embodiment, the final report will be produce by integrating pathologists and automatic expert systems to produce a more accurate cancer diagnosis based on biopsy assessment. FIG. 18 shows the proposed tele-screening system. Several variations of the ideal adjudication scheme are addressed in different aspects of the present invention.

Figure 19:
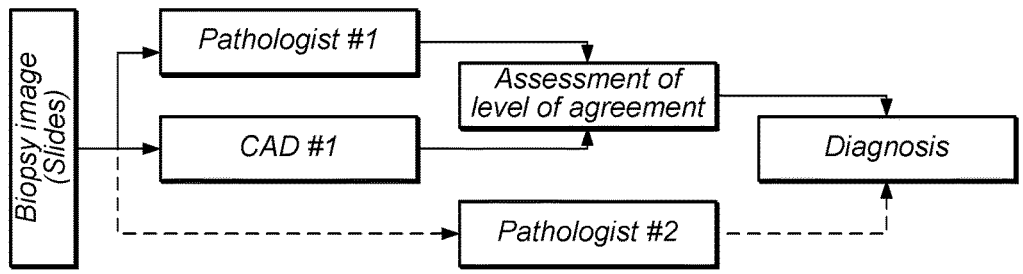
FIG. 19 is a method and system for diagnosis of cancer by integrating two pathologists and one CAD.

In one embodiment, an adjudication paradigm for cancer diagnosis biopsy by integrating one expert system is proposed. For instance, the configuration of the system is presented in FIG. 19 and includes the following steps: (1) One expert pathologist and one of the computerized systems (CAD or expert system) proposed in various embodiments of this invention perform independent assessment of all the tissue slides extracted by a biopsy procedure and produce a diagnostic report and annotated images. (2) An automatic algorithm analyzes the level of agreement between the two reports including patch analysis of slides compared to pathologist annotation. The assessment is considered complete if an acceptable level of agreement previously defined is reached. (3) If the minimum acceptable level of agreement is not reached, biopsy samples are assessed by a second pathologist. (4) The automatic algorithm of step (2) analyzes the level of agreement among the three reports in a patch-based basis and force decision, for example by majority voting rule. (5) The misclassified patches are added to the training database and the classification model is updated. (6) The final step uses cross-validation to ensure that the accuracy and other measurement such as sensitivity and specificity remain in an acceptable interval. For cross-validation, 5-fold, 10-fold, hold-out or leave-one-out methods may be used. This system is able to decrease the interpretation time of a biopsy and reduce the cost associated to a second pathologist.

Figure 20:
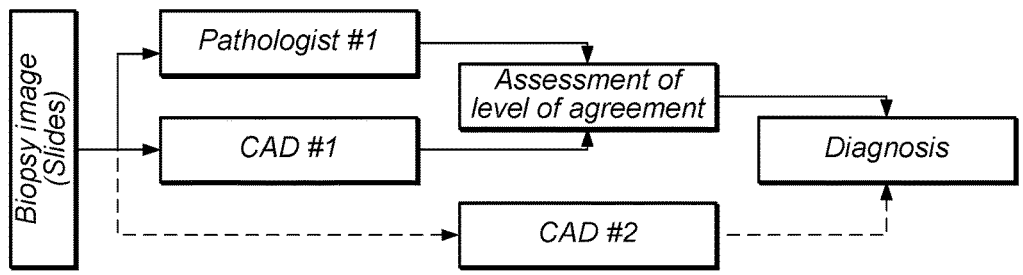
FIG. 20 is a method for diagnosis of cancer by integrating one pathologist and two CADs.

In another embodiment, an adjudication paradigm for cancer diagnosis biopsy by integrating two independent expert systems is proposed. The flow diagram of the method is shown in FIG. 20. The configuration of the system includes the following steps: (1) One expert pathologist and one of the computerized systems proposed in various embodiments of this invention perform independent assessment of all the tissue slides extracted by a biopsy procedure and produce a diagnostic report and annotated images. (2) An automatic algorithm analyzes the level of agreement between the two reports including patch analysis of slides compared to pathologist annotation. The assessment is considered complete if an acceptable level of agreement previously defined is reached. (3) If the minimum acceptable level of agreement is not reached, biopsy samples are assessed by a second expert system, which use different features from the first CAD. For instance, the first CAD may be based on morphological features and the second one on textural features. (4) The automatic algorithm of step (2) analyzes the level of agreement among the three reports in a patch-based basis and force decision, for example by majority voting rule. (5) The misclassified patches are added to the training database and the classification model is updated. (6) The final step uses a cross-validation to ensure that the accuracy and other measurement such as sensitivity and specificity remain in an acceptable interval. For cross-validation, 5-fold, 10-fold, hold-out or leave-one-out methods may be used. This system is able to decrease the interpretation time of a biopsy and further reduce the cost associated to second and third pathologists.

Figure 21:
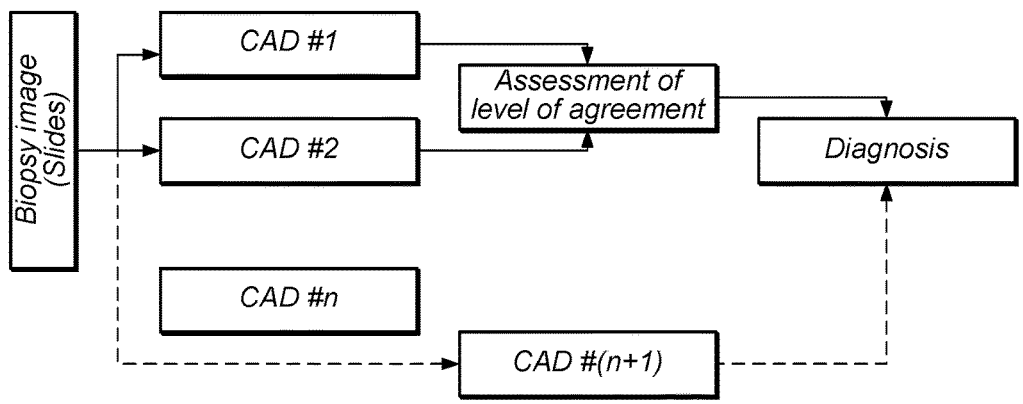
FIG. 21 presents a fully automated method for diagnosis of cancer by integrating three CADs.
Figure 22:
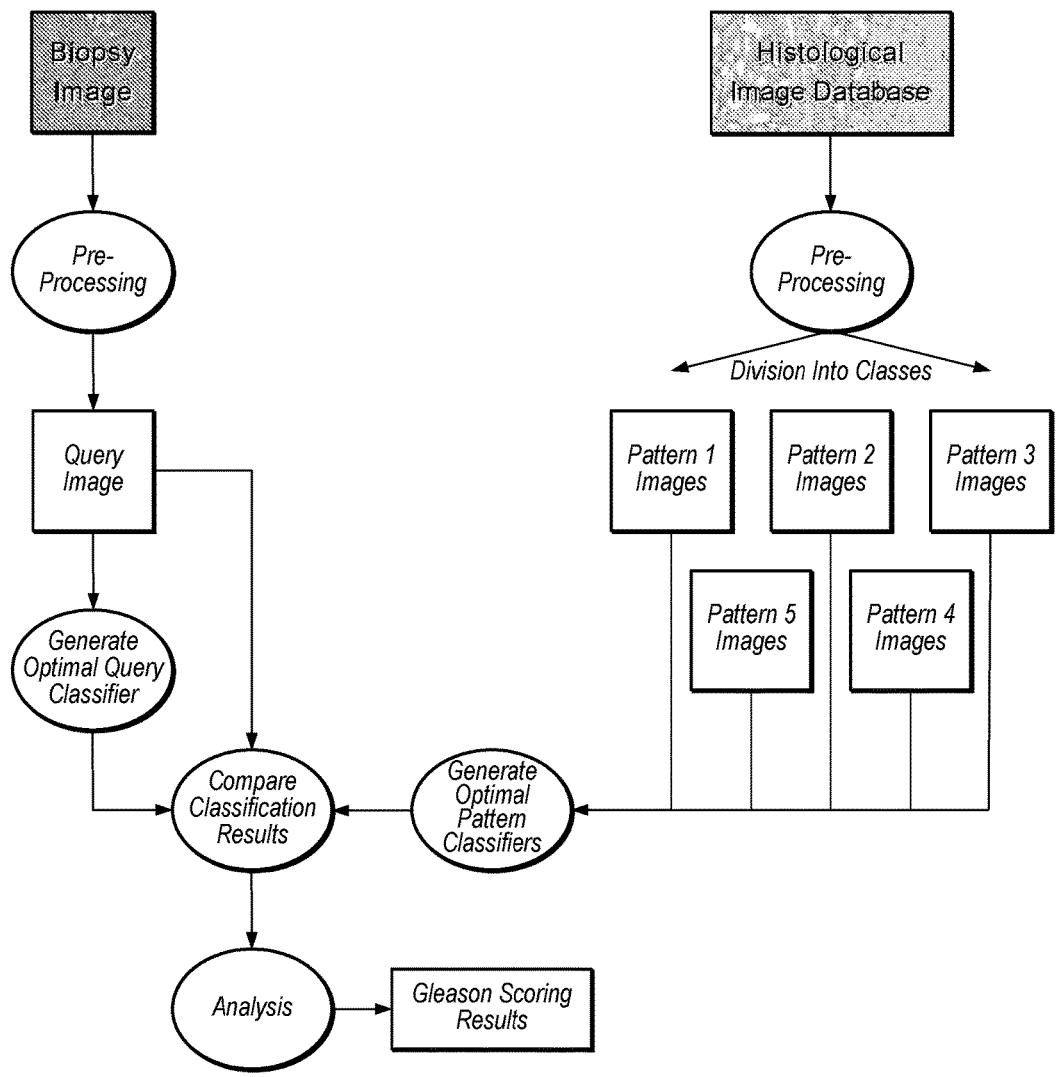
FIG. 22 shows an alternative exemplary classification scheme based on morphology- and architectural-based Gleason feature selection.

In another embodiment, an adjudication paradigm for cancer diagnosis biopsy by integrating three independent expert systems is provided. The flow diagram of the method is shown in FIG. 21. The configuration of the system includes the following steps: (1) Two CAD systems proposed in various embodiments of this invention perform independent assessment of all the tissue slides extracted by a biopsy procedure and produce a diagnostic report and annotated images. (2) An automatic algorithm analyzes the level of agreement between the two reports including patch analysis of slides compared to pathologist annotation. The assessment is considered complete if an acceptable level of agreement previously defined is reached. (3) If the minimum acceptable level of agreement is not reached, biopsy samples are assessed by a second expert system, which use different features from the first CADs. (4) The automatic algorithm of step (2) analyzes the level of agreement among the three reports in a patch-based basis and force decision, for example by majority voting rule. This system is able to decrease the interpretation time of a biopsy from minutes to seconds and further reduce the cost associated to second and third pathologists.

In broad embodiment, the present invention provides several systems for 2-D and 3-D classification of histology tissue samples. Such systems use unique feature vectors representing discriminative attributes of each cancerous pattern, for example Gleason patterns. In addition, other systems are proposed for cancer prognosis and cancer tele-screening by integrating one or more of the recognition systems. Moreover, novel algorithms for image processing such as edge detection, color fractal dimension and color region mapping are provided.

ADDITIONAL EMBODIMENTS

The present invention which is described hereinbefore with reference to flowchart and/or block diagram illustrations of methods, systems, devices, simulations, and computer program products in accordance with some embodiments of the invention and has been illustrated in detail by using a computer system. For instance, the flowchart and/or block diagrams further illustrate exemplary operations of the computer systems and methods of FIGS. 1 to 28. It is also conceivable that each block of the flowchart and/or block diagram illustrations, and combinations of blocks in the flowchart and/or block diagram illustrations, may be implemented by any computer program instructions and/or hardware. These computer program instructions may be provided to a processor of a general purpose computer, a microprocessor, a portable device such as cell phones, a special purpose computer or device, or other programmable data processing apparatus to produce a device, such that the instructions, which execute via the processor of the computer or other programmable data processing apparatus, create means for implementing the functions specified in the flowcharts and/or block diagrams or blocks. The computer program may also be supplied from a remote source embodied in a carrier medium such as an electronic signal, including a radio frequency carrier wave or an optical carrier wave.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for automatically detecting classifying, and grading cancerous regions of one or more biopsy images comprising:
    performing an image color standardization procedure on the one or more biopsy images to produce one or more color standardized biopsy images;
    performing edge detection on the one or more color standardized biopsy images;
    generating sets of texture-based feature vectors from the one or more color standardized biopsy images, wherein generating sets of texture-based feature vectors comprises extraction of a set of features from Fourier and wavelet transforms and fractal analysis of the one or more color standardized biopsy images;
    training a classifier by using the generated sets of texture-based feature vectors;
    classifying the one or more biopsy images according to the Gleason grading system;
    using the result of the classification to determine the Gleason score of the one or more biopsy images;
    wherein fractal analysis of the one or more color standardized biopsy images comprises:
        performing image filtering on the one or more color standardized biopsy images depending on nature of noise in the one or more color standardized biopsy image;
        binarizing the one or more color standardized biopsy images to produce binary images of the one or more color standardized biopsy images,
        calculating fractal dimension of the binary images by using different grid sizes based on a Differential Box Counting (DBC) algorithm; and
        fusing resulting fractal dimensions; and
    wherein binarizing the one or more color standardized biopsy images comprises:
        performing image filtering on the one or more color standardized biopsy images to produce one or more filtered images;
        smoothing the one or more filtered images using shape-dependent filters;
        calculating gradient vectors in the one or more filtered images using different kernels;
        selecting an edge angle in the one or more filtered images;
        determining threshold values within a local dynamic range in the one or more filtered images,
        generating several edge maps in the one or more filtered images, and
        fusing the generated edge maps together to form one or more binary images of the one or more color standardized biopsy images.

2. The method of claim 1, wherein the cross-validation methods are selected from a set of algorithms comprising: 5-fold, 10-fold, hold-out or leave-one-out.

3. The method of claim 1, further comprising applying an algorithm for image edge-preserving contrast enhancement which is based on HVS, Parameterized Logarithm Image Processing operations, and is integrated with morphological log-ratio approach in order to come up with an effective edge detection operator that is sensitive to edges of dark areas in the image.

* * * * *